United States Patent
Hada et al.

(10) Patent No.: US 7,745,097 B2
(45) Date of Patent: Jun. 29, 2010

(54) COMPOUND, MANUFACTURING METHOD THEREOF, ACID GENERATOR, RESIST COMPOSITION AND METHOD OF FORMING RESIST PATTERN

(75) Inventors: Hideo Hada, Kawasaki (JP); Takeshi Iwai, Kawasaki (JP); Takehiro Seshimo, Kawasaki (JP); Akiya Kawaue, Kawasaki (JP); Keita Ishiduka, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 12/174,293

(22) Filed: Jul. 16, 2008

(65) Prior Publication Data
US 2009/0023095 A1 Jan. 22, 2009

(30) Foreign Application Priority Data
Jul. 18, 2007 (JP) ............................. 2007-187593
Oct. 1, 2007 (JP) ............................. 2007-257492

(51) Int. Cl.
G03F 7/004 (2006.01)
G03F 7/30 (2006.01)

(52) U.S. Cl. ..................... 430/270.1; 430/326; 430/905; 430/910; 430/921; 430/922; 562/41; 562/44; 562/109; 562/113

(58) Field of Classification Search ............... 430/270.1, 430/326, 905, 910, 921, 922; 562/41, 44, 562/109, 113
See application file for complete search history.

(56) References Cited

U.S. PATENT DOCUMENTS

| 5,945,517 | A | 8/1999 | Nitta et al. | |
|---|---|---|---|---|
| 6,180,313 | B1 | 1/2001 | Yukawa et al. | |
| 7,074,543 | B2 | 7/2006 | Iwai et al. | |
| 7,301,047 | B2 | 11/2007 | Yoshida et al. | |
| 2007/0100158 | A1* | 5/2007 | Harada et al. | 560/149 |
| 2007/0100159 | A1* | 5/2007 | Yoshida et al. | 560/149 |
| 2007/0122750 | A1* | 5/2007 | Yamaguchi et al. | 430/311 |

FOREIGN PATENT DOCUMENTS

| JP | H09-208554 | 8/1997 |
|---|---|---|
| JP | H11-35551 | 2/1999 |
| JP | H11-35552 | 2/1999 |
| JP | H11-35573 | 2/1999 |
| JP | H11-322707 | 11/1999 |
| JP | 2003-241385 | 8/2003 |
| KR | 10-2007-0045969 | 5/2007 |
| WO | WO 2004/074242 | 9/2004 |

OTHER PUBLICATIONS

Office Action issued in counterpart Korean Patent Application No. 10-2008-0068190, dated Dec. 9, 2009.

* cited by examiner

Primary Examiner—John S Chu
(74) Attorney, Agent, or Firm—Knobbe, Martens, Olson & Bear, LLP

(57) ABSTRACT

There are provided a novel compound represented by a general formula (b1-1) shown below, which is useful as an acid generator for a resist composition and a manufacturing method thereof, a compound useful as a precursor of the novel compound and a manufacturing method thereof, an acid generator, a resist composition and a method of forming a resist pattern.

[Chemical Formula 1]

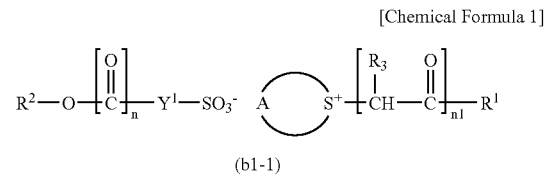

(b1-1)

(wherein, $R^1$ represents an aryl group or alkyl group which may contain a substituent group; $R^3$ represents a hydrogen atom or an alkyl group; n1 represents an integer of 0 or 1, and in the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded; A represents a bivalent group which forms a ring with 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; and $Y^1$ represents an alkylene group of 1 to 4 carbon atoms in which hydrogen atoms may be substituted with fluorine atoms.).

19 Claims, No Drawings

COMPOUND, MANUFACTURING METHOD THEREOF, ACID GENERATOR, RESIST COMPOSITION AND METHOD OF FORMING RESIST PATTERN

TECHNICAL FIELD

The present invention relates to a novel compound useful as an acid generator for a resist composition and a manufacturing method thereof, a compound useful as a precursor of the novel compound and a manufacturing method thereof, an acid generator, a positive resist composition and a method of forming a resist pattern.

This application claims priority from Japanese Patent Application No. 2007-187593 filed on Jul. 18, 2007 and Japanese Patent Application No. 2007-257492 filed on Oct. 1, 2007, the disclosure of which is incorporated by reference herein.

BACKGROUND ART

Lithography techniques include processes in which, for example, a resist film formed from a resist material is formed on top of a substrate, the resist film is selectively exposed with irradiation such as light, an electron beam or the like through a mask in which a predetermined pattern has been formed, and then a developing treatment is conducted, thereby forming a resist pattern of the prescribed shape in the resist film. Resist materials in which the exposed portions change to become soluble in a developing liquid are termed positive materials, whereas resist materials in which the exposed portions change to become insoluble in the developing liquid are termed negative materials.

In recent years, in the production of semiconductor elements and liquid crystal display elements, advances in lithography techniques have led to rapid progress in the field of miniaturization.

Typically, these miniaturization techniques involve shortening the wavelength of the exposure light source. Conventionally, ultraviolet radiation typified by g-line and i-line radiation has been used, but nowadays KrF excimer lasers and ArF excimer lasers are starting to be introduced in mass production of semiconductor elements. Furthermore, research is also being conducted into lithography techniques that use F2 excimer lasers, electron beams (EB), extreme ultraviolet radiation (EUV) and X-rays.

Resist materials are required to have lithography properties such as high sensitivity to the aforementioned light source and enough resolution to reproduce patterns with very fine dimensions. As resist materials which fulfill the aforementioned requirements, there is used a chemically-amplified resist containing a base resin that displays changed alkali solubility under action of acid, and an acid generator that generates acid upon exposure. For example, a chemically-amplified positive resist includes, as a base resin, a resin in which the alkali solubility increases under action of acid, and an acid generator, and when an acid is generated from the acid generator upon exposure in the formation of a resist pattern, the exposed portions are converted to an soluble state in an alkali developing solution.

Until recently, polyhydroxystyrene (PHS) or derivative resins (PHS-based resins) in which the hydroxyl groups have been protected with acid dissociable, dissolution inhibiting groups, which exhibit a high degree of transparency relative to KrF excimer laser (248 nm), have been used as the base resin of chemically-amplified resists. However, because PHS-based resins contain aromatic rings such as benzene rings, their transparency is inadequate for light with a wavelength shorter than 248 nm, such as light of 193 nm. Accordingly, chemically-amplified resists that use a PHS-based resin as the base resin have a disadvantage in that they have low resolution in processes that use, for example, light of 193 nm. As a result, resins (acrylic resins) that contain structural units derived from (meth)acrylate esters within the main chain are now widely used as base resins for resists that use ArF excimer laser lithography, as they exhibit excellent transparency in the vicinity of 193 nm. In the case of a positive resist, as the base resin, those which have a structural unit derived from (meth)acrylate ester including an aliphatic polycyclic group-containing, tertiary alkyl ester-type acid dissociable, dissolution inhibiting group, such as a structural unit derived from 2-alkyl-2-adamantyl (meth)acrylate, are mainly used (for example, see Patent Document 1). Here, the term "(meth)acrylate ester" is a generic term that includes either or both of the acrylate ester having a hydrogen atom bonded with the α-position and the methacrylate ester having a methyl group bonded with the α-position. The term "(meth)acrylate" is a generic term that includes either or both of the acrylate having a hydrogen atom bonded with the α-position and the methacrylate having a methyl group bonded with the α-position. The term "(meth)acrylic acid" is a generic term that includes either or both of the acrylic acid having a hydrogen atom bonded with the α-position and the methacrylic acid having a methyl group bonded with the α-position.

As an acid generator used in a chemically-amplified resist, a large variety of acid generators are proposed, and examples thereof include onium salt-based acid generators such as iodonium salts and sulfonium salts. [Patent Document 1] Japanese Unexamined Patent Application, First Publication No. 2003-241385.

DISCLOSURE OF THE INVENTION

Problems to be Solved by the Invention

As an anionic site of the onium salt-based acid generators described above, a perfluoroalkylsulfonate ion is generally used. In such an anionic site, a longer perfluoroalkyl chain is considered to be preferable, in order to suppress the diffusion of an acid after exposure. However, a perfluoroalkyl chain of 6 to 10 carbon atoms are persistent (hardly-degradable), therefore a nonafluorobutanesulfonate ion or the like has been used, because it can be handled more safely in terms of bioaccumulation potential. For these reasons, a novel compound more suitable as an acid generator for a resist composition is required.

The present invention takes the above circumstances into consideration, with an object of providing a novel compound useful as an acid generator for a resist composition and a manufacturing method thereof, a compound useful as a precursor of the novel compound and a manufacturing method thereof, an acid generator, a positive resist composition and a method of forming a resist pattern.

Means for Solving the Problems

To achieve the above object, the present invention employs the following constitutions.

A first aspect of the present invention is a compound represented by a general formula (b1-1) shown below (hereinafter, referred to as compound (B1)).

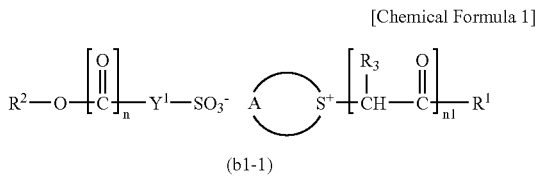

(b1-1)

(wherein, $R^1$ represents an aryl group or alkyl group which may contain a substituent group; $R^3$ represents a hydrogen atom or an alkyl group; n1 represents an integer of 0 or 1, and in the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded; A represents a bivalent group which forms a ring with 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; and $Y^1$ represents an alkylene group of 1 to 4 carbon atoms in which hydrogen atoms may be substituted with fluorine atoms.)

A second aspect of the present invention is a method of manufacturing a compound represented by a general formula (b1-1-1) shown below, which comprises the step of reacting a compound represented by a general formula (I) shown below, a compound represented by a general formula (II) shown below, and a copper catalyst, thereby obtaining a compound represented by the general formula (b1-1-1) (hereinafter, referred to as method of manufacturing compound (B1-1)).

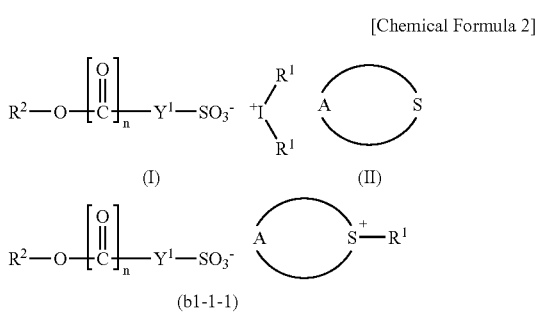

(b1-1-1)

(wherein, A represents a bivalent group which forms a ring with a 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; $Y^1$ represents an alkylene group of 1 to 4 carbon atoms in which hydrogen atoms may be substituted with fluorine atoms; and $R^1$ each independently represents an aryl group or alkyl group which may contain a substituent group.)

A third aspect of the present invention is a compound represented by a general formula (I) shown below (hereinafter, referred to as compound (I)).

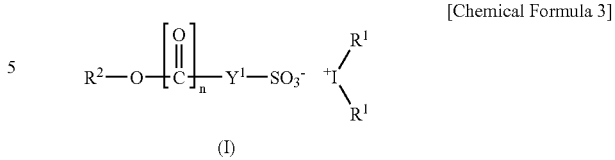

(I)

(wherein, $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; $Y^1$ represents an alkylene group of 1 to 4 carbon atoms in which hydrogen atoms may be substituted with fluorine atoms; and $R^1$ each independently represents an aryl group or alkyl group which may contain a substituent group.)

A fourth aspect of the present invention is a method of manufacturing a compound represented by a general formula (I) shown below (hereinafter, referred to as method of manufacturing compound (I)), which includes the step of reacting a compound represented by a general formula (I-1) shown below and a compound represented by a general formula (I-2) shown below, thereby obtaining the compound represented by the general formula (I).

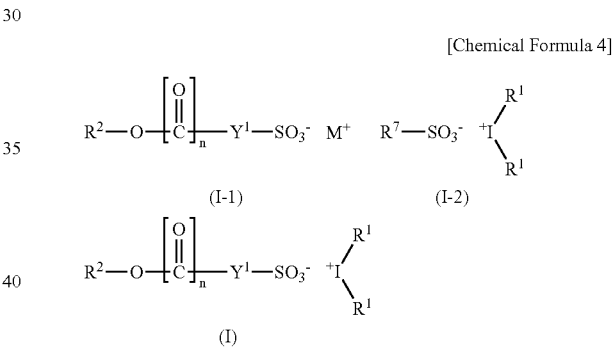

(wherein, $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; $Y^1$ represents an alkylene group of 1 to 4 carbon atoms in which hydrogen atoms may be substituted with fluorine atoms; $M^+$ represents an alkali metal ion; $R^1$ each independently represents an aryl group or alkyl group which may contain a substituent group; and $R^7$ represents an alkyl group or a fluorinated alkyl group.)

A fifth aspect of the present invention is an acid generator composed of the compound (B1) described in the first aspect.

A resist composition according to the sixth aspect of the present invention comprises a base resin (A) which displays changed solubility in an alkali developing solution under action of acid (hereinafter, referred to as component (A)), and an acid generator component (B) which generates an acid upon exposure (hereinafter, referred to as component (B)), wherein the component (B) comprises an acid generator (B1) composed of the compound represented by a general formula (b1-1) shown below.

[Chemical Formula 5]

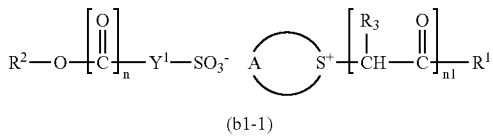

(b1-1)

(wherein, $R^1$ represents an aryl group or alkyl group which may contain a substituent group; $R^3$ represents a hydrogen atom or an alkyl group; n1 represents an integer of 0 or 1, and in the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded; A represents a bivalent group which forms a ring with 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; and $Y^1$ represents an alkylene group of 1 to 4 carbon atoms in which hydrogen atoms may be substituted with fluorine atoms.).

A seventh aspect of the present invention is a method of forming a resist pattern which includes forming a resist composition on a substrate using a resist composition described in the sixth aspect of the present invention; conducting exposure of the resist film; and developing the resist film with an alkali to form a resist pattern.

In the present specification and claims, terms are defined as follows.

The term "aliphatic" is a relative concept used in relation to the term "aromatic", and is defined as a group or compound that contains no aromaticity.

The term "aliphatic cyclic group (alicyclic group)" means a monocyclic or polycyclic group which has no aromaticity.

The term "alkyl group" is a concept containing a linear, branched and cyclic monovalent saturated hydrocarbon group, unless another definition is particularly provided.

The term "alkylene group" is a concept containing a linear, branched and cyclic bivalent saturated hydrocarbon group, unless another definition is particularly provided. The term "lower alkyl group" represents an alkyl group of 1 to 5 carbon atoms.

The term "structural unit" represents a monomer unit that contributes to the formation of a resin component (polymer compound).

The term "exposure" is used as a general concept involving irradiation with any form of radiation.

EFFECTS OF THE INVENTION

According to the present invention, a novel compound useful as an acid generator for a resist composition and a method of manufacturing thereof, a compound useful as a precursor of the novel compound and a method of manufacturing thereof, an acid generator, a resist composition and a method of forming a resist pattern.

BEST MODE FOR CARRYING OUT THE INVENTION

<<Compound (B1)>>

The compound (B1) according to the first aspect of the present invention is represented by the general formula (b1-1).

In the formula (b1-1), n1 is 0 or 1. In the case that n1 is 0, the compound (B1) is represented by a general formula (b1-1-1) shown below. In the case that n1 is 1 the compound (B1) is represented by a general formula (b1-1-2) shown below.

[Chemical Formula 6]

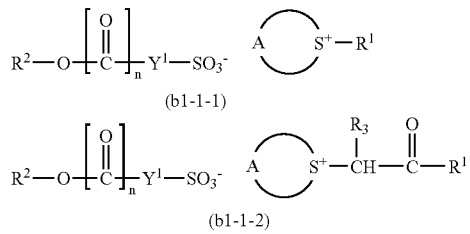

(b1-1-1)

(b1-1-2)

(wherein, $R^1$, $R^3$, A, $R^2$, n, and $Y^1$ are respectively the same as $R^1$, $R^3$, A, $R^2$, n, and $Y^1$ in the general formula (b1-1);

There is no limitation on the aryl group for $R^1$, and examples thereof include an aryl group of 6 to 20 carbon atoms. The aryl group is preferably an aryl group of 6 to 10 carbon atoms, because it can be synthesized inexpensively. Specific examples thereof include a phenyl group and a naphtyl group.

The aryl group may contain a substituent group. Here, the term "containing a substituent group" represents that a part of or all of hydrogen atoms in the non-substituted alkyl group is/are substituted with substituent groups (groups or atoms other than hydrogen atoms).

Examples of the substituent group which the aryl group may contain include an alkyl group, an alkoxy group, a halogen atom, a halogenated alkyl group, and a hydroxyl group.

The alkyl group as the subustituent group of the aryl group is preferably an alkyl group of 1 to 5 carbon atoms, and most preferably a methyl group, an ethyl group, a propyl group, an n-butyl group, or a tert-butyl group.

The alkoxy group as the substituent group of the aryl group is preferably an alkoxy group of 1 to 5 carbon atoms, more preferably a methoxy group, an ethoxy group, an n-propoxy group, an iso-propoxy group, an n-butoxy group, and a tert-butoxy group, and most preferably a methoxy group and an ethoxy group.

Examples of the halogen atom as the substituent group of the aryl group include a fluorine atom, a chlorine atom, a bromine atom, and an iodine atom. Of these, a fluorine atom is preferable.

Examples of the halogenated alkyl group as the substituent group of the aryl group include a group in which a part of or all of hydrogen atoms in an aforementioned alkyl group is/are substituted with an aforementioned halogen atoms.

There is no limitation on the alkyl group for $R^1$, and examples thereof include a linear, branched or cyclic alkyl group of 1 to 10 carbon atoms. The alkyl group preferably has 1 to 5 carbon atoms, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

The alkyl group may contain a substituent group. Here, the term "containing a substituent group" represents that a part of or all of hydrogen atoms in the non-substituted alkyl group is/are substituted with substituent groups (groups or atoms other than hydrogen atoms).

Examples of substituent groups which the alkyl group may contain include an alkoxy group, a halogen atom, and a hydroxyl group. The alkoxy group and the halogen atom are respectively the same as the alkoxy group and the hagelon atom described above in the substituent group which the aryl group may contain.

In the present invention, $R^1$ is preferably an aryl group which may contain a substituent group, more preferably a phenyl group or a naphtyl group which may contain a substituent group, and most preferably a phenyl group which may contain a substituent group.

There is no particular restriction on the alkyl group for $R^3$, and examples thereof include the alkyl group for $R^1$.

In the present invention, $R^3$ is preferably a hydrogen atom or a methyl group, and more preferably a hydrogen atom.

In the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded.

The ring is preferably a 5- to 7-membered ring structure, and more preferably a 5- or 6-membered ring structure.

A is a bivalent group which forms a ring with a 3- to 7-membered ring structure together with the sulfur atom with which A is bonded, and the ring may contain a substituent group.

In A, the ring is preferably a 5- to 7-membered ring structure, and more preferably a 5- or 6-membered ring structure.

Examples of the substituent group which the ring may contain include the same as the substituent groups which the aryl group for $R^1$ may contain.

The cationic site of the compound (B1) is particularly preferably a cationic site represented by a general formula (b1'-1) or (b1'-2) shown below.

[Chemical Formula 7]

$R^8-\overset{+}{S}\underset{(b1'-1)}{\overset{(CH_2)_a}{\diagdown}}$    $R^9\underset{(b1'-2)}{\overset{O}{\underset{\diagdown}{\diagup}}\overset{+}{S}\overset{(CH_2)_a}{\diagdown}}$ In the formula, $R^8$ and $R^9$ each independently represents a phenyl group, a naphtyl group, or an alkyl group of 1 to 5 carbon atoms which may contain a substituent group. The alkyl group for $R^8$ and $R^9$ is preferably a methyl group.

a is an integer of 1 to 3, and most preferably 1 or 2.

In the general formula (b1-1), the aromatic group for $R^2$ may be a hydrocarbon formed solely from carbon atoms and hydrogen atoms, or may be a heteroatom-containing group which has carbon atoms, hydrogen atoms, and hetero atoms other than the carbon atoms and hydrogen atoms. Specific examples thereof include groups in which one hydrogen atom has been removed from an aromatic hydrocarbon ring, such as a phenyl group, a biphenyl group, a fluorenyl group, a naphthyl group, an anthryl group, and a phenantryl group; heteroaryl groups in which a part of the carbon atoms which constitutes the ring(s) of these groups are substituted with heteroatoms such as oxygen atoms, sulfur atoms, and nitrogen atoms; and arylalkyl groups such as benzyl groups, phenethyl groups, 1-naphthylmethyl groups, 2-naphthylmethyl groups, 1-naphthylethyl groups, and 2-naphthylethyl groups.

The number of carbon atoms of the alkyl chain in the arylalkyl group is preferably 1 to 4, more preferably 1 or 2, and still more preferably 1.

The aromatic group for R2 may contain a substituent group. The substituent group is the same as the substituent group which the aryl group for $R^1$ may contain.

Examples of the linear alkyl group of 1 to 10 carbon atoms for $R^1$ include a methyl group, an ethyl group, a propyl group, a butyl group, a pentyl group, a hexyl group, a heptyl group, a octyl group, a nonyl group, and a decanyl group. Of these, a methyl group is preferable.

Examples of the branched alkyl group of 1 to 10 carbon atoms for $R^2$ include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group, and a 4-methylpentyl group.

An alkyl group for $R^2$ may contain a substituent group. The substituent group is the same as the substituent group which the alkyl group for $R^1$ may contain.

The linear or branched alkenyl group of 2 to 10 carbon atoms for $R^2$ preferably has 2 to 5 carbon atoms, more preferably 2 to 4, and still more preferably 3. Specific examples thereof include a vinyl group, a propenyl group (allyl group), a butynyl group, a 1-methylpropenyl group, and a 2-methylpropenyl group. Of these, a propenyl group is preferable.

An alkenyl group for $R^2$ may contain a substituent group. The substituent group is the same as the substituent group which the alkyl group for $R^1$ may contain.

Here, in $R^2$, the term "may contain a substituent group" represents that a part of or all of hydrogen atoms in an aromatic hydrocarbon group, a linear or branched alkyl group, or a linear or branched alkenyl group may be substituted with substituent groups (atoms or groups other than hydrogen atoms)

The number of substituent groups in $R^2$ may be either one, or two or more.

n may be 0 or 1.

$Y^1$ is an alkylene group of 1 to 4 carbon atoms in which hydrogen atoms may be substituted with fluorine atoms.

Examples of alkylene groups of 1 to 4 carbon atoms for $Y^1$ which may be fluorinated include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—; —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

$Y^1$ is preferably an alkylene group of 1 to 4 carbon atoms in which hydrogen atoms are substituted with fluorine atoms (fluorinated alkylene group), and more preferably a fluorinated alkylene group in which carbon atoms bonded with the adjacent sulfur atom are fluorinated. Examples of the flurorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; $CH_2CH_2CH_2CF_2$—, —$CH_2CH_2CF_2CF_2$—, —$CH_2CF_2CF_2CF_2$—, Among these, —$CF_2CF_2$—, —$CF_2CF_2CF_2$—, and —$CH_2CF_2CF_2$— are preferable, —$CF_2CF_2$— and —$CF_2CF_2CF_2$— are more preferable, and —$CF_2CF_2$— is particularly preferable.

In the present invention, the anionic site of the compound (B1) is preferably an anionic site represented by a general formula (b1"-1) shown below.

[Chemical Formula 8]

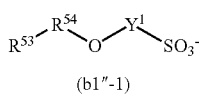

(b1"-1)

(wherein, $Y^1$ is as defined above; $R^{53}$ represents an alkenyl group or aryl group of 2 to 10 carbon atoms; and $R^{54}$ represents a linear or branched alkylene group of 1 to 5 carbon atoms.)

$R^{53}$ is preferably a vinyl group, a phenyl group or a naphthyl group, and more preferably a vinyl group or a naphthyl group.

$R^{54}$ is preferably a linear alkylene group of 1 to 5 carbon atoms, and most preferably a methylene group.

The compound (B1) in the present invention is preferably a compound composed of a cationic site represented by the general formula (b1'-1) or (b1'-2), and an anionic site represented by the general formula (b1"-1).

<<Method of Manufacturing Compound (B1)>>

There is no particular restriction on the method of manufacturing the compound (B1) of the present invention, and known methods of manufacturing sulfonium salts can be used.

For example, the compound (B1) can be obtained by reacting a compound (b0-1) represented by a general formula (b0-1) shown below and a compound (b0-2) represented by a general formula (b0-2) shown below.

[Chemical Formula 9]

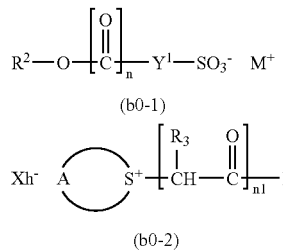

(wherein, $R^2$, n, $Y^1$, A, $R^3$, n1, and $R^1$ are respectively the same as $R^2$, n, $Y^1$, A, $R^3$, n1, and $R^1$ in the general formula (b1-1); $M^+$ represents an alkali metal ion; and $Xh^-$ represents a halogen ion.)

Examples of alkali metal ions for $M^+$ include a sodium ion, a lithium ion, and a potassium ion. Of these, a sodium ion or a lithium ion is preferable.

Examples of halogen ion for $Xh^-$ include a chlorine ion, a bromine ion, and an iodine ion. Of these, a chlorine ion or a bromine ion is preferable.

The compound (b0-1) and the compound (b0-2) can be reacted, for example, by being contacted in a solvent such as water or dichloromethane.

There is no particular restriction on the method of manufacturing the compound (b0-1). For example, a compound represented by a general formula (b0-1-11) shown below is reacted in a solvent such as a tetrahydrofuran or water, or in an aqueous solution of an alkali metal hydroxide such as a sodium hydrate or a lithium hydroxide, thereby obtaining a compound represented by a general formula (b0-1-12) shown below, and then the compound represented by the general formula (b0-1-12) is dehydratively-condensed with an alcohol represented by a general formula (b0-1-13) shown below, thereby obtaining a compound represented by the general formula (b0-1) in which n is 1 (that is, a compound represented by a general formula (b0-1-01) shown below).

[Chemical Formula 10]

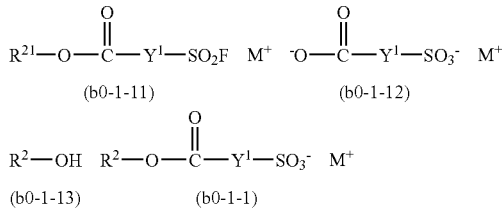

(wherein, $R^{21}$ represents an alkyl group of 1 to 5 carbon atoms; $Y^1$, $M^+$ and $R^2$ are respectively the same as $Y^1$, $M^+$ and $R^2$ described in the general formula (b0-1); $Xh^-$ is the same as $Xh^-$ described in the general formula (b0-2).)

Also, for example, a compound represented by a general formula (b0-1-01) shown below and a compound represented by a general formula (b0-1-02) shown below are reacted in an organic solvent such as anhydrous diglyme, thereby obtaining a compound represented by a general formula (b0-1-03) shown below, and then the compound represented by the general formula (b0-1-03) is reacted with an alkali methal hydroxide such as a sodium hydroxide or a lithium hydroxide in an organic solvent such as a tetrahydrofran, an acetone, and a methyl ethyl ketone, thereby obtaining a compound represented by the general formula (b0-1) in which n is 0 (that is, a compound represented by a general formula (b0-1-0) shown below).

[Chemical Formula 11]

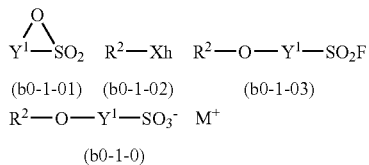

(wherein, $Y^1$, $M^+$ and $R^2$ are respectively the same as $Y^1$, $M^+$ and $R^2$ described in the general formula (b0-1); $Xh^-$ is the same as $Xh^-$ described in the general formula (b0-2).)

There is no particular restriction on the method of manufacturing the compound (b0-2). For example, the compound (b0-2) can be obtained by introducing a group represented by —$[CH(R^3)—CO]_{n1}$—$R^1$ to a sulfur atom of a compound represented by a general formula (b0-2-1) shown below, using a conventional method. As a specific example, in the case of n1 is 0, a compound represented by a general formula (b0-2-1) shown below is oxidized to change the part of "—S—" in the compound to "—S(=O)—", and then an aromatic hydrocarbon such as a benzene, or an alkane such as a methane is reacted in the presence of a catalyst such as an aluminum chloride, thereby obtaining the compound represented by the general formula (b0-2) in which n1 is 0. In the case of n1 being 1, for example, a commercially available bromide may be used.

[Chemical Formula 12]

(b0-2-1)

(wherein, A is as defined above.)

In the case that n1 is 0, that is, in the case that the compound (B1) is the compound represented by the general formula (b1-1-1) (hereinafter, sometimes referred to as compound (B1-1)), a method of manufacturing the compound (B1-1) of the present invention, which is described below, is preferable as a method of manufacturing the compound (B1-1).

<<Method of Manufacturing Compound (B1-1)>>

A method of manufacturing the compound (B1-1) (hereinafter, referred to as manufacturing method (1)) according to the second aspect of the present invention comprises the step of reacting a compound represented by a general formula (I) shown below, a compound represented by a general formula (II) shown below, and a copper catalyst, thereby obtaining the compound (B1-1) represented by the general formula (b1-1-1).

By conducting these steps, $R^1$ in the compound (I) is introduced to the sulfur ion in the compound (II), thereby forming a sulfonium ion. The sulfonium ion and the anionic site of the compound (I) form a salt, thereby obtaining the compound (B1-1).

[Chemical Formula 13]

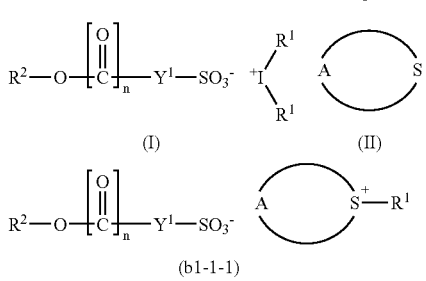

(wherein, A represents a bivalent group which forms a ring with a 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; $Y^1$ represents an alkylene group of 1 to 4 carbon atoms in which hydrogen atoms may be substituted with fluorine atoms; and $R^1$ each independently represents an aryl group or alkyl group which may contain a substituent group.)

In the formula, A, $R^2$, n, $Y^1$ and $R^1$ are respectively the same as A, $R^2$, $Y^1$, $R^1$ described in the general formula (b-1).

The compound (I) used above is a novel compound. The compound (I) can be produced, for example, by a method of manufacturing the compound (I) described below.

As the compound (II), a commercially available compound may be used, or a compound obtained by synthesis may be used.

The copper catalyst is preferably bivalent copper catalyst, and specific examples thereof include a compound represented by a general formula (III) shown below (hereinafter, referred to as compound (III)).

[Chemical Formula 14]

(III)

(wherein, $R^6$ represents an aryl group which may contain a substituent group.)

In the formula, the aryl group which may contain a substituent group for $R^6$ is the same as those described in the aryl group which may contain a substituent group for R.

Specific examples of the compound (III) include a copper benzoate (II). As the compound (III), a commercially available compound can be used.

There is no particular restriction on the method of reacting the compound (I), the compound (II) and the copper catalyst. Examples thereof include a method of reacting the compound (I), the compound (II) and the copper catalyst in the reaction solvent.

There is no particular restriction on the reaction solvent as long as it can dissolve materials, specific examples thereof include chlorobenzene and toluene.

The reaction temperature is preferably from 50 to 150° C., and more preferably 90 to 120° C.

The reaction time depends on the reactive property, the reaction temperature or the like of the compounds (I) and (II), but usually it is preferably 10 to 180 minutes, and more preferably 30 to 90 minutes.

The used amount of the compound (II) is preferably within a range approximately from 0.5 to 3 molar equivalent based on the used amount of the compound (I), and more preferably within a range from 0.9 to 1.5 molar equivalent.

The used amount of the copper catalyst is preferably within a range approximately from 0.01 to 0.5 molar equivalent based on the used amount of the compound (I), and more preferably within a range from 0.02 to 0.1 molar equivalent.

A structure of the compound (B1-1) obtained through the above steps can be confirmed by a general organic analysis method such as a $^1$H-NMR (nuclear magnetic resonance) spectrum method, a $^{13}$C-NMR spectrum method, a $^{19}$F-NMR spectrum method, an IR (infrared resonance) spectrum method, a MS (mass spectrometry) method, an element analysis, and an X-ray crystallographic analysis.

<<Compound (I)>>

A compound (I) according to the third aspect of the present invention is represented by the general formula (I).

In the formula (I), $R^2$, n, $Y^1$ and $R^1$ are respectively the same as $R^2$, n, $Y^1$ and $R^1$ described in the general formula (b1-1).

The compound (I) is useful as a precursor of the compound (B1-1), and is suitably used in a manufacturing method (1) of the compound (B1-1).

Also, the compound (1) itself is available as an acid generator, and can be blended in a resist composition as an acid generator.

<<Method of Manufacturing Compound (I)>>

A method of manufacturing the compound (I) according to the fourth aspect of the present invention includes the step of reacting a compound represented by a general formula (I-1) shown below (hereinafter, referred to as compound (I-1)) and a compound represented by a general formula (I-2) shown below (hereinafter, referred to as compound (I-2)) thereby obtaining the compound (I).

[Chemical Formula 15]

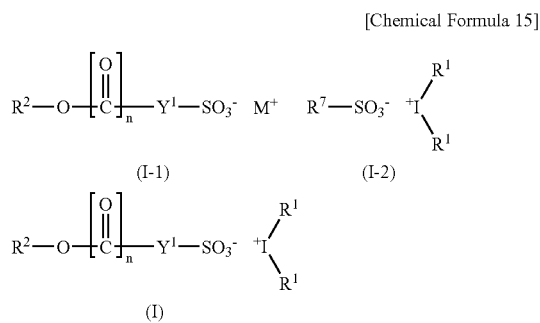

(wherein, $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0 or 1; $Y^1$ represents an alkylene group of 1 to 4 carbon atoms in which hydrogen atoms may be substituted with fluorine atoms; $M^+$ represents an alkali metal ion; $R^1$ each independently represents an aryl group or alkyl group which may contain a substituent group; and $R^7$ represents an alkyl group or a fluorinated alkyl group.)

In the formula, $R^2$, n, $Y^1$ and $R^1$ are respectively the same as $R^2$, n, $Y^1$ and $R^1$ described in the general formula (b1-1).

Examples of alkali metal ions for $M^+$ include a sodium ion, a lithium ion, and a potassium ion.

The alkyl group or fluorinated alkyl group for $R^7$ may be linear, branched, or cyclic.

The number of carbon atoms in the linear or branched alkyl group for $R^7$ is preferably from 1 to 10, more preferably from 1 to 8, and still more preferably from 1 to 4.

The number of carbon atoms in the cyclic alkyl group of $R^7$ is preferably from 4 to 15, more preferably from 4 to 10, and most preferably from 6 to 10.

Examples of the fluorinated alkyl group include groups in which a part or all of hydrogen atoms in the alkyl group is/are substituted with fluorine atoms.

$R^7$ is preferably an alkyl group, more preferably a linear alkyl group, and most preferably a methyl group.

The compound (I-1) can be synthesized, for example, using the method of manufacturing the compound (b0-1) described above.

As the compound (I-2), a commercially available compound can be used.

The compound (I-1) and the compound (I-2) can be reacted, for example, by being contacted in a solvent such as water or dichloromethane.

A structure of the compound obtained through the above steps can be confirmed by a general organic analysis method such as a $^1$H-NMR (nuclear magnetic resonance) spectrum method, a $^{13}$C-NMR spectrum method, a $^{19}$F-NMR spectrum method, an IR (infrared resonance) spectrum method, a MS (mass spectrometry) method, an element analysis, and an X-ray crystallographic analysis.

<<Acid Generator>>

An acid generator according to the fifth aspect of the present invention is composed of the compound (B1) described in the first aspect.

The acid generator is useful as an acid generator for a chemically-amplified resist composition, for example, as a acid generator (B) of the resist composition according to the sixth aspect of the present invention, which is described below.

<<Resist Composition>>

A resist composition according to the sixth aspect of the present invention includes a base resin (A) which displays changed solubility in an alkali developing solution under action of acid (hereinafter, referred to as component (A)), and an acid generator component (B) which generates an acid upon exposure (hereinafter, referred to as component (B)), wherein the component (B) comprises an acid generator (B1) composed of the compound represented by the general formula (b1-1).

When a resist film is formed by using the resist composition, and selective exposure is conducted in the formation of the resist pattern, the component (A) changes solubility in an alkali developing solution under action of acid generated from the component (B). As a result, whereas the exposed portions of the resist film change solubility in an alkali developing solution, the unexposed portions don't change solubility in an alkali developing solution. Therefore, if the resist composition is a positive resist composition, the exposed portions are dissolved to be removed, thereby forming a resist pattern. On the other hand, if the resist composition is a negative resist composition, the unexposed portions are dissolved to be removed, thereby forming a resist pattern.

The resist composition of the present invention may be a negative resist composition or a positive resist composition.

<Component (A)>

As the component (A), one kind of organic compounds used as a resin component for a chemically-amplified resist can be used alone, or two or more of them can be used in combination.

Here, the term "base component" represents an organic compound which has a film-forming performance, and the molecular weight thereof is preferably 500 or more. When the molecular weight of the organic compound is 500 or more, the film-forming performance can be improved, and a nano-level resist pattern can easily be formed.

The organic compounds whose molecular weight is 500 or more can be classified broadly into a lower molecular weight organic compound whose molecular weight is within a range from 500 to less than 2000 (hereinafter, referred to as lower molecular weight compound), and a resin (polymer material) whose molecular weight is 2000 or more. As the lower molecular weight compound, a non-polymer is usually used. In the cause of using a resin (polymer, copolymer), the polystyrene equivalent molecular weight determined by gel permeation chromatography (GPC) is used as "molecular weight". Hereinafter, in the case of just using the term "resin", it represents a resin with a molecular weight of 2000 or more.

As the component (A), a resin which changes the solubility in an alkali solution under action of acid can be used, and also a lower molecular weight compound which changes the solubility in an alkali solution under action of acid can be used.

In the case that the resist composition of the present invention is a negative resist composition, a resin soluble in an alkali developing solution is used as the component (A), and a cross-linking agent is blended with the negative resist composition.

In the negative resist composition, when acid is generated from the component (B) upon exposure, the action of this acid causes cross-linking between the alkali-soluble resin and the cross-linking agent, and the cross-linked portion becomes poorly-soluble in an alkali developing solution. Therefore, in the formation of a resist pattern, when a resist film obtained by applying the negative resist composition on the substrate is subjected to selective exposure, the exposed area becomes poorly-soluble in an alkali developing solution, while the unexposed area remains soluble in the alkali developing solution, and hence a resist pattern can be formed by a developing treatment with an alkali.

A coating film composed of a negative resist composition has the property that it is soluble in an alkali developer before exposure, and changes to be insoluble after exposure.

As the alkali-soluble resin, it is preferable to use a resin having a structural unit derived from at least one of an α-(hydroxyalkyl)acrylic acid and a lower alkyl ester of α-(hydroxyalkylacrylic acid, because it enables formation of a satisfactory resist pattern with minimal swelling. Here, the ten "α-(hydroxyalkyl) acrylic acid" represents one or both of an acrylic acid in which a hydrogen atom is bonded with the carbon atom at the α-position with which the carboxyl group bonded, and an α-hydroxyalkylacrylic acid in which a hydroxyalkyl group (preferably a hydroxyalkyl group of 1 to 5 carbon atoms) is bonded with the carbon atom at the α-position.

As a cross-linking agent, usually, an amino-based cross-linking agent such as a glycoluril that contains a methylol group or an alkoxymethyl group is preferable, because it enables an excellent resist pattern with minimal swelling to be formed. The blend quantity of the cross-linking agent is preferably within a range from 1 to 50 parts by weight, relative to 100 parts by weight of the alkali soluble resin.

If the resist composition of the present invention is a positive resist composition, a base component which exhibits increased solubility in an alkali developing solution under action of acid can be used as the component (A). The component (A) is hardly-soluble in an alkali developing solution before exposure, and when an acid is generated from the component (B) upon exposure, the component (A) increases solubility in an alkali solution under action of acid. Therefore, in the formation of a resist pattern, when a resist film obtained by applying the positive resist composition on the substrate is subjected to selective exposure, the exposed area becomes soluble in an alkali, while the unexposed area remains insoluble in alkali, and hence a resist pattern can be formed by a developing treatment with an alkali.

In the resist composition of the present invention, the component (A) is preferably a base component which exhibits increased solubility in an alkali developing solution under action of acid. That is, the resist composition of the present invention is preferably a positive resist composition.

The component (A) may be a resin component (A1) which displays increased solubility in an alkali developing solution under action of acid (hereinafter, sometimes referred to as component (A1)), may be a lower molecular compound (A2) which displays increased solubility in an alkali developing solution under action of acid (hereinafter, sometimes referred to as component (A2)), or may be a mixture of components (A1) and (A2).

[Component (A1)]

As the component (A1), one kind can be used alone selected from resin components (base resins) used as base components for a chemically-amplified resist, or two or more can be used in combination.

In the present invention, the component (A1) preferably contains a structural unit derived from an acrylate ester.

Here, the term "structural unit derived from an acrylate ester" in the present specification and claims represents a structural unit formed by cleavage of the ethylenic double bond of an acrylate ester.

The term "acrylate ester" is a concept containing an acrylate ester in which a hydrogen atom is bonded with a carbon atom at the α-position, and an α-substituted acrylate ester in which a hydrogen atom bonded with a carbon atom at the α-position is substituted with another substituent group (an atom or group other than a hydrogen atom). Examples of the substituent group include a lower alkyl group, and a halogenated lower alkyl group.

The term "α-position (carbon atom at the α-position)" in a structural unit derived from an acrylate ester represents a carbon atom with which a carbonyl group is bonded, if not otherwise specified.

In the acrylate ester, specific examples of the lower alkyl group as the substituent group at the α-position include linear or branched lower alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group include groups in which a part of or all of the hydrogen atoms of the aforementioned "lower alkyl group for the substituent group at the α-position" are substituted with halogen atoms. Examples of the halogen atom include a fluorine atom, a chlorine atom, an iodine atom, and a bromine atom. Of these, a fluorine atom is preferable.

In the present invention, the group which is bonded with the α-position is preferably a hydrogen atom, a lower alkyl group or a halogenated lower alkyl group, more preferably a hydrogen atom, a lower alkyl group or a fluorinated lower alkyl group, and still more preferably a hydrogen atom or a methyl group, in terms of industrial availability.

The component (A1) particularly preferably includes a structural unit (a1) derived from an acrylate ester which has an acid dissociable, dissolution inhibiting group.

Also, it is preferable that the component (A1) further includes a structural unit (a2) derived from an acrylate ester which has a lactone-containing cyclic group, in addition to the structural unit (a1).

The component (A1) preferably includes a structural unit (a3) derived from an acrylate ester which has a polar group-containing aliphatic hydrocarbon group, in addition to the structural unit (a1), or the structural units (a1) and (a2).

Structural Unit (a1)

As the acid dissociable, dissolution inhibiting group in the structural unit (a1), any of the groups that have been proposed as acid dissociable, dissolution inhibiting groups for the base resins of chemically amplified resists can be used, provided the group has an alkali dissolution-inhibiting effect that renders the entire component (A1) alkali-insoluble prior to dissociation, and then following dissociation by action of acid, causes the entire component (A1) to change to an alkali-soluble state. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known.

Here, the term "tertiary alkyl ester" represents a structure in which an ester is formed by substituting the hydrogen atom of a carboxyl group with a chain-like or cyclic alkyl group, and a tertiary carbon atom within the chain-like or cyclic alkyl group is bonded with the oxygen atom at the terminal of the carbonyloxy group (—C(O)—O—). In the tertiary alkyl ester, the bond of the oxygen atom with the tertiary carbon atom is cleaved by the action of acid.

Here, the chain-like or cyclic alkyl group may contain a substituent group.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" represents a branched structure having no aromaticity. The "aliphatic branched, acid dissociable, dissolution inhibiting group" is not limited to groups (hydrocarbon groups) composed of carbon atoms and hydrogen atoms, and is preferably a hydrocarbon group. Further, the "hydrocarbon group" may be either saturated or unsaturated, and is preferably saturated.

Examples of aliphatic branched, acid dissociable, dissolution inhibiting groups include tertiary alkyl groups of 4 to 8 carbon atoms, and specific examples include a tert-butyl group, a tert-pentyl group and a tert-heptyl group.

The term "aliphatic cyclic group (alicyclic group)" means a monocyclic or polycyclic group which has no aromaticity.

The "aliphatic cyclic group" within the structural unit (a1) may or may not contain a substituent group. Examples of substituent groups include a lower alkyl group of 1 to 5 carbon atoms, a fluorine atom, a fluorinated lower alkyl group of 1 to 5 carbon atoms, and an oxygen atom (=O).

The basic ring of the "aliphatic cyclic group" exclusive of substituent groups is not limited to groups (hydrocarbon groups) composed of carbon atoms and hydrogen atoms, and is preferably a hydrocarbon group. Further, the "hydrocarbon group" may be either saturated or unsaturated, and is preferably saturated. The "aliphatic cyclic group" is preferably a polycyclic group.

Examples of the aliphatic cyclic groups include groups in which one or more hydrogen atoms have been removed from a monocycloalkane or a polycycloalkane such as a bicycloalkane, tricycloalkane or tetracycloalkane in which a lower alkyl group, a fluorine atom or a fluorinated lower alkyl group may or may not be included as a substituent group. Specific examples include groups in which at least one hydrogen atom has been removed from a monocycloalkane such as cyclopentane and cyclohexane; and groups in which at least one hydrogen atom has been removed from a polycycloalkane such as adamantane, norbornane, isobornane, tricyclodecane or tetracyclododecane.

As the aliphatic cyclic group-containing acid dissociable, dissolution inhibiting group, for example, a group which has a tertiary carbon atom on the ring structure of the cycloalkyl group can be mentioned. Specific examples thereof include 2-methyl-2-adamantyl group and a 2-ethyl-2-adamantyl group. Further, in the structural units represented by general formulae (a1"-1) to (a1"-6) shown below, groups bonded with the oxygen atom of the carbonyloxy group (—C(O)—O—), that is, groups having an aliphatic cyclic group such as an adamantyl group, a cyclohexyl group, a cyclopentyl group, a norbornyl group, a tricyclodecanyl group or a tetracyclodecanyl group, and a branched alkylene group having a tertiary carbon atom bonded thereto, can be exemplified.

[Chemical Formula 16]

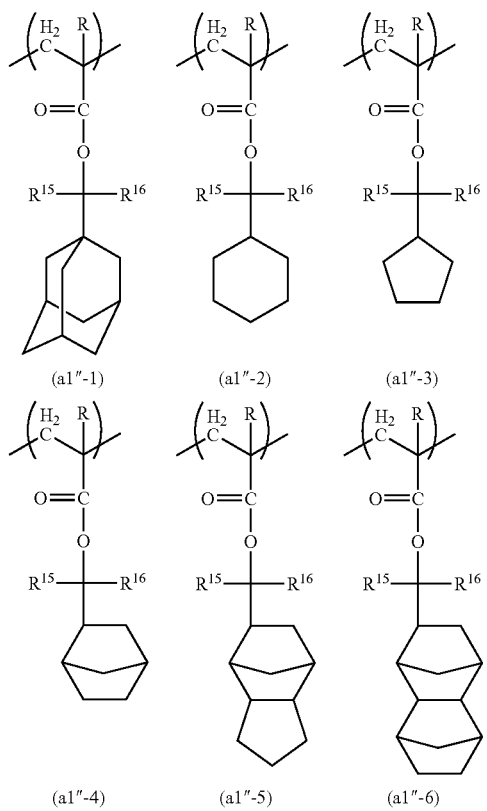

(a1"-1)   (a1"-2)   (a1"-3)

(a1"-4)   (a1"-5)   (a1"-6)

(wherein, R represents a hydrogen atom, a lower alkyl group or a halogenated lower alkyl group; and $R^{15}$ and $R^{16}$ each independently represents an alkyl group (which may be linear or cyclic, and is preferably an alkyl group of 1 to 5 carbon atoms).)

In the general formulae (a1"-1) to (a1"-6), the lower alkyl group or halogenated lower alkyl group for R are the same as the lower alkyl group or halogenated lower alkyl group which can be bonded with the a-position of the aforementioned acrylate ester.

An "acetal-type acid dissociable, dissolution inhibiting group" generally replaces a hydrogen atom at the terminal of an alkali-soluble group such as a carboxy group or a hydroxyl group, so as to be bonded with an oxygen atom. When acid is generated upon exposure, the generated acid acts to break the bond between the acetal-type acid dissociable, dissolution inhibiting group and the oxygen atom with which the acetal-type, acid dissociable, dissolution inhibiting group is bonded.

Examples of acetal-type acid dissociable, dissolution inhibiting groups include groups represented by a general formula (p1) shown below.

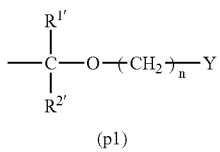

(p1)

(wherein, $R^{1\prime}$ and $R^{2\prime}$ each independently represents a hydrogen atom or a lower alkyl group; n represents an integer of 0 to 3; and Y represents a lower alkyl group or an aliphatic cyclic group.)

In the above formula, n is preferably an integer of 0 to 2, more preferably 0 or 1, and most preferably 0.

The lower alkyl group for $R^{1\prime}$ or $R^{2\prime}$ is the same as the lower alkyl groups described above in R. As the lower alkyl group of $R^{1\prime}$ or $R^{2\prime}$, a methyl group or an ethyl group is preferable, and a methyl group is most preferable.

In the present invention, at least one of $R^{1\prime}$ and $R^{2\prime}$ is preferably a hydrogen atom. That is, it is preferable that the acid dissociable, dissolution inhibiting group (p1) be a group represented by a general formula (p1-1) shown below.

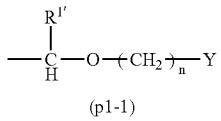

(p1-1)

(wherein, $R^{1\prime}$, n and Y are as defined above.)

The lower alkyl group of Y is the same as the lower alkyl group described above in R.

As the aliphatic cyclic group for Y, any of the aliphatic monocyclic or polycyclic groups which have been proposed for conventional ArF resists and the like can be used by being appropriately selected from those. For example, the same groups described above in the "aliphatic cyclic group" can be exemplified.

Further, as the acetal-type, acid dissociable, dissolution inhibiting group, groups represented by general formula (p2) shown below can also be exemplified.

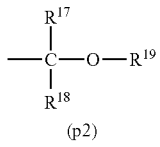

(p2)

(wherein $R^{17}$ and $R^{18}$ each independently represents a linear or branched alkyl group or a hydrogen atom; and $R^{19}$ represents a linear, branched or cyclic alkyl group. Alternately, $R^{17}$ and $R^{19}$ each independently represents a linear or branched alkylene group, wherein the terminal of $R^{17}$ may be bonded with the terminal of $R^{19}$ thereby forming a ring.)

The alkyl group for $R^{17}$ and $R^{18}$ preferably has 1 to 15 carbon atoms, and may be either linear or branched. As the alkyl group, an ethyl group or a methyl group is preferable, and a methyl group is most preferable.

It is particularly preferable that either one of $R^{17}$ and $R^{18}$ be a hydrogen atom, and the other be a methyl group.

$R^{19}$ represents a linear, branched or cyclic alkyl group which preferably has 1 to 15 carbon atoms, and may be any of linear, branched or cyclic. When $R^{19}$ represents a linear or branched alkyl group, it is preferably an alkyl group of 1 to 5 carbon atoms, more preferably an ethyl group or methyl group, and most preferably an ethyl group.

When $R^{19}$ represents a cyclic alkyl group, it preferably has 4 to 15 carbon atoms, more preferably 4 to 12 carbon atoms, and most preferably 5 to 10 carbon atoms. Specific examples of the cyclic alkyl group include groups in which one or more hydrogen atoms have been removed from a monocycloalkane or a polycycloalkane such as a bicycloalkane, tricycloalkane or tetracycloalkane, in which a fluorine atom or a fluorinated alkyl group may or may not be included as a substituent group. Specific examples thereof include groups in which one or more hydrogen atoms have been removed from a monocycloalkane such as cyclopentane and cyclohexane, and a polycycloalkane such as adamantane, norbornane, isobornane, tricyclodecane, and tetracyclododecane. Of these, a group in which one or more hydrogen atoms have been removed from adamantane is preferable.

In the general formula (p2), $R^{17}$ and $R^{19}$ may each independently represent a linear or branched alkylene group (preferably an alkylene group of 1 to 5 carbon atoms), and the terminal of $R^{19}$ may be bonded with the terminal of $R^{17}$. In such a case, a cyclic group is formed by $R^{17}$, $R^{19}$, the oxygen atom with which $R^{19}$ is bonded, and the carbon atom with which the oxygen atom and $R^{17}$ are bonded. Such a cyclic group is preferably a 4- to 7-membered ring, and more preferably a 4- to 6-membered ring. Specific examples of the cyclic group include a tetrahydropyranyl group and a tetrahydrofuranyl group.

As the structural unit (a1), it is preferable to use at least one member selected from the group consisting of structural units represented by a general formula (a1-0-1) shown below and structural units represented by a general formula formula (a1-0-2) shown below.

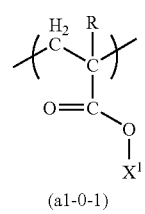

(a1-0-1)

(wherein, R represents a hydrogen atom, a lower alkyl group or a halogenated lower alkyl group; and $X^1$ represents an acid dissociable, dissolution inhibiting group.)

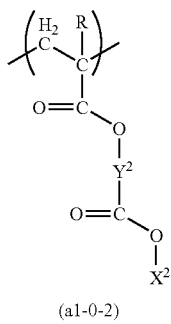

(a1-0-2)

(wherein, R represents a hydrogen atom, a lower alkyl group or a halogenated lower alkyl group; $X^2$ represents an acid dissociable, dissolution inhibiting group; and $Y^2$ represents an alkylene group or an aliphatic cyclic group.)

In the general formula (a1-0-1), the lower alkyl group or halogenated lower alkyl group of R are the same as the lower alkyl group or halogenated lower alkyl group which can be bonded with the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In the general formula (a1-0-2), R is the same as those described above.

$X^2$ is the same as $X^1$ described in the general formula (a1-0-1).

$Y^2$ is preferably an alkylen group of 1 to 10 carbon atoms or a bivalent aliphatic cyclic group. As the aliphatic cyclic group, the same as those described in "aliphatic cyclic group" can be used, with the exception that two or more hydrogen atoms are removed.

When $Y^2$ represents an alkylene group of 1 to 10 carbon atoms, it is more preferable that the number of carbon atoms be 1 to 6, still more preferably 1 to 4, and most preferably 1 to 3.

When $Y^2$ represents a divalent aliphatic cyclic group, it is particularly preferable that the divalent aliphatic cyclic group be a group in which two or more hydrogen atoms have been removed from a cyclopentane, a cyclohexane, a norbornane, an isobornane, an adamantane, a tricyclodecane or a tetracyclododecane.

Specific examples of the structural unit (a1) include structural units represented by the general formulae (a1-1) to (a1-4) shown below.

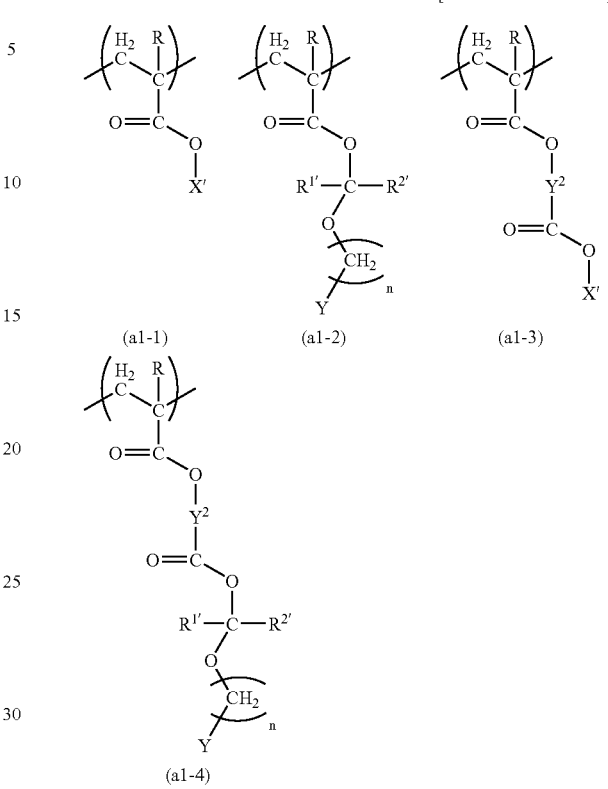

(wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; $Y^2$ represents an alkylene group or an aliphatic cyclic group; R is as defined above; and $R^{1\prime}$ and $R^{2\prime}$ each independently represents a hydrogen atom or a lower alkyl group of 1 to 5 carbon atoms.)

In the formula, X' is the same as a tertiary alkyl ester-type acid dissociable, dissolution inhibiting group described in $X^1$.

$R^{1\prime}$, $R^{2\prime}$, n and Y are the same as $R^{1\prime}$, $R^{2\prime}$, n and Y in the general formula (p1) shown in "acetal-type acid dissociable, dissolution inhibiting group".

$Y^2$ is the same as $Y^2$ in the general formula (a1-0-2).

Specific examples of structural units represented by general formulae (a1-1) and (a1-4) shown above include the following.

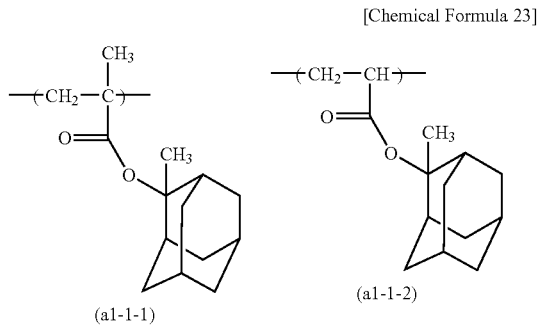

-continued
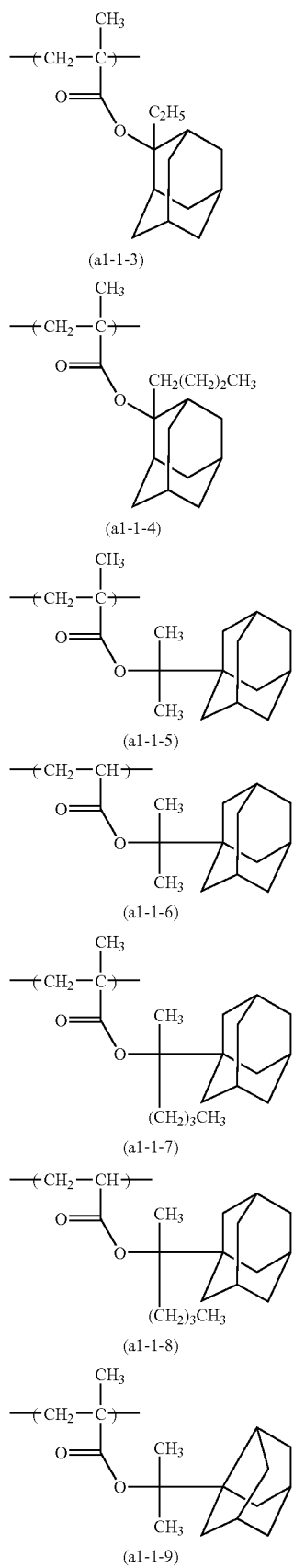
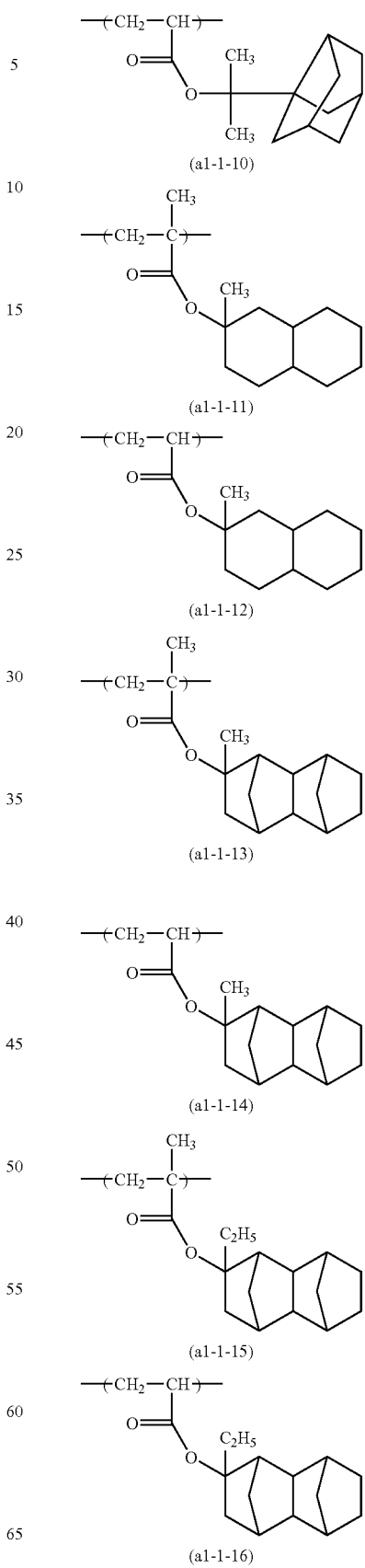

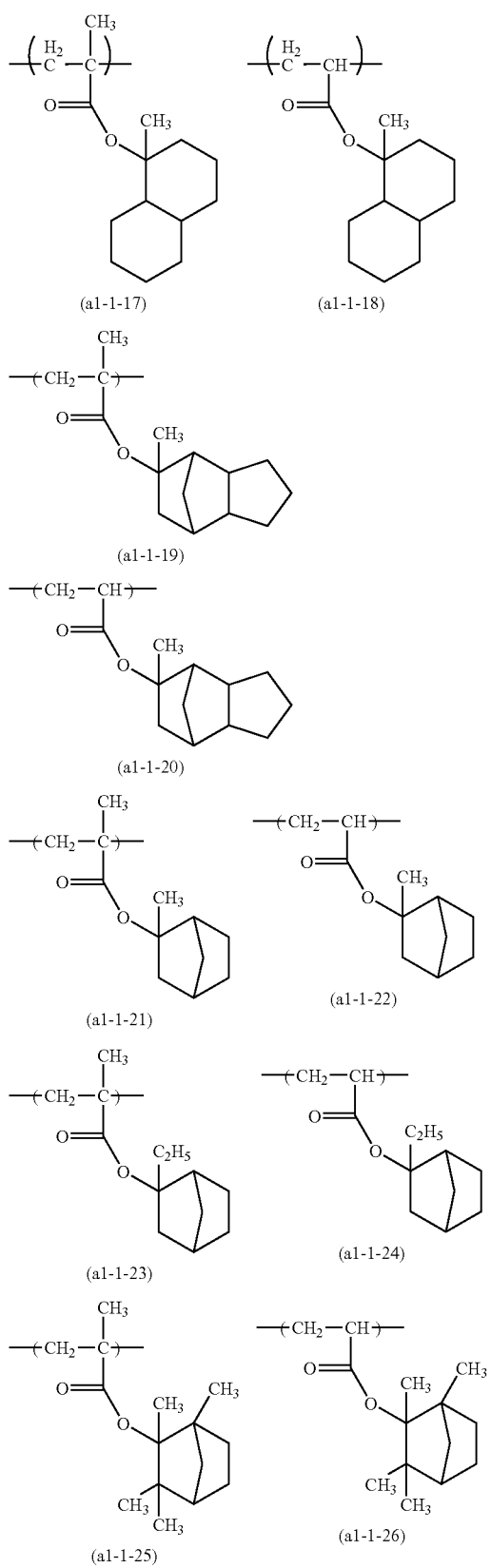
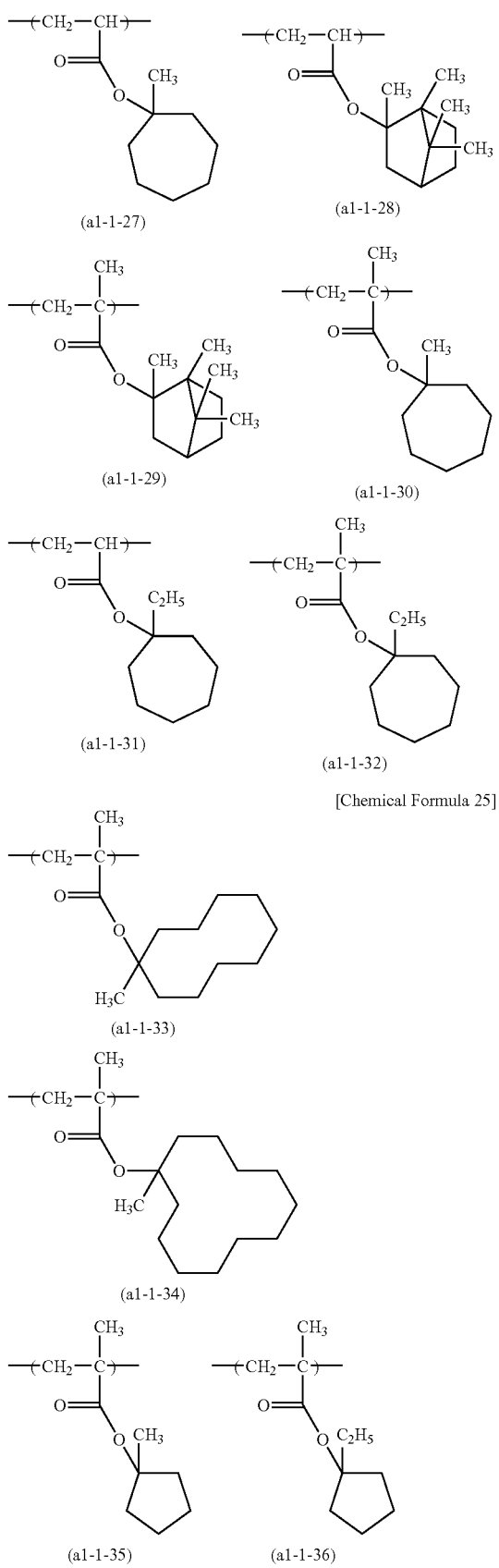

-continued
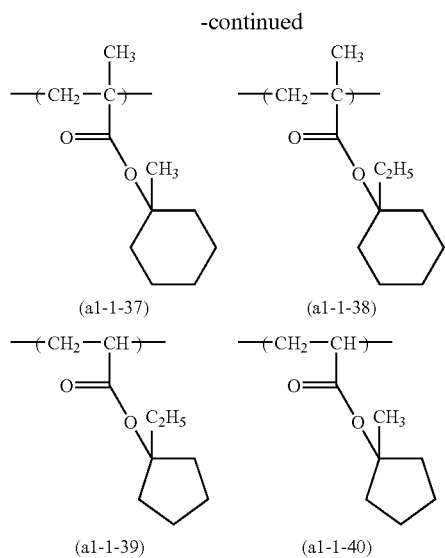
(a1-1-37)　(a1-1-38)
(a1-1-39)　(a1-1-40)
(a1-1-41)　(a1-1-42)
(a1-1-43)　(a1-1-44)
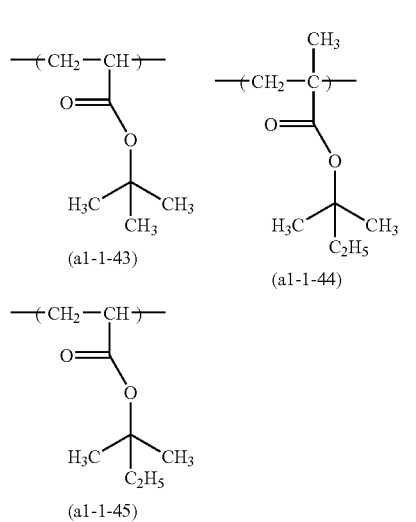
(a1-1-45)
[Chemical Formula 26]
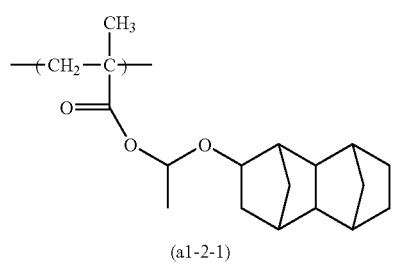
(a1-2-1)
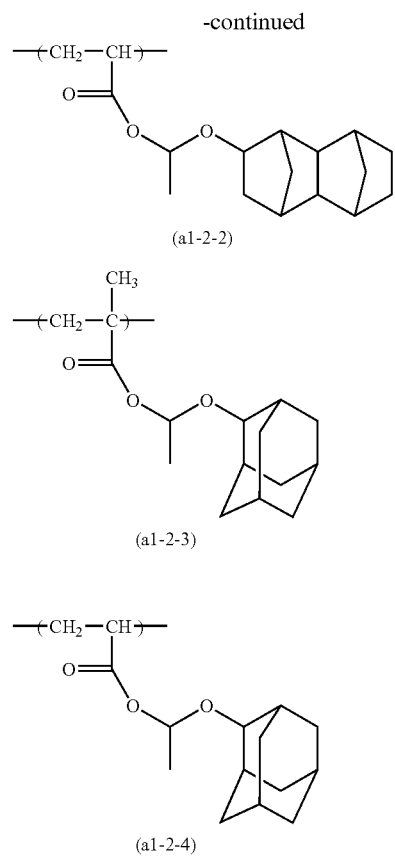
(a1-2-2)
(a1-2-3)
(a1-2-4)
(a1-2-5)
(a1-2-6)
[Chemical Formula 27]
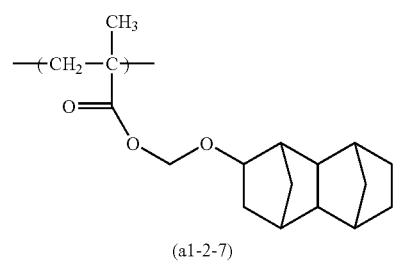
(a1-2-7)

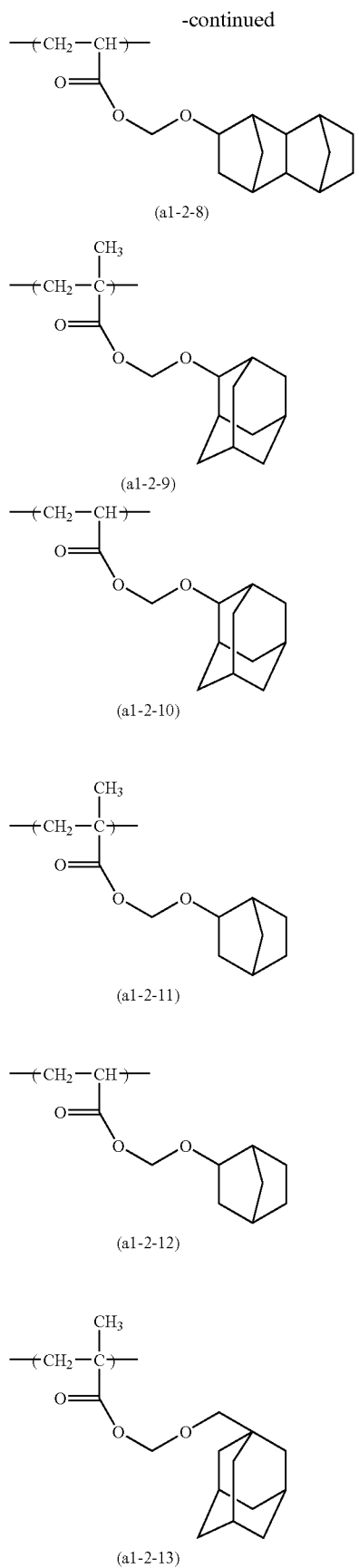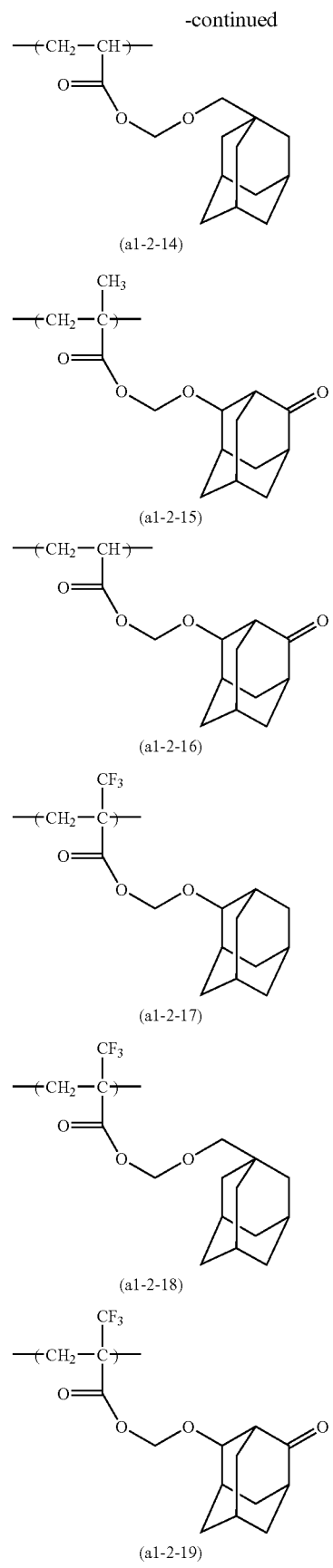

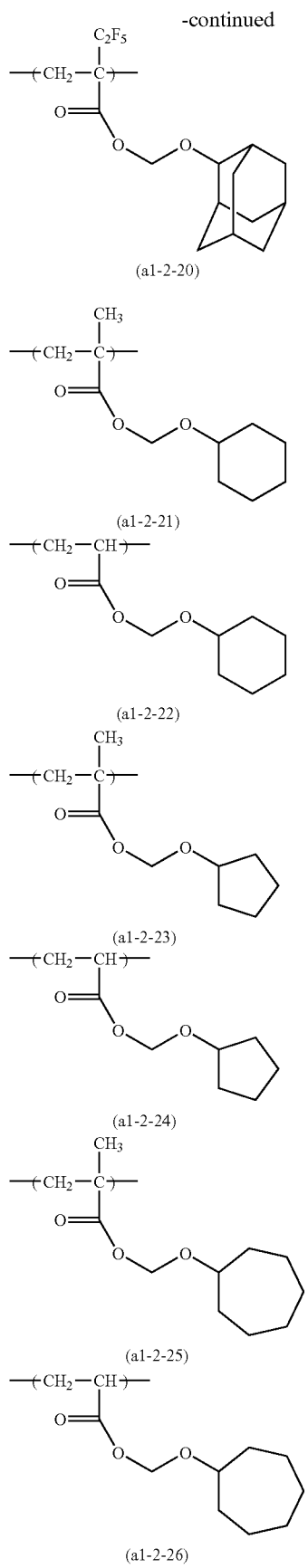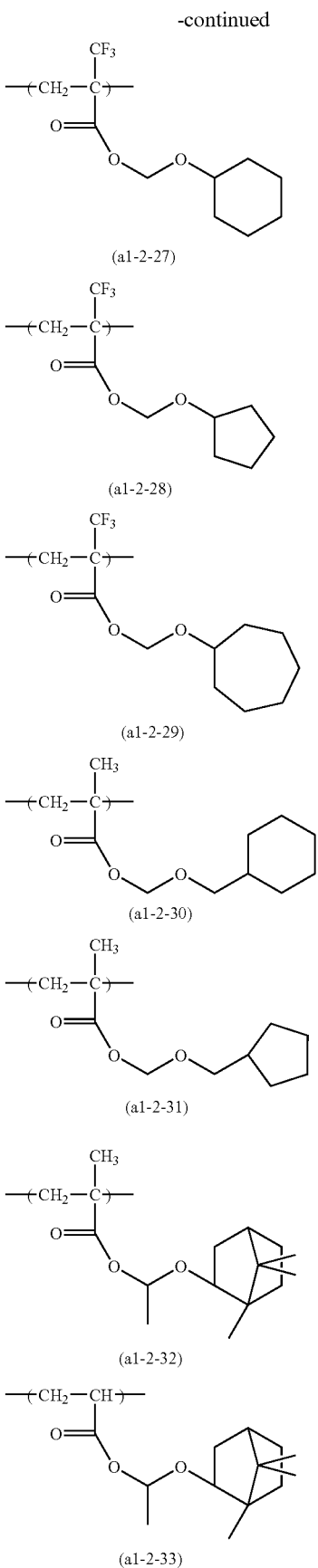

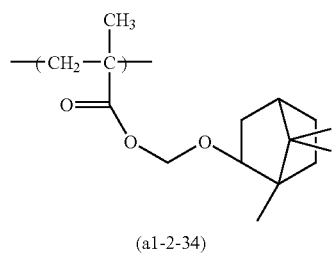
(a1-2-34)
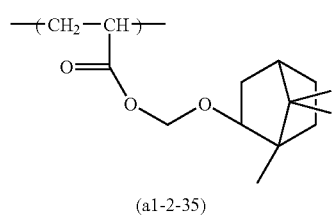
(a1-2-35)
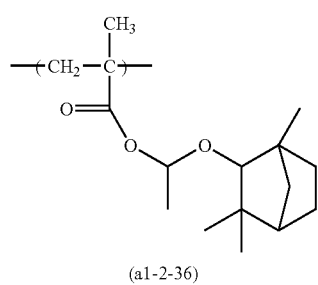
(a1-2-36)
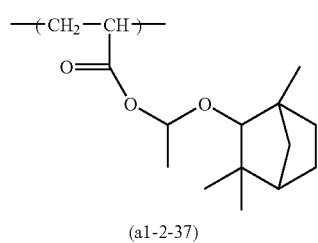
(a1-2-37)
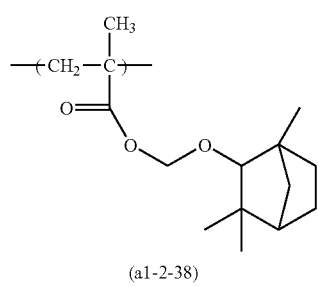
(a1-2-38)
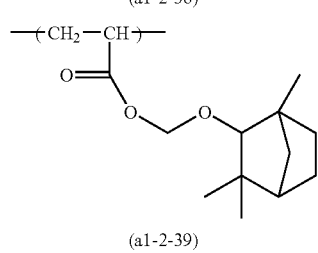
(a1-2-39)
[Chemical Formula 30]
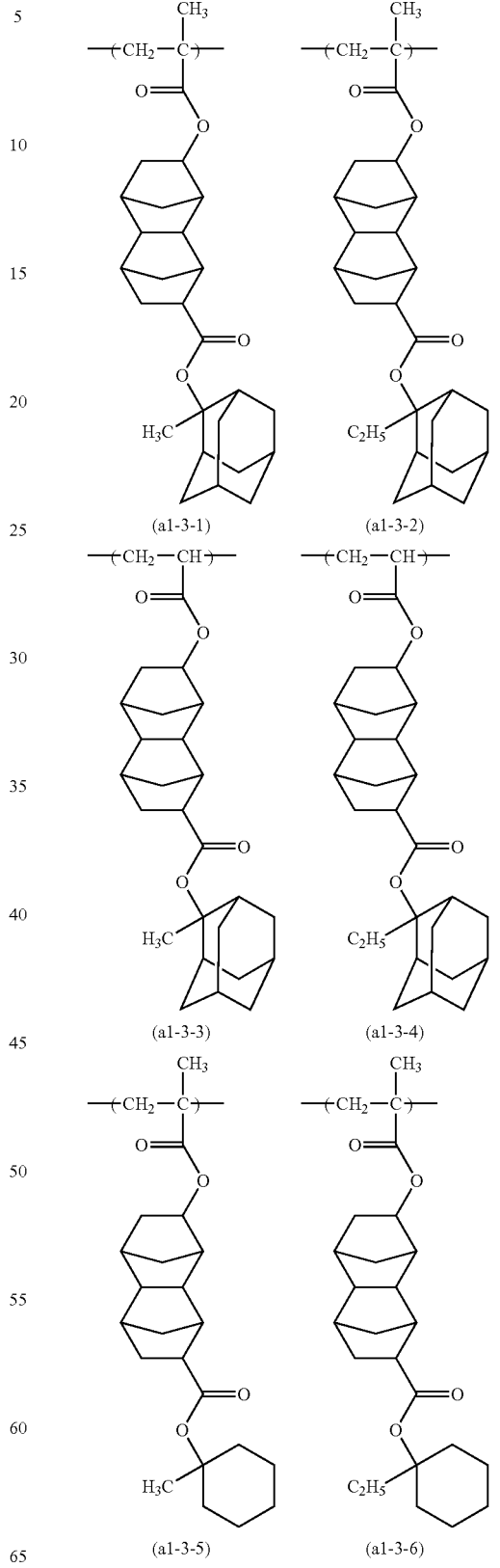
(a1-3-1)   (a1-3-2)
(a1-3-3)   (a1-3-4)
(a1-3-5)   (a1-3-6)

-continued
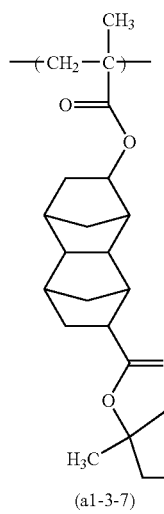
(a1-3-7)
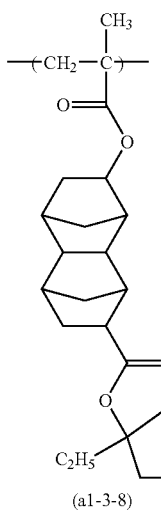
(a1-3-8)
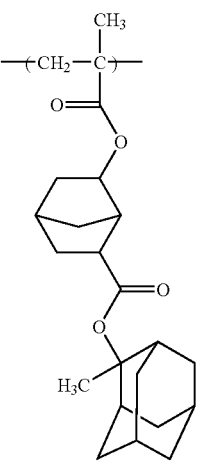
(a1-3-13)
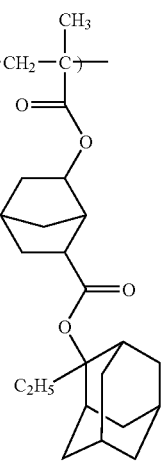
(a1-3-14)
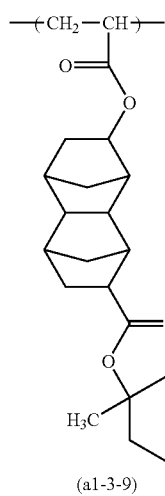
(a1-3-9)
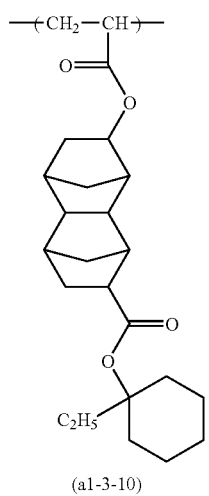
(a1-3-10)
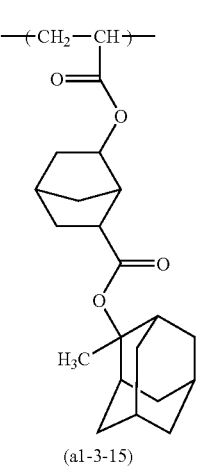
(a1-3-15)
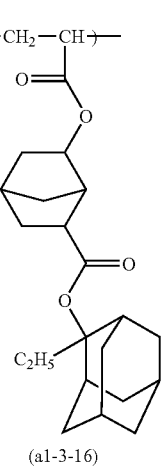
(a1-3-16)
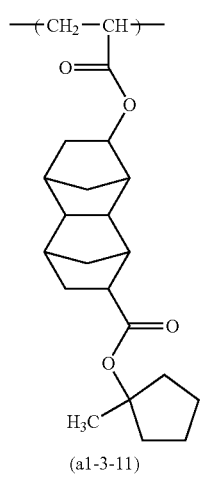
(a1-3-11)
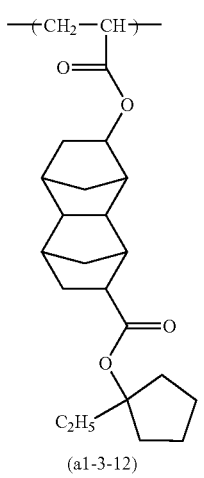
(a1-3-12)
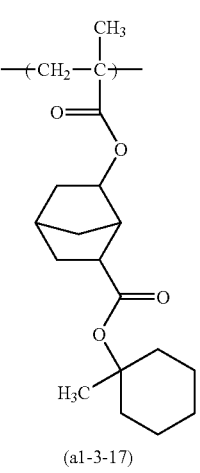
(a1-3-17)
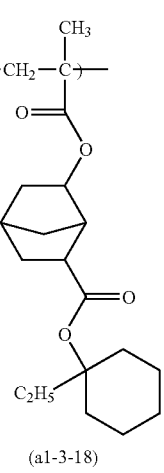
(a1-3-18)

-continued
[Chemical Formula 31]
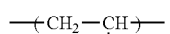
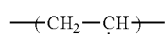
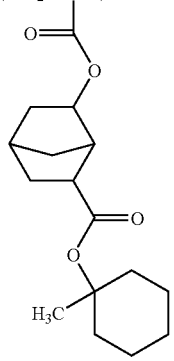
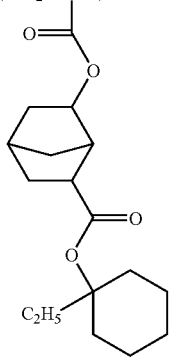
(a1-3-19)   (a1-3-20)
-continued
[Chemical Formula 32]
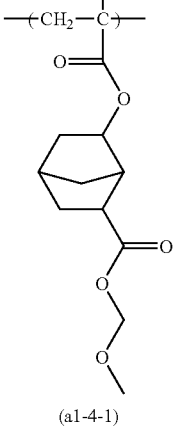
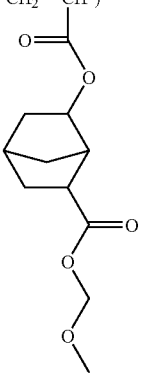
(a1-4-1)   (a1-4-2)
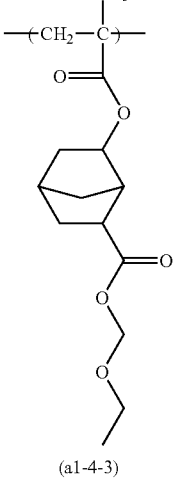
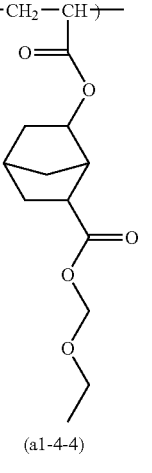
(a1-4-3)   (a1-4-4)
(a1-3-21)   (a1-3-22)
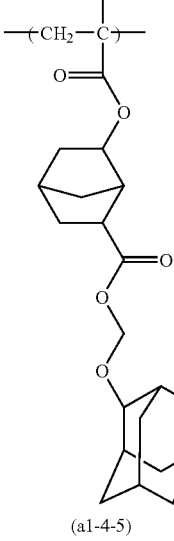
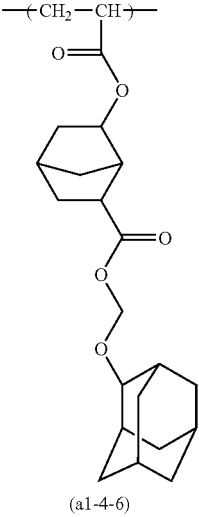
(a1-3-23)   (a1-3-24)
(a1-4-5)   (a1-4-6)

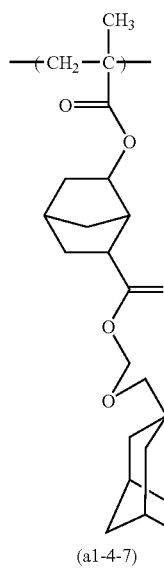 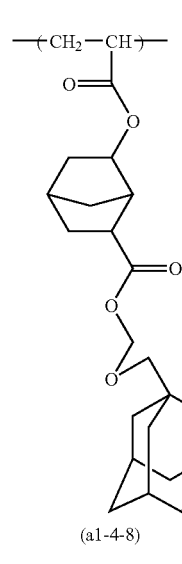 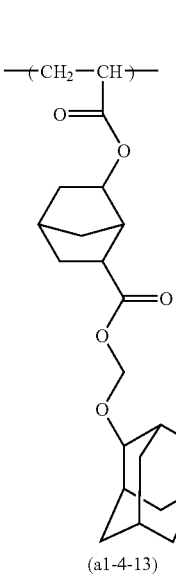 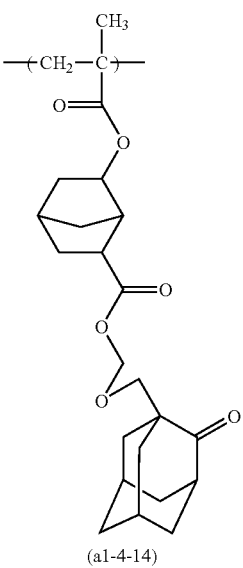
(a1-4-7)   (a1-4-8)   (a1-4-13)   (a1-4-14)
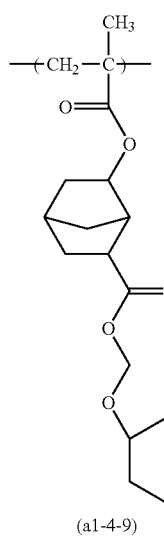 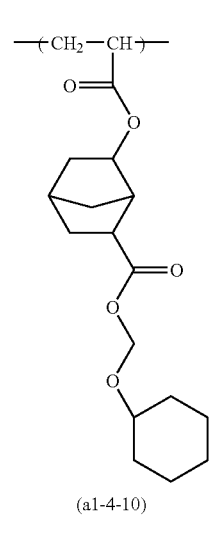
(a1-4-9)   (a1-4-10)
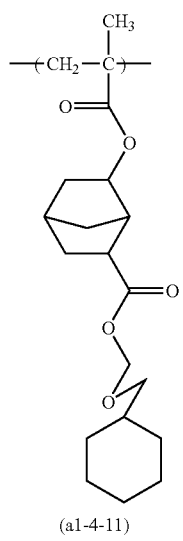 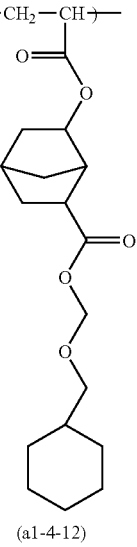 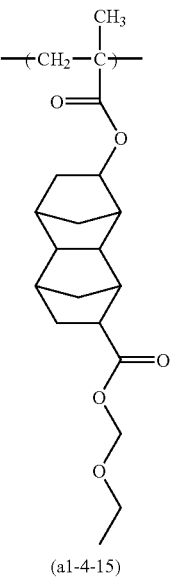 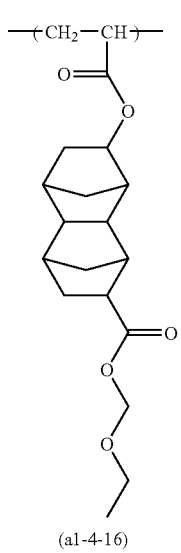
(a1-4-11)   (a1-4-12)   (a1-4-15)   (a1-4-16)

[Chemical Formula 33]
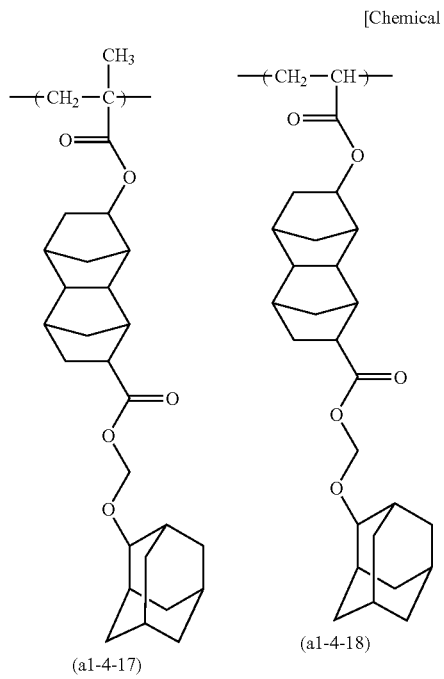
(a1-4-17)  (a1-4-18)
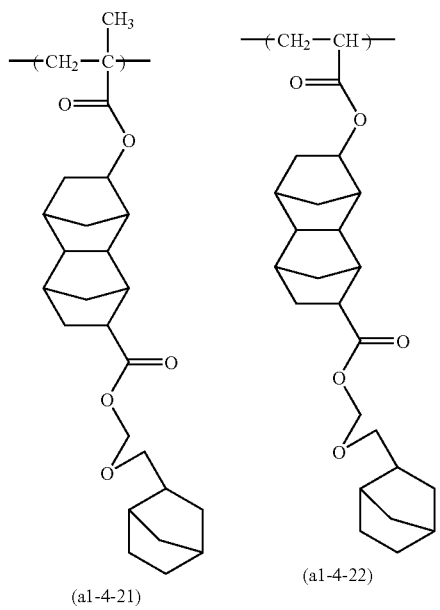
(a1-4-21)  (a1-4-22)
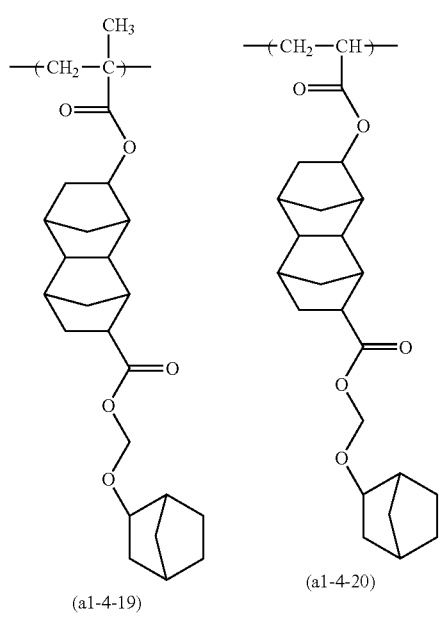
(a1-4-19)  (a1-4-20)
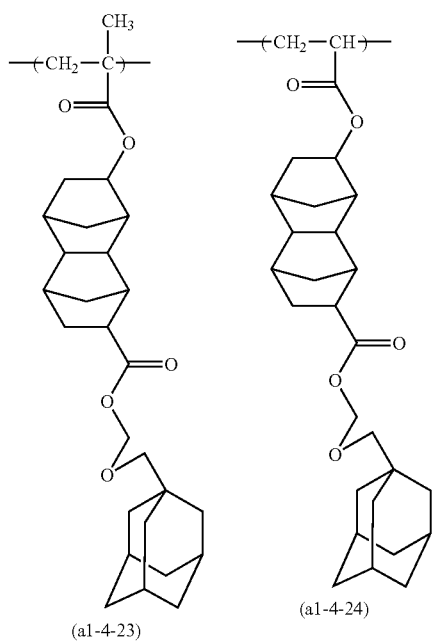
(a1-4-23)  (a1-4-24)

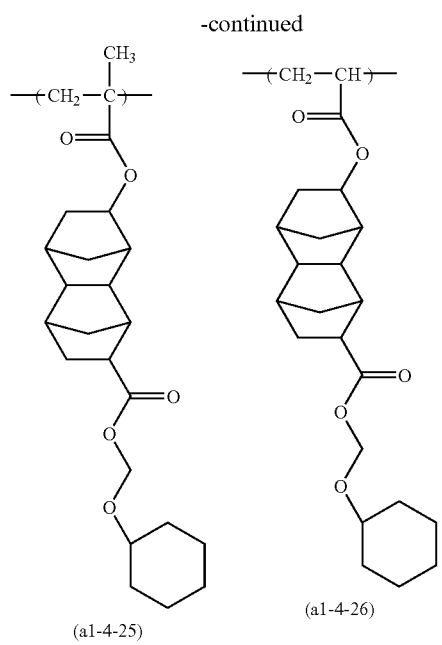
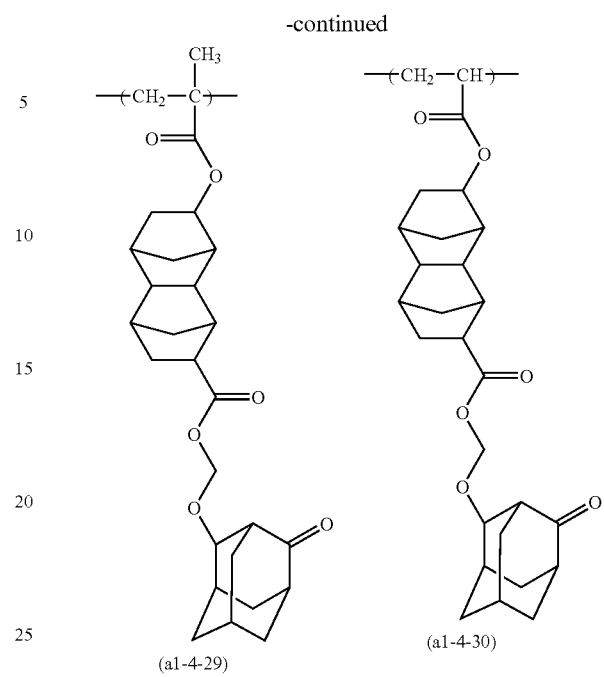
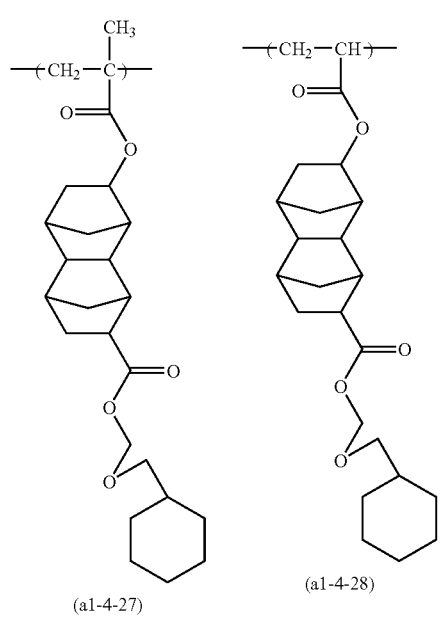
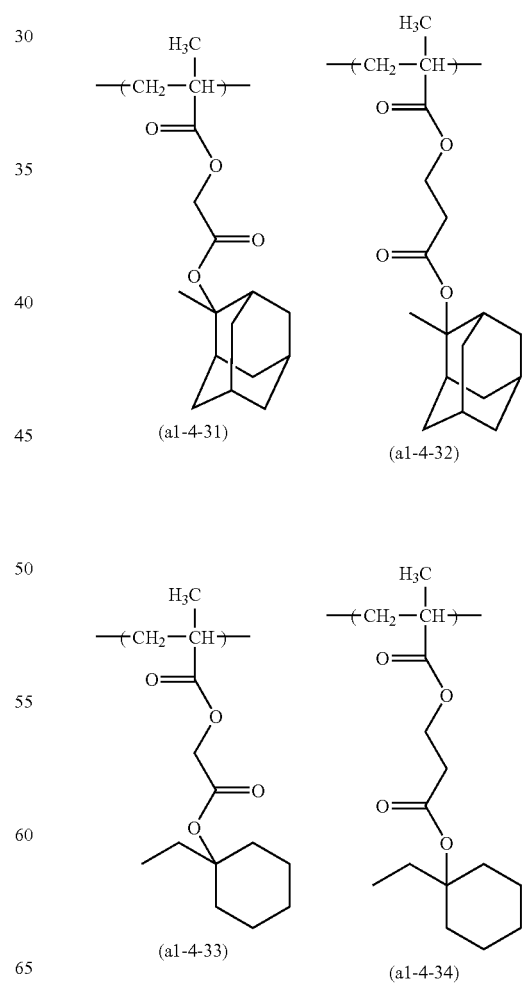

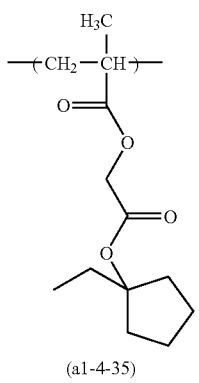
(a1-4-35)

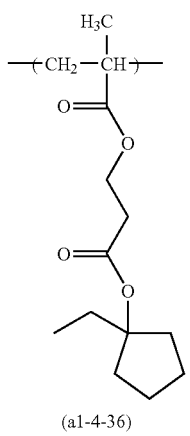
(a1-4-36)

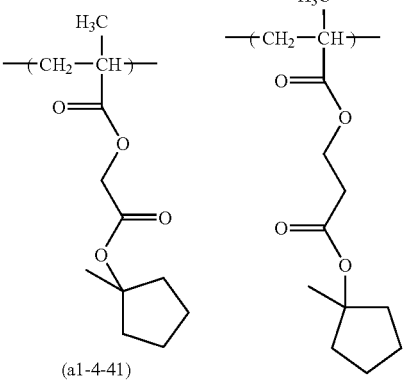
(a1-4-41)

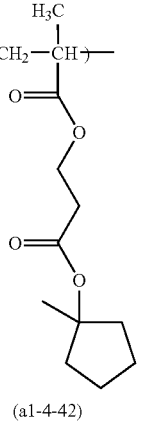
(a1-4-42)

Of these, a structural unit represented by the general formula (a1-1) is preferable, and it is more preferable to use at least one kind selected from the group consisting of the general formula (a1-1-1) to (a1-1-6), and (a1-1-35) to (a1-1-41).

Further, as the structural unit (a1), structural units represented by a general formula (a1-1-01) shown below which includes the structural units represented by formulae (a1-1-1) to (a1-1-4), and structural units represented by a general formula (a1-1-02) shown below which includes the structural units represented by formulae (a1-1-35) to (a1-1-41) are also preferable.

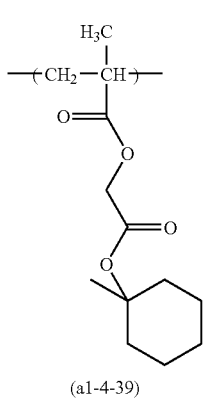
(a1-4-37)

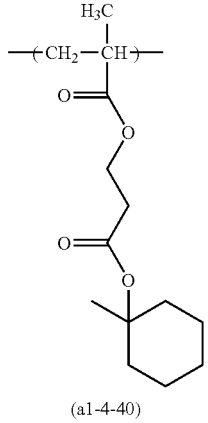
(a1-4-38)

[Chemical Formula 34]

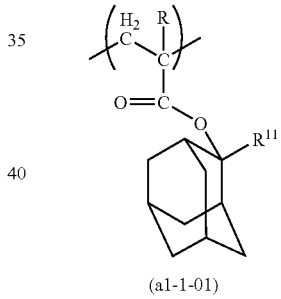
(a1-1-01)

(in the formula, R represents a hydrogen atom, a lower alkyl group or a halogenated lower alkyl group; and $R^{11}$ represents a lower alkyl group.)

[Chemical Formula 35]

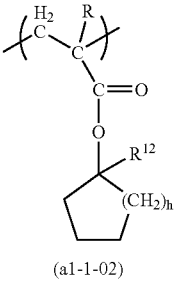
(a1-1-02)

(in the formula, R represents a hydrogen atom, a lower alkyl group or a halogenated lower alkyl group; and $R^{12}$ represents a lower alkyl group. h represents an integer of 1 to 3.)

In the general formula (a1-1-01), R is as defined above.

The lower alkyl group for $R^{11}$ is the same as the lower alkyl group described above in R, and is preferably a methyl group or an ethyl group.

In the general formula (a1-1-02), R is as defined above. The lower alkyl group for $R^{12}$ is the same as the lower alkyl group described above in R. $R^{12}$ is preferably a methyl group or an ethyl group, and most preferably an ethyl group. h is preferably 1 or 2, and most preferably 2.

The structural unit (a1) can be used alone, or in combinations of two or more different units.

In the component (A1), the amount of the structural unit (a1) is preferably 10 to 80 mol %, more preferably 20 to 70 mol %, and still more preferably 25 to 50 mol %, based on the combined total of all structural units constituting the component (A1). When this proportion is not less than the lower limit in the above range, then a pattern can be easily formed using a positive resist composition which includes the component (A1), whereas when the proportion is not more than the upper limit in the above range, good quantitative balance with the other components can be attained.

Structural Unit (a2)

In the present invention, the component (A1) preferably has a structural unit (a2) derived from an acrylate ester having a lactone-containing cyclic group, in addition to the structural unit (a1).

Here, the term "lactone-containing cyclic group" represents a cyclic group containing a single ring (lactone ring) which has a "—O—C(O)—" structure. This lactone ring is counted as the first ring, and groups that contain only the lactone ring are referred to as monocyclic groups, whereas groups that also contain other ring structures are described as polycyclic groups regardless of the structure of the other rings. In the case of using the component (A1) to form a resist film, the lactone-containing cyclic group of the structural unit (a2) is effective at improving the adhesion between the resist film and a substrate, and improving compatibility with the developing solution.

The structural unit (a2) can be used arbitrarily without any particular restriction.

Specific examples of the lactone-containing monocyclic group include a group wherein one hydrogen atom is eliminated from γ-butyrolactone. Furthermore, specific examples of the lactone-containing polycyclic group include a group wherein one hydrogen atom is eliminated from a bicycloalkane, a tricycloalkane, or a tetracycloalkane which contains a lactone ring.

Specific examples of the structural unit (a2) include structural units represented by the general formulae (a2-1) to (a2-5) shown below.

[Chemical Formula 36]

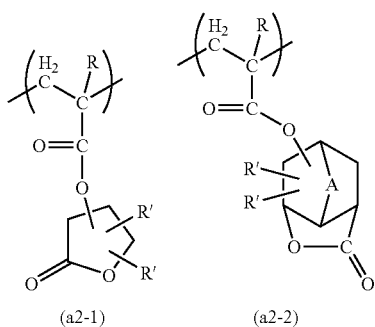

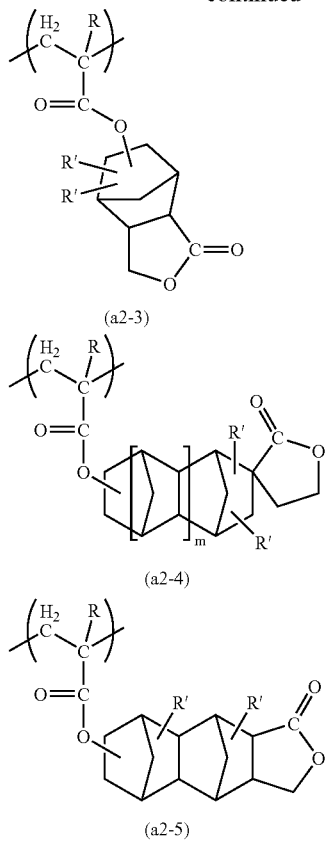

(wherein, R represents a hydrogen atom, a lower alkyl group or a halogenated lower alkyl group; R' represents a hydrogen atom, a lower alkyl group or an alkoxy group of 1 to 5 carbon atoms; m represents an integer of 0 or 1; and A represents an alkylene group of 1 to 5 carbon atoms or an oxygen atom.)

R in the general formula (a2-1) to (a2-5) is the same as R described above in the structural unit (a1).

The lower alkyl group for R' is the same as the lower alkyl group for R in the structural unit (a1).

Specific examples of alkylene groups of 1 to 5 carbon atoms for A include a methylene group, an ethylene group, an n-propylene group and an isopropylene group. In the general formula (a2-1) to (a2-5), R' is preferably a hydrogen atom in terms of industrial availability.

Specific examples of the structural units represented by the general formulae (a2-1) to (a2-5) include the following.

[Chemical Formula 37]

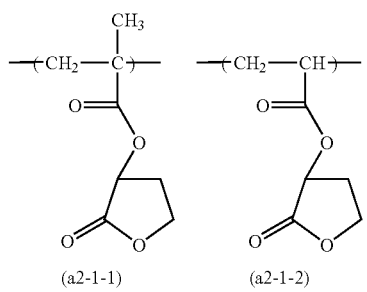

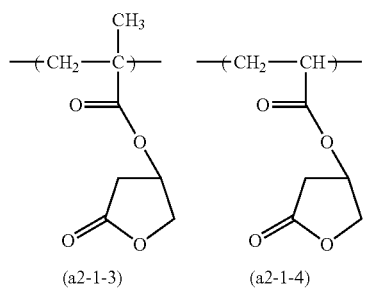
(a2-1-3)  (a2-1-4)
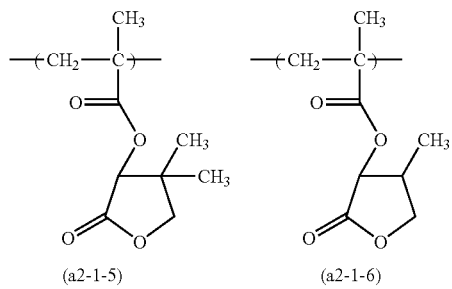
(a2-1-5)  (a2-1-6)
[Chemical Formula 38]
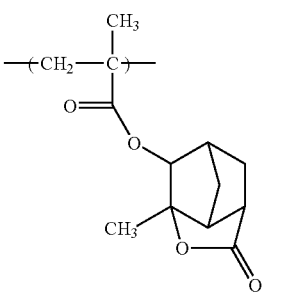
(a2-2-1)
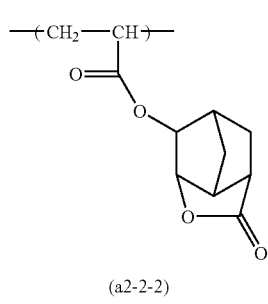
(a2-2-2)
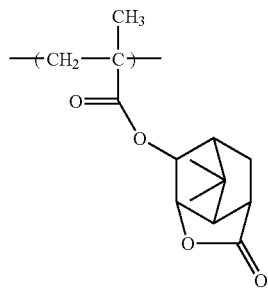
(a2-2-3)
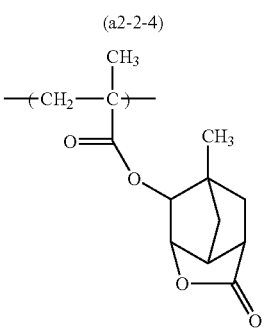
(a2-2-4)
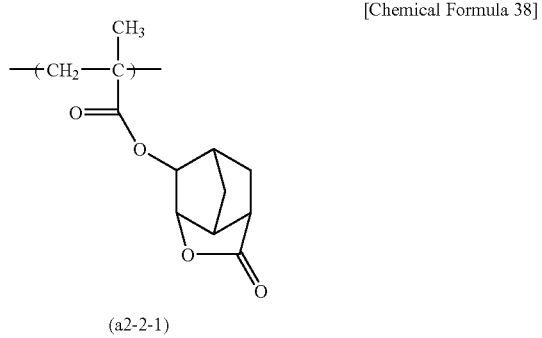
(a2-2-5)
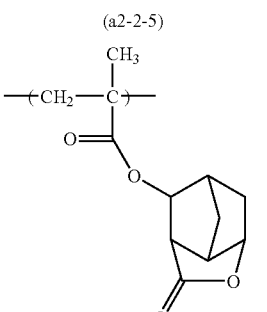
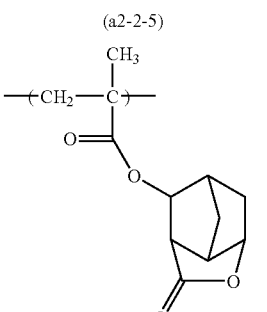
(a2-2-6)  (a2-2-7)
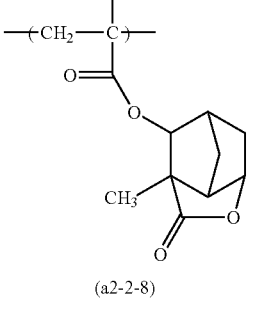
(a2-2-8)
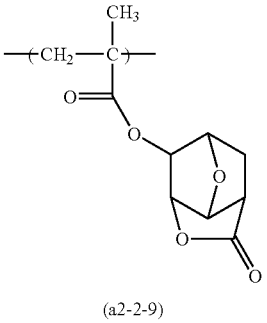
(a2-2-9)

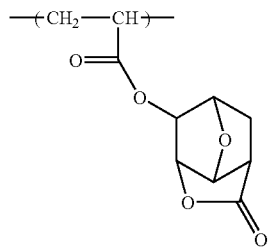
(a2-2-10)
[Chemical Formula 39]
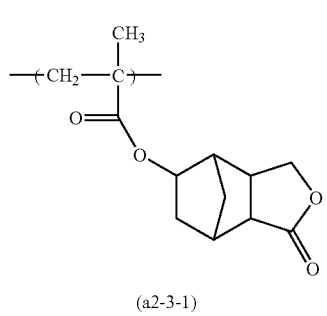
(a2-3-1)
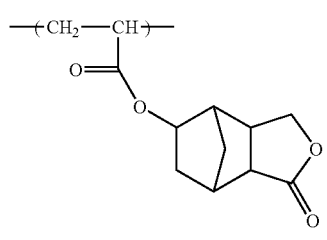
(a2-3-2)
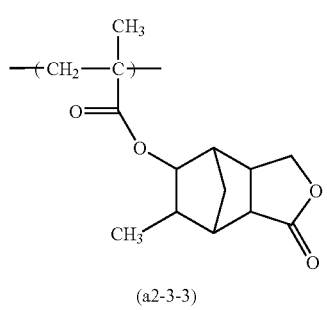
(a2-3-3)
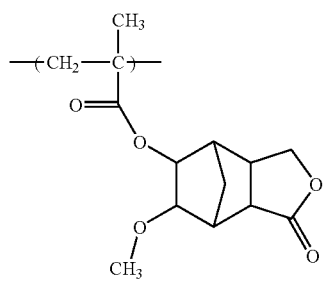
(a2-3-4)
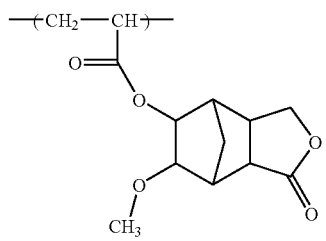
(a2-3-5)
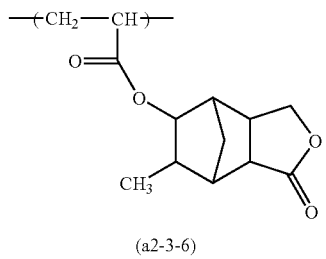
(a2-3-6)
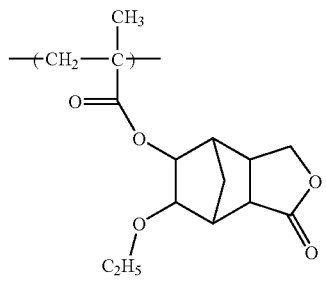
(a2-3-7)
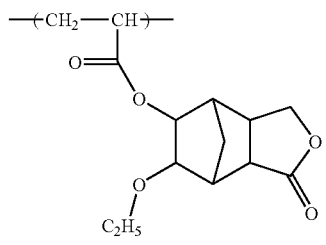
(a2-3-8)
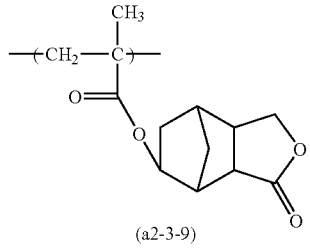
(a2-3-9)
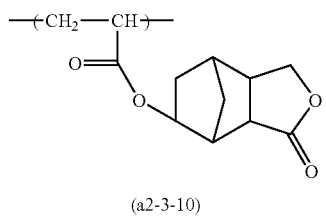
(a2-3-10)

[Chemical Formula 40]
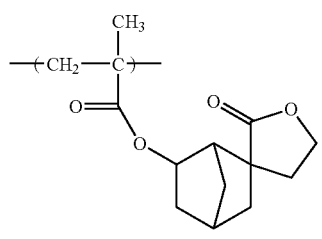
(a2-4-1)
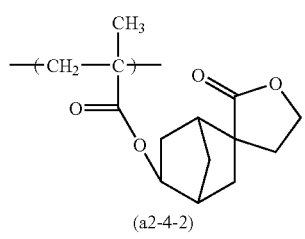
(a2-4-2)
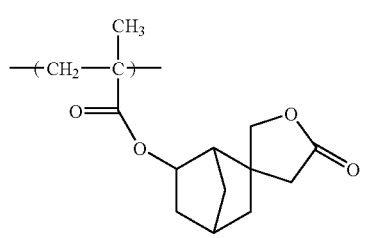
(a2-4-3)
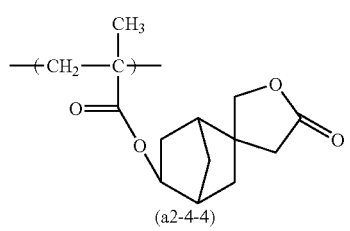
(a2-4-4)
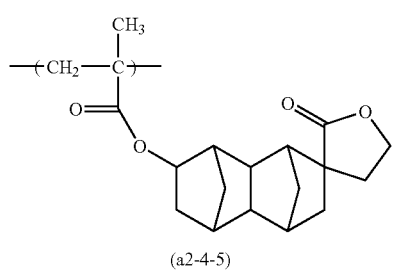
(a2-4-5)
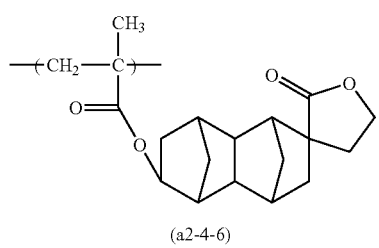
(a2-4-6)
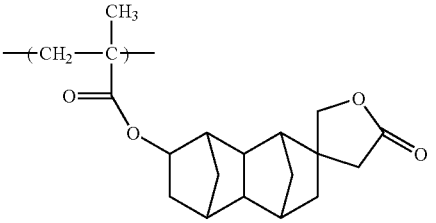
(a2-4-7)
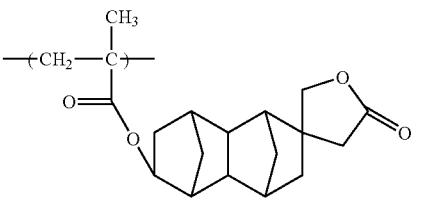
(a2-4-8)
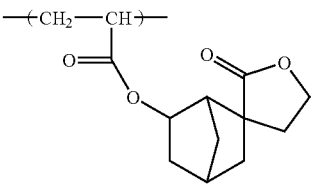
(a2-4-9)
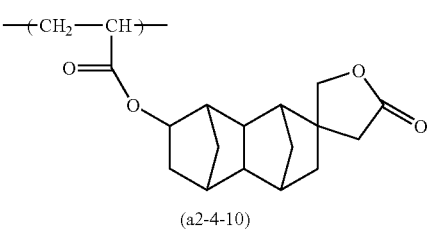
(a2-4-10)
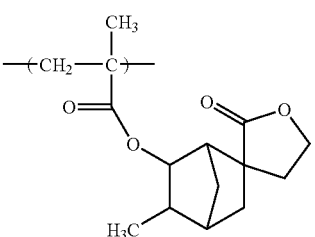
(a2-4-11)
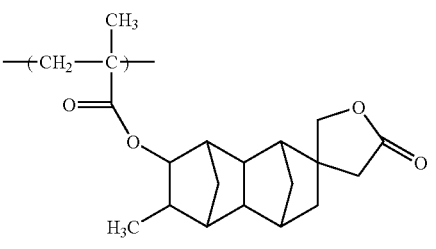
(a2-4-12)

-continued

[Chemical Formula 41]

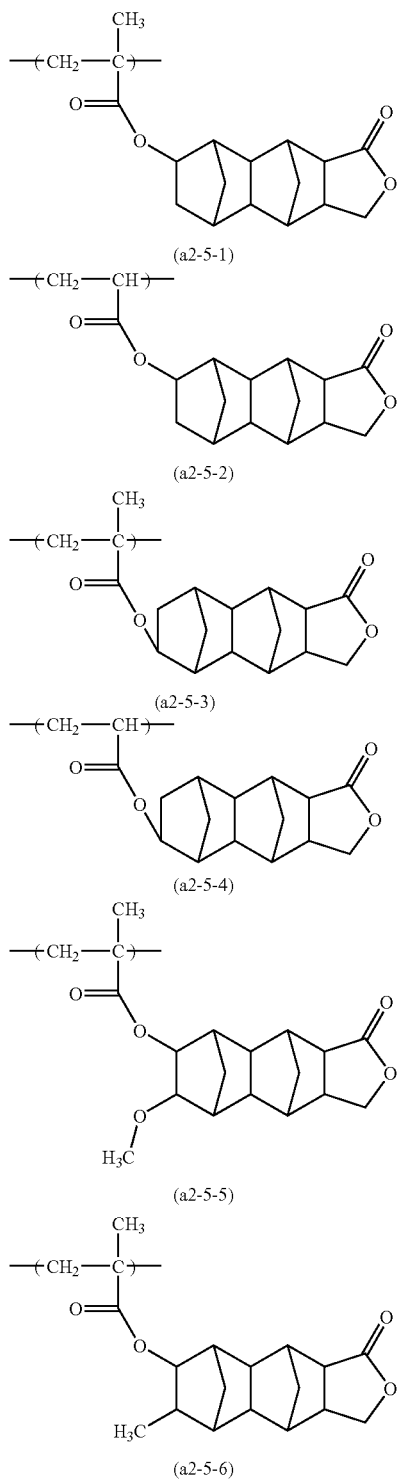

(a2-5-1)

(a2-5-2)

(a2-5-3)

(a2-5-4)

(a2-5-5)

(a2-5-6)

The structural unit (a2) is preferably at least one kind selected from the group consisting of the structural units represented by the general formulae (a2-1) to (a2-5), and more preferably at least one kind selected from the group consisting of the structural units represented by the general formula (a2-1) to (a2-3). Of these, at least one kind selected from the group consisting of the structural units represented by (a2-1-1), (a2-2-1), (a2-2-2), (a2-3-1), (a2-3-2), (a2-3-9) and (a2-3-10) is particularly preferable.

The structural unit (a2) can be used alone, or in combinations of two or more different units.

In the component (A1), the amount of the structural unit (a2) is preferably 5 to 60 mol %, more preferably 10 to 50 mol %, and still more preferably 20 to 50 mol %, based on the combined total of all structural units constituting the component (A1). When this proportion is not less than the lower limit in the above range, then the effect by containing the structural unit (a2) can be sufficiently obtained. When the proportion is not more than the upper limit in the above range, good quantitative balance with the other components can be attained.

Structural Unit (a3)

In the present invention, the component (A1) preferably has a structural unit (a3) derived from an acrylate ester having a polar group-containing aliphatic hydrocarbon group, in addition to the structural unit (a1) or the structural units (a1) and (a2). By including the structural unit (a3), the hydrophilicity of the component (A1) is improved, and hence, the compatibility of the component (A1) with the developing solution is improved. As a result, the solubility of the exposed portions in an alkali developing solution improves, which contributes to favorable improvements in the resolution.

Examples of the polar group include a hydroxyl group, a cyano group, a carboxyl group, a hydroxyalkyl group in which a part of the hydrogen atoms in an alkyl group is substituted with fluorine atoms. Of these, a hydroxyl group is particularly preferable.

Examples of the aliphatic hydrocarbon group include a linear or branched hydrocarbon group of 1 to 10 carbon atoms (preferably an alkylene group), and a polycyclic aliphatic hydrocarbon group (polycyclic group). The polycyclic group can be appropriately selected from the multitude of structural units proposed as resins in resist compositions for ArF excimer lasers and the like. The number of carbon atoms in the polycyclic group is preferably from 7 to 30.

Of these, a structural unit derived from an acrylate ester having the polycyclic aliphatic group which contains a hydroxyl group, a cyano group, a carboxyl group, or a hydroxyalkyl group in which a part of the hydrogen atoms within an alkyl group has been substituted with fluorine atoms (fluorinated alkyl group) is more preferable. Examples of the polycyclic group include groups in which two or more hydrogen atoms have been removed from a bicycloalkane, a tricycloalkane, a tetracycloalkane, or the like. Specific examples include a group in which two or more hydrogen atoms have been removed from a polycycloalkane such as an adamantane, a norbornane, an isobornane, a tricyclodecane, or a tetracyclododecane. Of these polycyclic groups, a group in which two or more hydrogen atoms have been removed from an adamantane, a norbornane, or a tetracyclododecane is industrially preferable.

As the structural unit (a3), for example, a structural unit derived from a hydroxyethyl ester of acrylic acid is preferable, when the hydrocarbon group within the polar group-containing aliphatic hydrocarbon group is a linear or branched hydrocarbon group of 1 to 10 carbon atoms. On the other hand, a structural unit represented by a general formula (a3-1), (a3-2), or (a3-3) is preferable, when the hydrocarbon group is a polycyclic group.

[Chemical Formula 42]

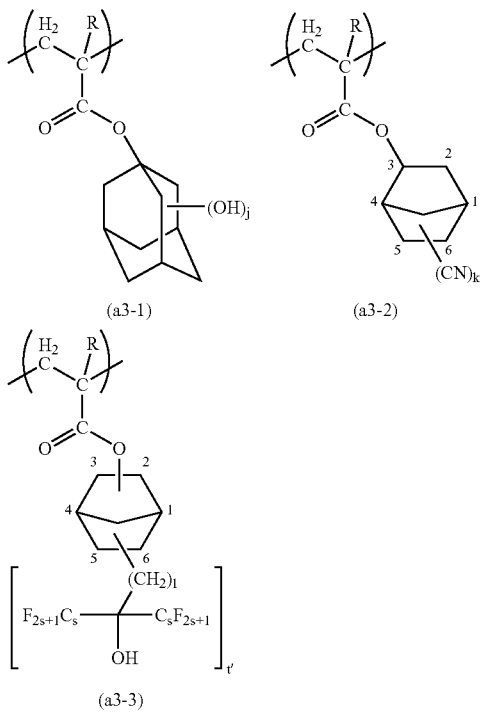

(a3-1)  (a3-2)

(a3-3)

(wherein, R is as defined above; j represents an integer of 1 to 3; k represents an integer of 1 to 3; t' represents an integer of 1 to 3; l represents an integer of 1 to 5; and s represents an integer of 1 to 3.)

In the general formula (a3-1), j is preferably 1 or 2, and more preferably 1. In the case that j is 2, a structural unit in which a hydroxyl group is bonded with the 3-position and 5-position of the adamantyl group is preferable. In the case that j is 1, a structural unit in which a hydroxyl group is bonded with the 3-position of the adamantyl group is preferable. Of these, it is preferable that j be 1, and the hydroxyl group be bonded with the 3-position of the adamantyl group.

In the general formula (a3-2), k is preferably 1. In the general formula (a3-2), a structural unit in which a cyano group is bonded with the 5-position or 6-position of the norbornyl group is preferable.

In the general formula (a3-3), t' is preferably 1. l is preferably 1. s is preferably 1. Further, in the general formula (a3-3), it is preferable that a 2-norbornyl group or 3-norbornyl group be bonded at the terminal of the carboxy group of the acrylic acid. It is preferable that a fluorinated alkyl alcohol be bonded with the 5-position or 6-position of the norbornyl group.

The structural unit (a3) can be used alone, or in combinations of two or more different units.

In the component (A1), the amount of the structural unit (a3) is preferably 5 to 50 mol %, more preferably 5 to 40 mol %, and still more preferably 5 to 25 mol %, based on the combined total of all structural units constituting the component (A1). When this proportion is not less than the lower limit in the above range, then the effect by containing the structural unit (a3) can be sufficiently obtained, whereas when the proportion is not more than the upper limit in the above range, good quantitative balance with the other components can be attained.

Structural Unit (a4)

The component (A1) may also have a structural unit (a4) which is different from the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

The structural unit (a4) is preferably, for example, a structural unit derived from an acrylate ester containing a non-acid-dissociable aliphatic polycyclic group. Examples of the polycyclic group include the same groups described above in the structural unit (a1), and any of the multitude of conventional polycyclic groups used within the resin component of resist compositions for ArF excimer lasers or KrF excimer lasers (and preferably for ArF excimer lasers) can be used.

In particular, at least one group selected from amongst a tricyclodecanyl group, an adamantyl group, a tetracyclododecanyl group, an isobornyl group, and a norbornyl group is preferable in terms of industrial availability and the like. These polycyclic groups may contain a linear or branched alkyl group of 1 to 5 carbon atoms as a substituent group.

Specific examples of the structural unit (a4) include a structural unit represented by general formulae (a4-1) to (a4-5) shown below.

[Chemical Formula 43]

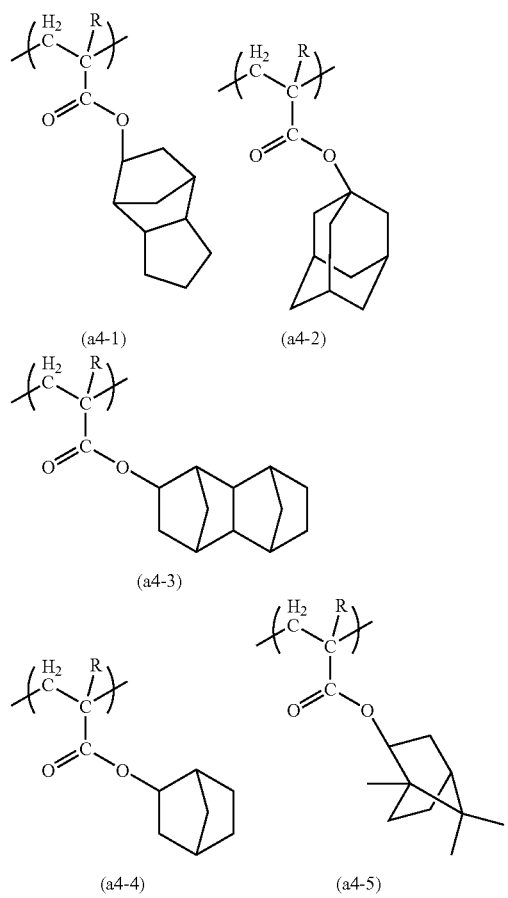

(a4-1)  (a4-2)

(a4-3)

(a4-4)  (a4-5)

(In the formula, R is as defined above.)

When the structural unit (a4) is included in the component (A1), the amount of the structural unit (a4) is preferably within the range from 1 to 30 mol %, and more preferably from 10 to 20 mol %, based on the combined total of all the structural units that constitute the component (A1).

In the present invention, the component (A1) preferably includes a copolymer which contains the structural units (a1), (a2) and (a3). Examples of the copolymer include a copolymer formed from the structural units (a1), (a2) and (a3); and a copolymer formed from the structural units (a1), (a2), (a3) and (a4).

As the copolymer, for example, those which contain three kinds of the strucutural units represented by a general formula (A-11) are preferable.

[Chemical Formula 44]

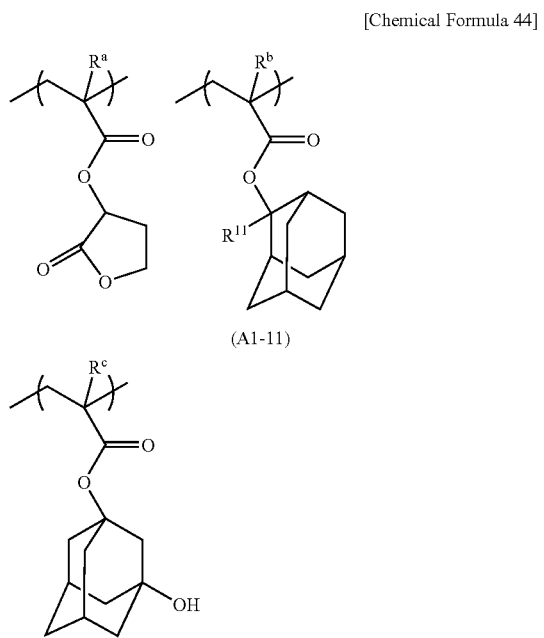

(A1-11)

(wherein, Ra, Rb and Rc are each independently the same as R described above; and $R^{11}$ represents a lower alkyl group.)

In the general formula (A1-11), a lower alkyl group for $R^{11}$ is the same as $R^{11}$ in the general formula (a1-1-01), and a methyl group or an ethyl group is preferable.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as $HS-CH_2-CH_2-CH_2-C(CF_3)_2-OH$, a $-C(CF_3)_2-OH$ group can be introduced at the terminals of the component (A1). When a hydroxyalkyl group in which a part of the hydrogen atoms of the alkyl group has been substituted with fluorine atoms is introduced into a copolymer in this manner, the copolymer thus obtained can have an advantageous effect in reducing the levels of developing defects and LER (line edge roughness: non-uniform irregularities within the line side walls).

The weight average molecular weight (Mw) (the polystyrene equivalent value determined by gel permeation chromatography) of the component (A1) is not particularly limited, and is preferably 2,000 to 50,000, more preferably 3,000 to 30,000, and most preferably 5,000 to 20,000. Ensuring that the weight average molecular weight of the polymer compound (A1) is no more than the upper limit, solubility sufficient for a resist solvent relative to a resist solvent can be obtained. Ensuring that it is no less than the lower limit, excellent dry-etching resistance and excellent sectional shape of the resist pattern can be obtained.

Furthermore, the dispersion degree (Mw/Mn) is preferably within a range from 1.0 to 5.0, more preferably from 1.0 to 3.0, and most preferably from 1.2 to 2.5. Herein, Mn represents the number average molecular weight.

[Component (A2)]

It is preferable that the component (A2) has molecular weight within a range from 500 to less than 2,000, and contains an acid dissociable, dissolution inhibiting group exemplified above in the component (A1) and a hydrophilic group. Specific examples thereof include compounds wherein a portion of the hydrogen atoms of the hydroxyl groups within a compound containing a plurality of phenol structures have been substituted with an aforementioned acid dissociable, dissolution inhibiting group.

Here, the term "low molecular compound" in the component (A2) represents a compound that is not a resin component.

The component (A2) is preferably a lower molecular weight phenol compounds known as sensitizers or heat resistance improvement agents for non-chemically amplified g-line or i-line resists in which a part of hydrogen atoms of hydroxyl groups are substituted with the above acid dissociable, dissolution inhibiting group, and can be used arbitrarily selected from those.

Examples of these low molecular weight phenol compounds include the following: Examples include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenylmethane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4-hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Of course, the low molecular weight phenol compounds are not restricted to these examples.

There is no particular restriction on the acid dissociable, dissolution inhibiting group, and examples thereof include those described above.

As the component (A), one kind can be used alone, or two or more kinds can be used in combination.

In the resist composition of the present invention, the content of the component (A) may be adjusted according to the thickness of the resist film to be formed.

<Component (B)>

The component (B) includes an acid generator (B1) represented by the general formula (B1-1) (hereinafter, sometimes referred to as component (B1)). The component (B1) is the same as the compound (B1) in the present invention.

As the component (B1), one kind can be used alone, or two or more kinds can be used in combination.

In the resist composition of the present invention, the amount of the component (B1) in the component (B) is preferably not less than 40% by weight, more preferably not less than 70% by weight, and may be 100% by weight. The amount of the component (B1) is most preferably 100% by weight. When the amount is not less than the lower limit of the above range, the lithography properties such as sensitivity and line width roughness (LWR) can be improved in the formation of the resist pattern using the resist composition of the present invention.

In the component (B), an acid generator (B2) (hereinafter, referred to as component (B2)) other than the component (B1) may be used in combination with the component (B1).

There is no particular restriction on the component (B2) as long as it is a component other then the component (B1), and those proposed as acid generators for chemically-amplified resist can be used as the component (B2).

Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzyl sulfonate-based acid generators; iminosulfonate-based acid generators; and disulfone-based acid generators.

As an onium salt-based acid generator, for example, an acid generator represented by a general formula (b-1) or (b-2) shown below can be used.

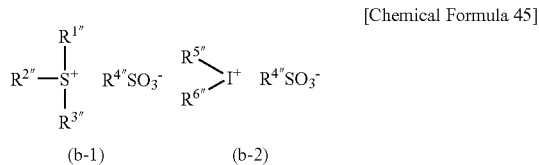

[Chemical Formula 45]

(wherein, $R^{1''}$ to $R^{3''}$, $R^{5''}$ and $R^{6''}$ each independently represents an aryl group or an alkyl group; two of $R^{1''}$ to $R^{3''}$ may mutually be bonded to form a ring together with the sulfur atom; $R^{4''}$ represents a linear, branched or cyclic alkyl group, or a linear, branched or cyclic fluorinated alkyl group; at least one of $R^{1''}$ to $R^{3''}$ represents an aryl group; and at least one of $R^{5''}$ and $R^{6''}$ represents an aryl group.)

In the general formula (b-1), $R^{1''}$ to $R^{3''}$ each independently represents an aryl group or an alkyl group. Here, two of $R^{1''}$ to $R^{3''}$ in the formula (b-1) may mutually be bonded to form a ring together with the sulfur atom.

Also, at least one of $R^{1''}$ to $R^{3''}$ represents an aryl group. Two or more of $R^{1''}$ to $R^{3''}$ are preferably aryl groups, and all of $R^{1''}$ to $R^{3''}$ are most preferably aryl groups. There is no particular restriction on the aryl group of $R^{1''}$ to $R^{3''}$. For example, the aryl group is an aryl group of 6 to 20 carbon atoms, and a part of or all of hydrogen atoms in the aryl group may be substituted with an alkyl group, an alkoxy group, a halogen atom, a hydroxyl group and the like, or may not be substituted. The aryl group is preferably an aryl group of 6 to 10 carbon atoms because it can be synthesized inexpensively. Specific examples thereof include a phenyl group and a naphthyl group.

In the aryl group, the alkyl group with which hydrogen atoms may be substituted is preferably an alkyl group of 1 to 5 carbon atoms, and most preferably a methyl group, an ethyl group, a propyl group, an n-butyl group, and a tert-butyl group.

In the aryl group, the alkoxy group with which hydrogen atoms may be substituted is preferably an alkoxy group of 1 to 5 carbon atoms, and most preferably a methoxy group and an ethoxy group.

In the aryl group, the halogen atom with which hydrogen atoms may be substituted is preferably a fluorine atom.

There is no restriction on the alkyl groups of $R^{1''}$ to $R^{3''}$. Examples thereof include a linear, branched or cyclic alkyl group of 1 to 10 carbon atoms. The number of carbon atoms is preferably 1 to 5, in terms of excellent resolution. Specific examples include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group. Of these, a methyl group is preferable, because it excels in resolution, and can be synthesized inexpensively.

Of these, it is most preferable that $R^{1''}$ to $R^{3''}$ each independently represents a phenyl group or a naphthyl group.

When two of $R^{1''}$ to $R^{3''}$ in the general formula (b-1) may mutually be bonded to form a ring together with the sulfur atom, the ring including the sulfur atom preferably forms a 3- to 10-membered ring, and more preferably forms a 5- to 7-membered ring. Also, when two of $R^{1''}$ to $R^{3''}$ in the general formula (b-1) may mutually be bonded to form a ring together with the sulfur atom, the other of $R^{1''}$ to $R^{3''}$ is preferably an aryl group. The aryl group is the same as those described above in the aryl group for $R^{1''}$ to $R^{3''}$.

$R^{4''}$ represents a linear, branched or cyclic alkyl group, or a linear, branched or cyclic fluorinated alkyl group.

The number of carbon atoms in the linear or branched alkyl group of $R^{4''}$ is preferably from 1 to 10, more preferably from 1 to 8, and most preferably from 1 to 4.

The cyclic alkyl group of $R^{4''}$ is the same as the cyclic group described above in $R^{1''}$. The number of carbon atoms in the cyclic alkyl group of $R^{4''}$ is preferably from 4 to 15, more preferably from 4 to 10, and most preferably from 6 to 10.

The number of carbon atoms in the fluorinated alkyl group is preferably from 1 to 10, more preferably from 1 to 8, and most preferably from 1 to 4. Furthermore, the fluorination rate of the fluorinated alkyl group (proportion of fluorine atoms in the alkyl group) is preferably within a range from 10 to 100%, more preferably from 50 to 100%, and those wherein all hydrogen atoms are substituted with fluorine atoms (perfluoroalkyl groups) are particularly preferable, because the strength of the acid increases.

$R^{4''}$ is most preferably a linear or cyclic alkyl group, or a linear or cyclic fluorinated alkyl group.

In the general formula (b-2), $R^{5''}$ and $R^{6''}$ each independently represents an aryl group or an alkyl group. At least one of $R^{5''}$ and $R^{6''}$ represents an aryl group. Both of $R^{5''}$ and $R^{6''}$ preferably represent aryl groups.

The aryl groups of $R^{5''}$ and $R^{6''}$ are the same as those described above in "aryl group" of $R^{1''}$ to $R^{3''}$.

The alkyl groups of $R^{5''}$ and $R^{6''}$ are the same as those described in "alkyl group" of $R^{1''}$ to $R^{3''}$.

Of these, it is most preferable that both of $R^{5''}$ and $R^{6''}$ be phenyl groups.

$R^{4''}$ in the general formula (b-2) is the same as those described in $R^{4''}$ in the general formula (b-1) shown above.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

Also, onium salts in which anionic sites of these onium salts are substituted with a methansulfonate, an n-propanesulfonate, an n-butanesulfonate, or an n-octanesulfonate can be used.

Further, an onium salt-based acid generator in which the anionic site in the general formula (b-1) or (b-2) is substituted with an anionic site represented by a general formula (b-3) or (b-4) shown below can also be used. Here, the cationic site is the same as those described in the general formula (b-1) or (b-2).

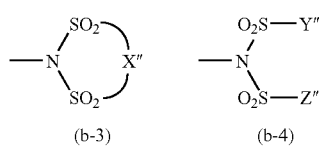

[Chemical Formula 46]

(b-3)      (b-4)

(wherein, X" represents an alkylene group of 2 to 6 carbon atoms in which at least one hydrogen atom is substituted with a fluorine atom; and Y" and Z" each independently represents an alkyl group of 1 to 10 carbon atoms in which at least one hydrogen atom is substituted with a fluorine atom.)

X" represents a linear or branched alkylene group in which at least one hydrogen atom is substituted with a fluorine atom. The number of carbon atoms in the alkylene group of X" is from 2 to 6, preferably from 3 to 5, and most preferably 3.

Y" and Z" each independently represents a linear or branched alkyl group in which at least one hydrogen atom is substituted with a fluorine atom. The number of carbon atoms in the alkyl group of Y" and Z" is from 1 to 10, preferably from 1 to 7, and more preferably from 1 to 3.

Lower numbers of carbon atoms within the alkylene group X" or the alkyl groups Y" and Z" result in better solubility within the resist solvent, and are consequently preferred.

Furthermore, in the alkylene group X" or the alkyl groups Y" and Z", a higher number of hydrogen atoms that have been substituted with fluorine atoms results in increasing the strength of an acid and also improving the transparency relative to high energy light beams of 200 nm or less, or electron beams, and is consequently preferred. The proportion of fluorine atoms in the alkylene group or alkyl group, that is, the fluorination rate, is preferably within a range from 70 to 100%, more preferably from 90 to 100%. A perfluoroalkylene group or a perfluoroalkyl group wherein all hydrogen atoms are substituted with fluorine atoms is most preferable.

Furthermore, a sulfonium salt that contains a cationic site represented by a general formula (b-5) or (b-6) shown below can be used as an onium salt-based acid generator.

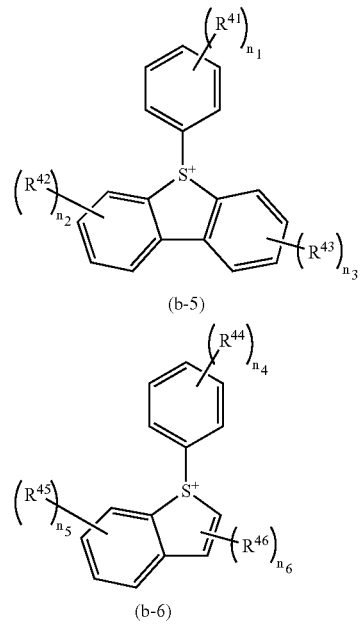

[Chemical Formula 47]

(b-5)

(b-6)

(wherein, $R^{41}$ to $R^{46}$ each independently represents an alkyl group, an acetyl group, an alkoxy group, a carboxyl group, a hydroxyl group or a hydroxyalkyl group; $n_1$ to $n_5$ each independently represents an integer of 0 to 3; and n6 represents an integer of 0 to 2.)

The alkyl group for $R^{41}$ to $R^{46}$ is preferably an alkyl group of 1 to 5 carbon atoms, more preferably a linear or branched alkyl group, and particularly preferably a methyl group, an ethyl group, a propyl group, an isopropyl group, an n-butyl group, or a tert-butyl group.

The alkoxy group for $R^{41}$ to $R^{46}$ is preferably an alkoxy group of 1 to 5 carbon atoms, more preferably a linear or branched alkoxy group, and particularly preferably a methoxy group or an ethoxy group.

The hydroxyalkyl group for $R^{41}$ to $R^{46}$ is preferably a group in which one or more hydrogen atoms in the alkyl group for $R^{41}$ to $R^{46}$ are substituted with hydrogen atoms, and examples thereof include a hydroxymethyl group, a hydroxyethyl group, and a hydroxypropyl group.

In the case that the symbols $n_1$ to $n_6$ to the right of $R^{41}$ to $R^{46}$ are an integer of 2 or more, a multitude of $R^{41}$ to $R^{46}$ may each independently be the same, or different.

$n_1$ is preferably 0 to 2, more preferably 0 or 1, and still more preferably 0.

It is preferable that $n_2$ and $n_3$ are each independently 0 or 1, and it is more preferable that they are 0.

$n_4$ is preferably 0 to 2, and more preferably 0 or 1.

$n_5$ is preferably 0 or 1, and more preferably 0.

$n_6$ is preferably 0 or 1, and more preferably 1.

There is no particular restriction on an anionic site of a sulfonium salt that contains the cationic site represented by the general formula (b-5) or (b-6), and anionic sites of onium salt-based acid generators which have proposed can be used as the anionic site. Examples of the anionic site include a fluorinated alkylsulfonate ion such as the anionic sites $(R^{4''}SO_3^-)$ of the onium salt-based acid generator represented by the general formula (b-1) or (b-2); and an anionic site represented by the general formula (b-3) or (b-4). Of these, a fluorinated alkylsulfonate ion is preferable, a fluorinated alkylsulfonate ion of 1 to 4 carbon atoms is more preferable, and a linear perfluoroalkylsulfonate ion is particularly preferable. Specific examples thereof include a trifluoromethylsulfonate ion, a heptafluoro-n-propylsulfonate ion, and a nonafluoro-n-butylsulfonate ion.

In the present specification, the term "oxime sulfonate-based acid generator" represents a compound which has at least one of the groups represented by a general formula (B-1) shown below, and has a property that generates an acid upon exposure to radiation. These kinds of oxime sulfonate-based acid generators are widely used for a chemically-amplified resist composition, so any oxime sulfonate-based acid generator can be used arbitrarily selected from these.

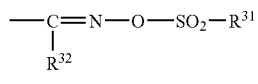

(B-1)

[Chemical Formula 48]

(in the general formula (B-1), $R^{31}$ and $R^{32}$ each independently represents an organic group.)

The organic group for $R^{31}$ or $R^{32}$ is a group containing carbon atoms, and may further contain atoms other than carbon atoms (for example, a hydrogen atom, an oxygen atom, a nitrogen atom, a sulfur atom and a halogen atom (a fluorine atom, a chlorine atom and the like)).

The organic group of $R^{31}$ is preferably a linear, branched or cyclic alkyl group or an aryl group. The alkyl group or aryl group may contain a substituent group. There is no particular restriction on the substituent group, and examples thereof include a fluorine atom, and a linear, branched or cyclic alkyl group of 1 to 6 carbon atoms. Here, the term "containing a substituent group" represents that a part of or all of hydrogen atoms in the alkyl group or aryl group are substituted with substituent groups.

The number of carbon atoms in the alkyl group of $R^{31}$ is preferably from 1 to 20, more preferably from 1 to 10, still more preferably from 1 to 8, still more preferably from 1 to 6, and most preferably from 1 to 4. The alkyl group for $R^{31}$ is particularly preferably an alkyl group which is partially or completely halogenated (Thereinafter, sometimes referred to as a halogenated alkyl group). Here, a partially halogenated alkyl group represents an alkyl group in which a part of the hydrogen atoms is substituted with halogen atoms, and a completely halogenated alkyl group represents an alkyl group in which all of the hydrogen atoms are substituted with halogen atoms. Examples of the halogen atoms include a fluorine atom, a chlorine atom, a bromine atom and an iodine atom. Of these, a fluorine atom is preferable. That is, a halogenated alkyl group is preferably a fluorinated alkyl group.

The number of carbon atoms in the aryl group of $R^{31}$ is preferably from 4 to 20, more preferably from 4 to 10, and most preferably from 6 to 10. The aryl group is particularly preferably an aryl group which is partially or completely halogenated. Here, a partially halogenated aryl group represents an aryl group in which a part of the hydrogen atoms is substituted with halogen atoms, and a completely halogenated aryl group represents an aryl group in which all of the hydrogen atoms are substituted with halogen atoms.

$R^{31}$ is particularly preferably an alkyl group of 1 to 4 carbon atoms containing no substituent group, or a fluorinated alkyl group of 1 to 4 carbon atoms.

The organic group of $R^{32}$ is preferably a linear, branched or cyclic alkyl group, an aryl group, or a cyano group. The alkyl group or the aryl group of $R^{32}$ is the same as those described above in the alkyl group or aryl group of $R^{31}$. $R^{32}$ is particularly preferably a cyano group, an alkyl group of 1 to 8 carbon atoms containing no substituent group, or a fluorinated alkyl group of 1 to 8 carbon atoms.

The oxime sulfonate-based acid generator is more preferably a compound represented by a general formula (B-2) or (B-3) shown below.

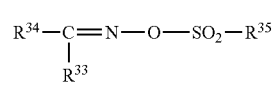

(B-2)

[Chemical Formula 49]

(in the general formula (B-2), $R^{33}$ represents a cyano group, an alkyl group containing no substituent group, or a halogenated alkyl group; $R^{34}$ represents an aryl group; and $R^{35}$ represents an alkyl group containing no substituent group, or a halogenated alkyl group.)

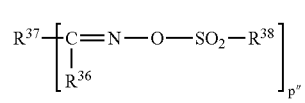

(B-3)

[Chemical Formula 50]

(in the general formula (B-3), $R^{36}$ represents a cyano group, an alkyl group containing no substituent group, or a halogenated alkyl group; $R^{37}$ represents a bivalent or trivalent aromatic hydrocarbon atom; $R^{38}$ represents an alkyl group containing no substituent group or a halogenated alkyl group; and p" represents an integer of 2 or 3.)

In the general formula (B-2), the number of carbon atoms in the alkyl group containing no substituent group or the halogenated alkyl group for $R^{33}$ is preferably from 1 to 10, more preferably from 1 to 8, and most preferably from 1 to 6.

$R^{33}$ is preferably a halogenated alkyl group, and more preferably a fluorinated alkyl group.

The fluorinated alkyl group of $R^{33}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated.

Examples of the aryl group represented by $R^{34}$ include groups in which one hydrogen atom has been removed from an aromatic hydrocarbon ring, such as a phenyl group, a biphenyl group, a fluorenyl group, a naphthyl group, an anthryl group, and a phenantryl group; and heteroaryl groups in which a part of the carbon atoms which constitute the rings of these groups are substituted with heteroatoms such as an oxygen atom, a sulfur atom, and a nitrogen atom. Of these, a fluorenyl group is preferable.

The aryl group of $R^{34}$ may contain a substituent group such as an alkyl group, a halogenated alkyl group and an alkoxy group of 1 to 10 carbon atoms. The number of carbon atoms of the alkyl group or halogenated alkyl group in the substituent group is preferably from 1 to 8, and more preferably from 1 to 4. Also, the halogenated alkyl group is preferably a fluorinated alkyl group.

The number of carbon atoms in the alkyl group containing no substituent group or the halogenated alkyl group for $R^{35}$ is preferably from 1 to 10, more preferably from 1 to 8, and most preferably from 1 to 6.

$R^{35}$ is preferably a halogenated alkyl group, and more preferably a fluorinated alkyl group.

The fluorinated alkyl group of $R^{35}$ is preferably a group in which 50% or more of the hydrogen atoms in the alkyl group are fluorinated, more preferably a group in which 70% or more of the hydrogen atoms in the alkyl group are fluorinated, and still more preferably a group in which 90% or more of the hydrogen atoms in the alkyl group are fluorinated, because the strength of the generated acid increases. The fluorinated alkyl group of $R^{35}$ is most preferably a completely fluorinated alkyl group in which 100% of the hydrogen atoms are substituted with fluorine atoms.

In the general formula (B-3), the alkyl group containing no substituent group or the halogenated alkyl group of $R^{36}$ is the same as those described above in the alkyl group containing no substituent group or the halogenated alkyl group of $R^{33}$.

Examples of the bivalent or trivalent aromatic hydrocarbon group of $R^{37}$ include aryl groups of $R^{34}$ in which one or two hydrogen atoms are further removed.

The alkyl group containing no substituent group or the halogenated alkyl group of $R^{38}$ is the same as those described above in the alkyl group containing no substituent group or the halogenated alkyl group of $R^{35}$.

p" is preferably 2.

Specific examples of the oxime sulfonate-based acid generator include

α-(p-toluenesulfonyloxyimino)-benzylcyanide,
α-(p-chlorobenzenesulfonyloxyimino)-benzylcyanide,
α-(4-nitrobenzenesulfonyloxyimino)-benzylcyanide,
α-(4-nitro-2-trifluoromethylbenzenesulfonyloxyimino)-benzylcyanide,
α-(benzenesulfonyloxyimino)-4-chlorobenzylcyanide,
α-(b enzenesulfonyloxyimino)-2,4-dichlorobenzylcyanide,
α-(benzenesulfonyloxyimino)-2,6-dichlorobenzylcyanide,
α-(benzenesulfonyloxyimino)-4-methoxybenzylcyanide,
α-(2-chlorobenzenesulfonyloxyimino)-4-methoxybenzylcyanide,
α-benzenesulfonyloxyimino)-thien-2-ylacetonitrile,
α-(4-dodecylbenzenesulfonyloxyimino)-benzylcyanide,
α-[(p-toluenesulfonyloxyimino)-4-methoxyphenyl]acetonitrile,
α-[(dodecylbenzenesulfonyloxyimino)-4-methoxyphenyl]acetonitrile,
α-(tosyloxyimino)-4-thienylcyanide,
α-(methylsulfonyloxyimino)-1-cyclopentenylacetonitrile,
α-(methylsulfonyloxyimino)-1-cyclohexenylacetonitrile,
α-(methylsulfonyloxyimino)-1-cycloheptenylacetonitrile,
α-(methylsulfonyloxyimino)-1-cyclooctenylacetonitrile,
α-(trifluoromethylsulfonyloxyimino)-1-cyclopentenylacetonitrile,
α-(trifluoromethylsulfonyloxyimino)-cyclohexylacetonitrile,
α-(ethylsulfonyloxyimino)-ethylacetonitrile,
α-(propylsulfonyloxyimino)-propylacetonitrile,
α-(cyclohexylsulfonyloxyimino)-cyclopentylacetonitrile,
α-(cyclohexylsulfonyloxyimino)-cyclohexylacetonitile,
α-(cyclohexylsulfonyloxyimino)-1-cyclopentenylacetonitrile,
α-(ethylsulfonyloxyimino)-1-cyclopentenylacetonitrile,
α-(isopropylsulfonyloxyimino)-1-cyclopentenylacetonitrile,
α-(n-butylsulfonyloxyimino)-1-cyclopentenylacetonitile,
α-(ethylsulfonyloxyimino)-1-cyclohexenylacetonitrile,
α-(isopropylsulfonyloxyimino)-1-cyclohexenylacetonitrile,
α-(n-butylsulfonyloxyimino)-1-cyclohexenylacetonitrile,
α-(methylsulfonyloxyimino)-phenylacetonitrile,
α-(methylsulfonyloxyimino)-p-methoxyphenylacetonitrile,
α-(trifluoromethylsulfonyloxyimino)-phenylacetonitrile,
α-(trifluoromethylsulfonyloxyimino)-p-methoxyphenylacetonitrile,
α-(ethylsulfonyloxyimino)-p-methoxyphenylacetonitrile,
α-(propylsulfonyloxyimino)-p-methylphenylacetonitrile, and
α-(methylsulfonyloxyimino)-p-bromophenylacetonitrile.

Also, oxime sulfonate-based acid generators disclosed in Japanese Unexamined Patent Application, First Publication No. Hei9-208554 ([Formula 18] and [Formula 19] in paragraphs [0012] to [0014]), and International Publication WO 2004/074242A2 (Examples 1 to 40 on pages 65 to 85) can be preferably used.

Further, suitable examples thereof include the following.

[Chemical Formula 51]

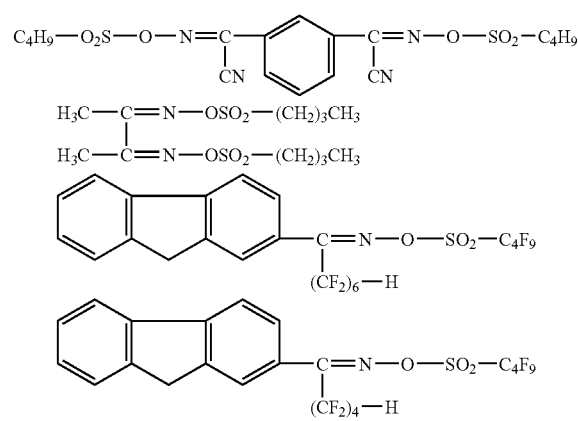

Among the diazomethane-based acid generators, specific examples of bisalkyl- or bisarylsulfonyldiazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Also, diazomethane-based acid generators disclosed in Japanese Unexamined Patent Application, First Publication No. Hei 11-035551, Japanese Unexamined Patent Application, First Publication No. Hei 11-035552, and Japanese Unexamined Patent Application, First Publication No. Hei 11-035573 can be preferably used. Examples of the poly(bissulfonyl)diazomethanes include 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane, which are disclosed in Japanese Unexamined Patent Application, First Publication No. Hei11-322707.

As the component (B2), one kind selected from the above acid generators may be used alone, or two or more kinds may be used in combination.

The amount of the component (B) in the resist composition of the present invention is preferably within a range from 0.5 to 30 parts by mass, and more preferably from 1 to 20 parts by mass, relative to 100 parts by mass of the component (A). When the amount is within the range, a pattern can be sufficiently formed. Also, a uniform solution and an excellent storage stability can be obtained, therefore an amount within the range is preferable.

<Optional Components>

In the resist composition of the present invention, for improving the resist pattern shape and the post exposure stability of the latent image formed by the pattern-wise exposure of the resist layer, it is preferable to add a nitrogen-containing organic compound (D) (hereafter, referred to as component (D)) as an optional component.

Since a multitude of these components (D) have already been proposed, any of these known compounds can be arbitrarily used. Of these, an aliphatic amine, particularly a secondary aliphatic amine or tertiary aliphatic amine is preferred. An aliphatic amine is an amine having one or more aliphatic groups, and the aliphatic groups preferably have 1 to 12 carbon atoms.

Examples of the aliphatic amine include an amine (alkylamine or alkylalcoholamine) wherein at least one of the hydrogen atoms of $NH_3$ is substituted with an alkyl or hydroxyalkyl group having 12 or less carbon atoms.

Specific examples of the alkyamines or alkylalcoholamines include monoalkylamines such as n-hexylamine, n-heptylamine, n-octylamine, n-nonylamine, or n-decylamine; dialkylamines such as diethylamine, di-n-propylamine, di-n-heptylamine, di-n-octylamine, or dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, or tri-n-dodecylamine; and alkylalcoholamines such as diethanolamine, triethanolamine, diisopropanolamine, triisopropanolamine, di-n-octanolamine, or tri-n-octanolamine. Among these amines, trialkylamines, in which three alkyl groups with 5 to 10 carbon atoms are bonded with a nitrogen atom, are preferable, and tri-n-pentylamine is most preferable.

Examples of the cyclic amine include a heterocyclic compound containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amines include piperidine, and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

These may be used either alone, or in combination of two or more different compounds.

The component (D) is typically used in a quantity within a range from 0.01 to 5.0 parts by weight, relative to 100 parts by weight of the component (A).

In the positive resist composition of the present invention, in order to prevent any deterioration in sensitivity, and improve the resist pattern shape and the post exposure stability of the latent image formed by the pattern-wise exposure of the resist layer, at least one compound (E) selected from the group consisting of organic carboxylic acids and phosphorus oxo acids or derivatives thereof (hereinafter, referred to as component (E)) can also be added as an optional component.

Suitable examples of organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly preferable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphate esters such as di-n-butyl phosphate and diphenyl phosphate.

Examples of phosphonic acid derivatives include phosphonate esters such as dimethyl phosphonate, di-n-butyl phosphonate, phenylphosphonic acid, diphenyl phosphonate and dibenzyl phosphonate.

Examples of phosphinic acid derivatives include phosphinic esters such as phenylphosphhlinic acid.

As the component (E), one type may be used alone, or two or more types may be used in combination.

As the component (E), an organic carboxylic acid is preferable, and salicylic acid is particularly preferable.

The component (E) is used in a quantity within a range from 0.01 to 5.0 parts by weight, relative to 100 parts by weight of the component (A).

In the positive resist composition of the present invention, if desired, additives having miscibility, for example, additive resins for improving performance of a resist film, surfactants for improving coatability, dissolution inhibitors, plasticizers, stabilizers, colorants, antihalation agents, and dyes can be appropriately added.

<Organic Solvent (S)>

The resist composition of the present invention can be prepared by dissolving materials in an organic solvent (S) (hereinafter, sometimes referred to as component (S)).

The component (S) may be an organic solvent which can dissolve the respective components used in the present invention to give a uniform solution, and one or more kinds of organic solvents can be used, appropriately selected from those which have been conventionally known as a solvent for a chemically-amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols such as ethylene glycol, diethylene glycol, propylene glycol, dipropylene glycol; derivatives of the polyhydric alcohols, including compounds having ester bonds such as ethylene glycol monoacetate, diethylene glycol monoacetate, propylene glycol monoacetate and dipropylene glycol monoacetate, and compounds having ether bonds such as monoalkyl ethers (for example, monomethyl ether, monoethyl ether, monopropyl ether and monobutyl ether) and monophenyl ether of the above polyhydric alcohols or the above compounds having ester bonds (of these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, ethyl ethoxypropionate; and aromatic organic solvents such as anisole, ethylbenzyl ether, cresylmethyl ether, diphenyl ether, dibenzyl ether, phenetole, butylphenyl ether, ethylbenzene, diethylbenzene, pentylbenzene, isopropylbenzene, toluene, xylene, cymene, and mesitylene.

These organic solvents may be used either alone, or as a mixed solvent of two or more different solvents.

Of these, propylene glycol monomethyl ether acetate (PGMEA), propylene glycol monomethyl ether (PGME) and EL are preferable.

Also, a mixed solvent obtained by mixing PGMEA and a polar solvent is preferable. The mixing ratio (mass ratio) of PGMEA to the polar solvent may be appropriately decided taking account of compatibility, and is preferably adjusted within a range from 1:9 to 9:1, and more preferably from 2:8 to 8:2.

More specifically, in the case of using EL as the polar solvent, the mass ratio PGMEA:EL is preferably from 1:9 to 9:1, and more preferably from 2:8 to 8:2. Furthermore, in those cases of using PGME as the polar solvent, the mass ratio PGME:PGME is preferably from 1:9 to 9:1, more preferably 2:8 to 8:2, and still more preferably 3:7 to 7:3.

Furthermore, as the component (S), mixed solvents of at least one of PGMEA and EL with γ-butyrolactone are also preferred. In such cases, the mass ratio of the former and latter components in the mixed solvents is preferably within a range from 70:30 to 95:5.

There is no particular restriction on the quantity of the component (S), and the quantity should be set in accordance with the required coating film thickness within a concentration that enables favorable application of the solution to a substrate or the like. Typically, the quantity is set so that the solid fraction concentration within the resist composition falls within a range from 2 to 20% by weight, and still more preferably from 5 to 15% by weight.

<<Method of Forming Resist Pattern>>

A method of forming a resist pattern of the present invention includes the steps of forming a resist film on a substrate using the resist composition described above, exposing the resist film, and developing the resist film to form a resist pattern.

The method of forming a resist pattern of the present invention can be performed, for example, in the following manner.

Namely, the resist composition described above is first applied to a substrate using a spinner or the like, a prebake is then conducted under temperature conditions of 80 to 150° C. for 40 to 120 seconds, preferably for 60 to 90 seconds, followed by selective exposure of the thus obtained film with an ArF exposure apparatus or the like, by irradiating ArF excimer laser light through a desired mask pattern, and then PEB (post exposure baking) is conducted under temperature conditions of 80 to 150° C. for 40 to 120 seconds, preferably for 60 to 90 seconds. Subsequently, a developing treatment is conducted using an alkali developing solution such as a 0.1 to 10% by mass aqueous solution of tetramethylammonium hydroxide (TMAH), preferably followed by rinsing with pure water, and drying. Also, according to circumstances, a bake treatment (post bake) may be conducted after the above developing treatment. In this manner, a resist pattern that is faithful to the mask pattern can be obtained.

The substrate is not specifically limited and a conventionally known substrate can be used. For example, substrates for electronic components, and such substrates having prescribed wiring patterns formed thereon can be exemplified. Specific examples thereof include a silicon wafer; a substrate made of a metal such as copper, chromium, iron and aluminum; and a substrate made of glass. As materials for the wiring pattern, for example, copper, aluminum, nickel and gold can be used. Further, as the substrate, any one of the above-exemplified substrates provided with an inorganic and/or organic film on the surface thereof may be used. As the inorganic film, an inorganic anti-reflection film (inorganic BARC) can be exemplified. As the organic film, an organic anti-reflection film (organic BARC) can be exemplified.

There is no particular restriction on the wavelength used for the exposure, and the exposure can be conducted using radiation such as ArF excimer lasers, KrF excimer lasers, $F_2$ excimer lasers, extreme ultraviolet rays (EUV), vacuum ultraviolet rays (VV), electron beams (EB), X-rays, and soft X-rays. The resist composition is effective for KrF excimer lasers, ArF excimer lasers, EB and EUV, and particularly effective for ArF excimer lasers.

The exposure of the resist film may be a usual exposure conducted in an inactive gas such as an air or a nitrogen gas (dry exposure), or may be an immersion exposure (liquid immersion lithography).

As described above, the immersion exposure is conventionally conducted in the condition that the region between a lens and a resist film on a wafer is filled with a solvent (immersion solvent) that has a larger refractive index than the refractive index of air.

More specifically, the immersion exposure is performed in the following manner. First, the region between the resist film obtained in the above manner and the lens at the lowermost point of the exposure apparatus is pre-filled with a solvent (immersion solvent) that has a larger refractive index than the refractive index of air, and then, keeping such a condition, the exposure (immersion exposure) is conducted through the desired mask pattern.

The immersion solvent is preferably a solvent that has a refractive index larger than the refractive index of air but smaller than the refractive index of the resist film exposed by the immersion exposure. There is no restriction on the refractive index of the immersion solvent, as long as the solvent has a refractive index within the above range.

Examples of the solvent which has a refractive index larger than that of air, but smaller than that of a resist film include water, fluorine-based inactive liquid, a silicon-based solvent, and a hydrocarbon-based solvent.

Specific examples of the fluorine-based inactive liquid include a liquid which has a fluorine-based compound as a main component, such as $C_3HCl_2F_5$, $C_4F_9OCH_3$, $C_4F_9OC_2H_5$, and $C_5H_3F_7$. The fluorine-based inactive liquid preferably has a boiling point within a range from 70 to 180° C., and more preferably from 80 to 160° C. If the fluorine-based inactive liquid has a boiling point within the above range, the solvent used for the immersion exposure can be removed by a convenient method after exposure, and consequently it is preferable.

The fluorine-based inactive liquid is particularly preferably a perfluoroalkyl compound in which all hydrogen atoms of the alkyl groups are substituted with fluorine atoms. Examples of these perfluoroalkyl compounds include perfluoroalkylether compounds and perfluoroalkylamine compounds.

Specific examples of the perfluoroalkylether compounds include a perfluoro(2-butyl-tetrahydrofuran) (boiling point 102° C.), and specific examples of the perfluoroalkylamine compounds include a perfluorotributylamine (boiling point 174° C.).

The resist composition of the present invention is a novel resist composition which has not been known conventionally.

Further, the resist composition of the present invention has excellent lithographic properties such as sensitivity and resolution, and can form a fine resist pattern for a line and space pattern with a line width of 120 nm or less. Furthermore, in the case of forming a resist pattern using a conventional resist composition, there is such a problem that the resist pattern shape tends to be deteriorated. For example, in the conventional resist composition, the resist pattern causes footing on the surface of the substrate, thereby reducing a rectangularity. On the other hand, the resist composition of the present invention enables a resist pattern with reduced footing to be formed.

Furthermore, the component (B1) used in the resist composition of the present invention exhibits high transparency to a wavelength of 200 nm or less, particularly to a wavelength around 193 nm, as compared to an acid generator conventionally used in a chemically-amplified resist composition, such as triphenylsulfonium salts or the like. Therefore, the resist composition of the present invention enables a large amount of the component (B) to be blended, as compared to a conventional resist composition.

Furthermore, the component (B1) has an excellent efficiency in generating an acid upon exposure, therefore the resist composition of the present invention exhibits excellent sensitivity by including the component (B1) as the component (B).

It is speculated that these effects should be affected by the structure of the cationic site in the component (B1).

Also, it is also speculated that these effects should be affected by the fact that the component (B1) contains the anionic site with such a structure that the functional group of "$R^1$—O—$[CO]_n$—" is introduced into the skelton of $Y^1$—$SO_3$—. That is, in spite that the anionic site with the above structure has the relatively small number of the carbon atoms (from 1 to 4 carbon atoms) in the alkylene group for $Y^1$ in which hydrogen atoms may be substituted with fluorine atoms, the anionic site with the above structure can suppress excessive diffusion of an acid upon exposure, as compared to an anionic site of a conventional acid generator, such as nonafluorobutanesulfonate. Therefore, it is speculated that a resist pattern with excellent lithographic properties can be formed.

Also, in the component (B1), $Y^1$ is an alkyl chain of an alkylene group of 1 to 4 carbon atoms in which hydrogen atoms may be substituted with fluorine atoms. Therefore, the component (B1) can be handled more safely in terms of bioaccumulation potential than a perfluoroalkyl chain of 6 to 10 carbon atoms which is persistent (hardly-degradable).

EXAMPLES

Next, the present invention will be described in more detail with reference to examples, but the scope of the present invention is not limited to the following examples.

Example 1

5 ml of tetrahydrofuran was added into 1.0 g of allyloxytetrafluoroethane sulfonylfluoride. The solution thus obtained was dripped into an aqueous solution in which 0.20 g of lithium hydroxide was dissolved in 2.8 ml of pure water in a water bath, and then stirred in the water bath. As no absorption of $^{19}$F-NMR at −217.8 ppm by —$SO_2F$ was observed, it was confirmed that all fluorinated sulfonyl groups were changed to lithium sulfonate. Subsequently, the reaction solution was concentrated and dried, thereby obtaining a white viscous solid. The crude product thus obtained was dissolved in 3.35 ml of acetone, and filtered in order to remove LiF obtained as a by-product. Subsequently, the filtrate was concentrated, thereby obtaining 0.58 g of a compound (1-1) represented by a general formula (1-1) shown below.

[Chemical Formula 52]

(1-1)

Next, 10.00 g of diphenyliodonium methanesulfonate was dissolved in 50.00 g of a water, 6.81 g of the compound (1-1) was added thereinto, and then stirred at room temperature for 1 hour.

After the reaction was finished, 68.9 g of ethylacetate was added thereinto, and extraction treatment was conducted. After fractionation, the organic layer was washed 5 times using 34.5 g of pure water. After washing, the organic layer thus obtained was concentrated, thereby obtaining 6.70 g of the objective compound.

As to the obtained compound (hereinafter, referred to as compound (I-11)), analyses by $^1$H-NMR and $^{19}$F-NMR were conducted. The results are shown below.

$^1$H-NMR (solvent: $CDCl_3$, 400 MHz): δ (ppm)=7.94 (d, 4H ($H^a$)), 7.44 (d, 2H ($H^c$)), 7.30 (t, 4H ($H^b$)), 5.71-5.80 (m, 1H ($H^e$)), 5.06-5.29 (m, 2H ($H^d$)), 4.34 (d, 2H ($H^f$)).

$^{19}$F-NMR (solvent: $CDCl_3$, 376 MHz): δ (ppm)=−83.6, −115.7.

From the result described above, it could be confirmed that the compound (I-11) had a structure shown below.

[Chemical Formula 53]

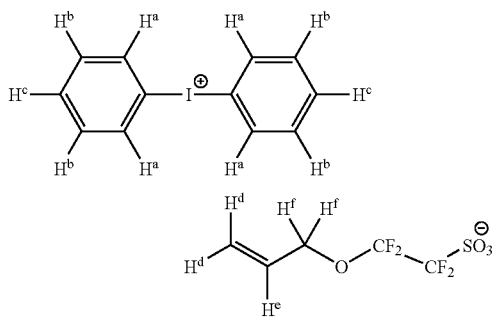

3.93 g of the compound (I-11), 0.7745 g of pentamethylenesulfide, 0.060 g of copper benzoate (II) were dissolved in 5.90 g of chlorobenzene, and then they were reacted for 1 hour at 100° C. After the reaction, the reaction solution was concentrated and dried, and then dissolved in 26.2 g of dichloromethane.

The dichloromethane solution was washed and then concentrated, thereby obtaining 0.84 g of the objective compound.

As to the obtained compound (hereinafter, referred to as compound (b1-11)), analyses by $^1$H-NMR and $^{19}$F-NMR were conducted. The results are shown below.

$^1$H-NMR (solvent: CDCl$_3$, 400 MHz): δ (ppm)=8.10 (d, 2H (H$^c$)), 7.59-7.69 (m, 3H (H$^a$+H$^b$)), 5.86-5.96 (m, 1H (H$^h$)), 5.19-5.42 (m, 2H (H$^g$)), 4.50 (d, 2H (H$^i$)), 3.68-3.98 (m, 4H (H$^d$)), 1.85-2.30 (m, 6H (H$^e$+H$^f$)).

$^{19}$F-NMR (solvent: CDCl$_3$, 376 MHz): δ (ppm)=−79.9, −112.2.

From the result described above, it could be confirmed that the compound (b1-11) had a structure shown below.

[Chemical Formula 54]

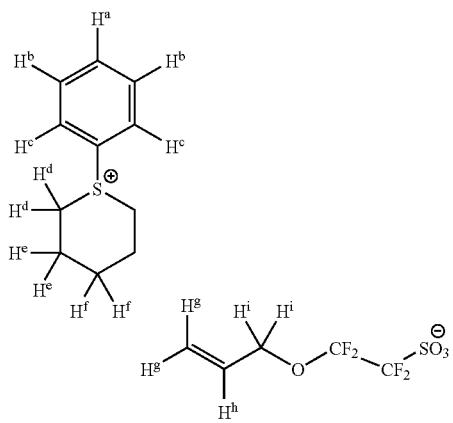

Example 2

6.7 ml of tetrahydrofuran was added into 5.0 g of 2-naphthylmethyloxytetrafluoroethanesulfonylfluoride. The solution thus obtained was dripped into an aqueous solution in which 0.98 g of lithium hydroxide was dissolved in 13.6 ml of pure water in an ice bath. Then, it was stirred in an ice bath. As no absorption of $^{19}$F-NMR at −217.6 ppm by —SO$_2$F was observed, it was confirmed that all fluorinated sulfonyl groups were changed to lithium sulfonate. Subsequently, the reaction solution was concentrated and dried, thereby obtaining a white viscous solid. The crude product thus obtained was dissolved in 14.2 ml of acetone, and filtered in order to remove LiF obtained as a by-product. Subsequently, the filtrate was concentrated, thereby obtaining 5.50 g of a compound (1-2) represented by a general formula (1-2) shown below.

[Chemical Formula 55]

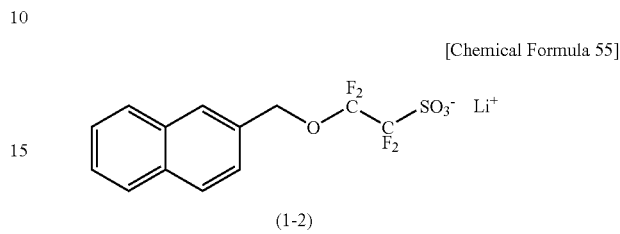

(1-2)

Next, 7.64 g of diphenyliodonium methanesulfonate was dissolved in 38.02 g of water, 7.30 g of the compound (1-2) was added thereinto, and then stirred at room temperature for 1 hour. After the reaction was finished, 38.02 g of ethylacetate was added thereinto, and extraction treatment was conducted. After fractionation, the organic layer was washed 5 times using 38.02 g of pure water. After washing, the organic layer was crystallized using hexane. The powder thus obtained was dried under reduced pressure, thereby obtaining 10.87 g of the objective compound.

As to the obtained compound (hereinafter, referred to as compound (I-12)), analyses by $^1$H-NMR and $^{19}$F-NMR were conducted. The results are shown below.

$^1$H-NMR (solvent: CDCl$_3$, 400 MHz): δ (ppm)=7.99-8.01 (d, 4H (H$^a$)), 7.59 (s, 1H (H$^d$)), 7.80-7.83 (m, 3H (Phenyl+Naphtyl)), 7.39-7.58 (m, 9H (Phenyl+Naphtyl)), 5.20 (s, 2H (H$^e$)).

$^{19}$F-NMR (solvent: CDCl$_3$, 376 MHz): δ (ppm)=−79.0, −111.6.

From the result described above, it could be confirmed that the compound (I-12) had a structure shown below.

[Chemical Formula 56]

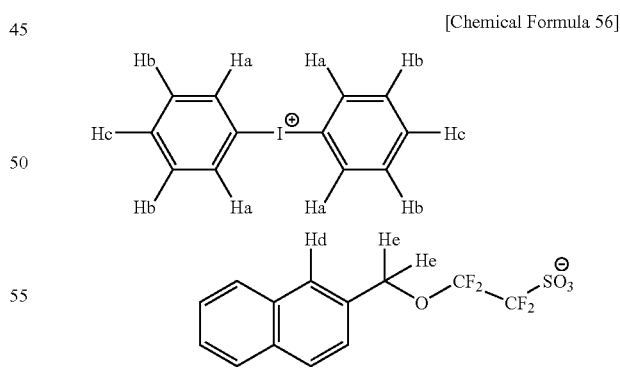

8.00 g of the compound (I-12), 1.32 g of pentamethylenesulfide, 0.10 g of copper benzoate (II) were dissolved in 12.00 g of chlorobenzene, and then they were reacted for 1 hour at 100° C. After the reaction, the reaction solution was concentrated and dried, and then dissolved in 33.40 g of dichloromethane. The dichloromethane solution was washed and then concentrated, thereby obtaining 0.53 g of the objective compound.

As to the obtained compound (hereinafter, referred to as compound (b1-12)), analyses by $^1$H-NMR and $^{19}$F-NMR were conducted. The results are shown below.

$^1$H-NMR (solvent: CDCl$_3$, 400 MHz): δ (ppm)=7.93-7.95 (d, 2H (H$^c$)), 7.85 (s, 1H (H$^g$)), 7.77-7.81 (m, 3H (Phenyl+Naphthyl)), 7.46-7.56 (m, 6H (Phenyl+Naphthyl)), 5.21 (s, 2H (H$^b$)), 3.48-3.79 (m, 4H (H$^d$)), 1.68-2.13 (m, 6H (H$^e$+H$^f$)).

$^{19}$F-NMR (solvent: CDCl$_3$, 376 MHz): δ (ppm)=−84.0, −116.5.

From the result described above, it could be confirmed that the compound (b1-12) had a structure shown below.

[Chemical Formula 57]

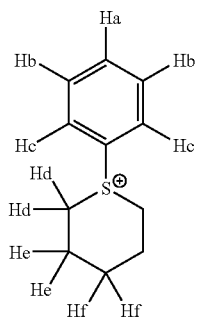

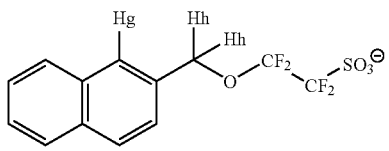

Comparative Example 1

0.28 g of triphenylsulfoniumbromide was dissolved in 5.0 ml of pure water. 0.17 g of the compound (1-1) obtained in the same manner as in Example 1 was added thereinto, and then it was stirred for 14 hours at room temperature. Subsequently, 10 ml of dichloromethane was added thereinto, and stirred. Then, the organic layer was extracted by fractionation.

Furthermore, the organic layer was washed using 5.0 ml of pure water, and then the organic layer was extracted by fractionation. The organic layer thus obtained was concentrated and dried, thereby obtaining 0.16 g of the objective compound.

As to the obtained compound (hereinafter, referred to as compound (b2-11)), analyses by $^1$H-NMR and $^{19}$F-NMR were conducted. The results are shown below.

$^1$H-NMR (acetone-d6, 400 MHz): δ (ppm)=8.30-7.60 (m, 15H (H$^a$)), 5.91 (m, 1H (H$^b$)) 5.47 (d, 1H (H$^c$)), 5.16 (d, 1H (H$^d$)), 4.48 (d, 2H (H$^e$).

$^{19}$F-NMR (acetone-d6, 376 MHz): δ (ppm)=79.8, 112.1.

From the result described above, it could be confirmed that the compound (b2-11) had a structure shown below.

[Chemical Formula 58]

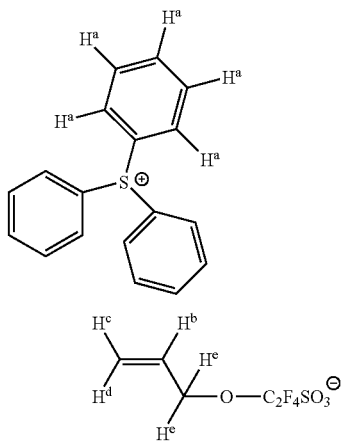

Comparative Example 2

6.99 g of triphenylsulfoniumbromide was dissolved in 125 ml of pure water. 5.50 g of the compound (1-2) obtained in the same manner as in Example 2 was added thereinto, and then it was stirred for 19 hours at room temperature. Subsequently, 125 g of dichloromethane was added thereinto, and stirred. Then, the organic layer was extracted by fractionation.

Furthermore, the organic layer was washed using 40.0 ml of pure water, and then the organic layer was extracted by fractionation. The organic layer thus obtained was concentrated and dried, thereby obtaining 7.09 g of the objective compound (yield: 75.2%).

As to the obtained compound (hereinafter, referred to as compound (b2-12)), analyses by $^1$H-NMR and $^{19}$F-NMR were conducted. The results are shown below.

$^1$H-NMR (acetone-d6, 400 MHz): δ (ppm)=8.01-7.47 (m, 22H (H$^a$)), 5.23 (s, 2H (H$^b$)).

$^{19}$F-NMR (acetone-d6, 376 MHz): δ (ppm)=79.2, 111.8.

From the result described above, it could be confirmed that the compound (b2-12) had a structure shown below.

[Chemical Formula 59]

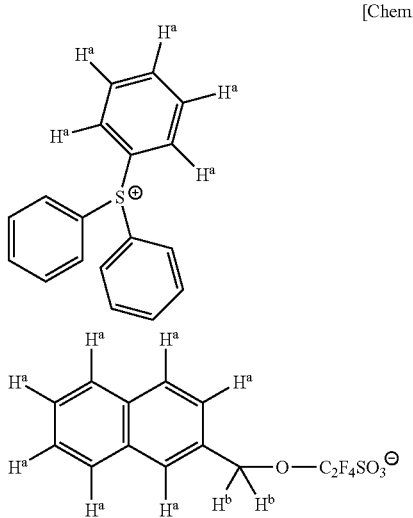

Example 3

5.00 g of 1-(2-oxo-2-phenylethyl)tetrahydrothiophenium bromide was dissolved in 25.0 ml of pure water. 6.6 g of the compound (1-2) obtained in the same manner as in Example 2 was added thereinto, and then it was stirred for 2 hours at room temperature. Subsequently, 25.0 g of dichloromethane was added thereinto, and dichloromethane layer was fractionated. After fractionation, the layer was washed using dilute hydrochloric acid and water, and then 250.0 g of n-hexane was added, thereby obtaining 8.5 g of the objective compound as a white solid.

[Chemical Formula 60]

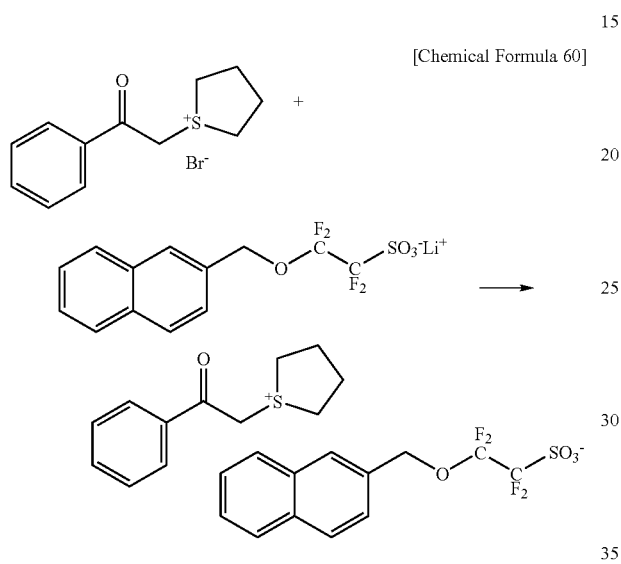

As to the obtained compound (hereinafter, referred to as compound (b1-13)), analyses by $^1$H-NMR and $^{19}$F-NMR were conducted. The results are shown below. Prom the result, it could be confirmed that the compound (b1-13) had a structure shown above.

1H-NMR (DMSO-d6, 400 MHz): δ (ppm)=7.88-8.01 (m, 6H (Ar)), 7.75 (t 1H (Ar)), 7.61 (t, 2H (Ar)), 7.52-7.54 (m, 3H (Ar)), 5.34 (s, 2H (CH$_2$)), 5.20 (s, 2H (CH$_2$)), 3.48-3.59 (m, 4H (CH$_2$—CH$_2$)), 2.17-2.26 (m, 4H (CH$_2$—CH$_2$)).

$^{19}$F-NMR (acetone-d6, 376 MHz): δ (ppm)=−79.6, −111.9.

[Evaluation of Solubility in Solvent]

As to the compounds (b0-11), (b1-12), (b0-13), (b2-11) and (b2-12) which were obtained in the above Examples 1 to 3, and Comparative Examples 1 and 2 respectively, and a compound (b2-13) represented by a general formula (b2-13) shown below, solubility in a solvent was evaluated by the following procedure.

Changing the additive amount, each compound was added into propylene glycol monomethyl ether acetate (PGMEA), propylene glycol monomethyl ether (PGME) or ethyl lactate (EL), which were commonly-used resist solvents, and stirred for 30 minutes at 25° C. After the stir was finished, such a concentration (% by weight) that each compound was completely dissolved was measured. The results are shown in Table 1.

[Chemical Formula 61]

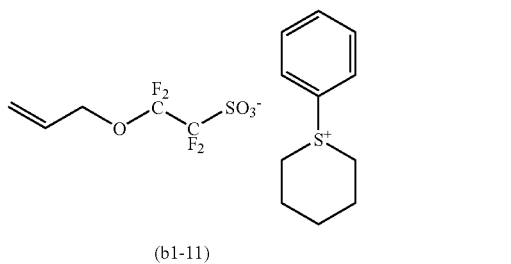

(b1-11)

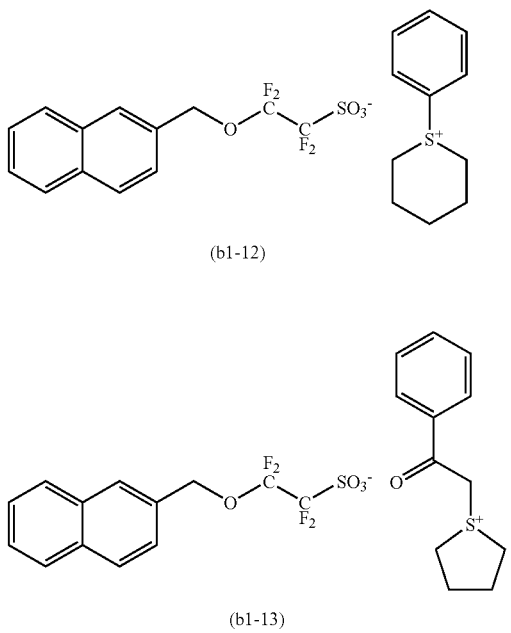

(b1-12)

(b1-13)

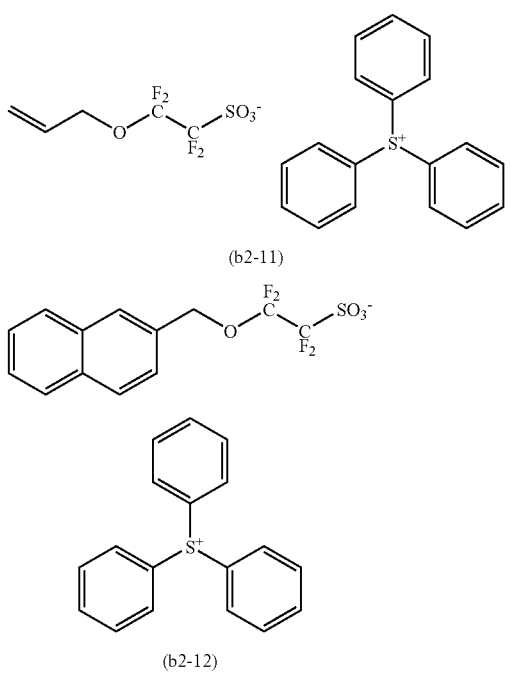

(b2-11)

(b2-12)

-continued

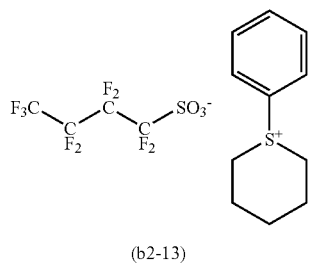

(b2-13)

As shown in Table 1, the compounds (b1-11), (b1-12) and (b2-13) of the present invention had extremely high solubility in PGMEA, PGME and EL.

On the other hand, the compound (b2-11) had relatively good solubility in PGME and EL, but low solubility in PGMEA. Also, the compound (b2-12) had low solubility in all of the solvents. Also, the compound (b1-13), which has a different cationic site from the compound (b2-12), improved solubility in PGMEA.

Examples 4 to 6, and Comparative Example 3

As shown in Table 2, each component was mixed, and dissolved, thereby preparing a posive resist composition.

In Table 2, the values within the brackets [ ] represent the blending amount (parts by weight). Also, the meanings of the abbreviations are described below. Here, the blending amounts of the component (B) are controlled to be equimolar amount.

(A)-1: a copolymer represented by a general formula (A)-1 shown below (Mw=7,000; Mw/Mn=1.8) (in the formula, l/m/n=45/35/20 (molar ratio)).
(B)-1: the compound (b1-11) obtained in the example 1.
(B)-2: the compound (b1-12) obtained in the example 2.
(B)-3: the compound (b1-13) obtained in the example 3.
(B)-4: the compound (b2-13) represented by the general formula (b2-13)
(D)-1: tri-n-pentylamine.
(E)-1: salicylic acid.
(S)-1: γ-butyrolactone.
(S)-2: a mixture solvent of PGMEA/PGME=6/4 (mass ratio).

[Chemical Formula 62]

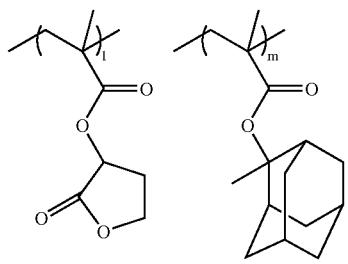

TABLE 1

|  | PGMEA | PGME | EL |
| --- | --- | --- | --- |
| Compound (b1-11) | >30% by weight | >30% by weight | >30% by weight |
| Compound (b1-12) | >30% by weight | >30% by weight | >30% by weight |
| Compound (b1-13) | <1% by weight | 2 to 3% by weight | 5% by weight |
| Compound (b2-11) | 2 to 5% by weight | >30% by weight | >30% by weight |
| Compound (b2-12) | <0.1% by weight | 2 to 5% by weight | 5 to 10% by weight |
| Compound (b2-13) | >30% by weight | >30% by weight | >30% by weight |

TABLE 2

|  | Component (A) | Component (B) | Component (D) | Component (E) | Component (S) | |
| --- | --- | --- | --- | --- | --- | --- |
| Example 4 | (A)-1 | (B)-1 | (D)-1 | (E)-1 | (S)-1 | (S)-2 |
|  | [100] | [8.17] | [0.54] | [1.32] | [10] | [2380] |
| Example 5 | (A)-1 | (B)-2 | (D)-1 | (E)-1 | (S)-1 | (S)-2 |
|  | [100] | [10.14] | [0.54] | [1.32] | [10] | [2380] |
| Example 6 | (A)-1 | (B)-3 | (D)-1 | (E)-1 | (S)-1 | (S)-2 |
|  | [100] | [10.68] | [0.54] | [1.32] | [10] | [2380] |
| Comparative Example 3 | (A)-1 | (B)-4 | (D)-1 | (E)-1 | (S)-1 | (S)-2 |
|  | [100] | [9.39] | [0.54] | [1.32] | [10] | [2380] |

-continued

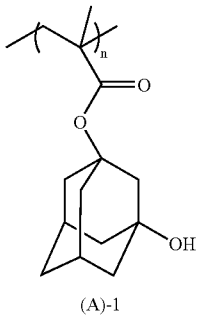

(A)-1

Resist patterns were formed by the following procedure using the resist composition solutions thus obtained, and lithography properties were evaluated.

[Resolution and Sensitivity]

An organic anti-reflection film composition (product name: ARC29A, manufactured by Brewer Science Ltd.) was applied onto an 8-inch silicon wafer using a spinner, and the composition was then baked at 205° C. for 60 seconds, thereby forming an organic anti-reflection film having a film thickness of 82 nm. The resist composition thus obtained was applied onto the organic anti-reflection film using a spinner, and the resist composition was then prebaked (PAB) at 110° C. for 60 seconds and dried, thereby forming a resist film having a film thickness of 150 nm.

Subsequently, the obtained resist layer was selectively exposed by an ArF excimer laser (193 nm), using an ArF exposure apparatus "NSR-S302" (manufactured by Nikon; numerical aperture (NA)=0.60, ⅔ annual illumination) through a mask pattern (6% half tone). Thereafter, a post exposure baking (PEB) treatment was conducted at 110° C. for 60 seconds, followed by a development treatment for 30 seconds at 23° C. in a 2.38% by weight aqueous solution of tetramethylammonium hydroxide (TMAH), rinsing with pure water for 30 seconds, and drying by shaking.

As a result, in any example, a line and space (1:1) resist pattern (L/S pattern) with a line width of 120 nm and a pitch of 240 nm was formed.

Furthermore, the optimum exposure (Eop: (mJ/cm²)) for a line and space pattern (L/S pattern) with a line width of 120 nm and a pitch of 240 nm, that is, the sensitivity was measured. The results are shown in Table 3.

[Line Wise Roughness (LWR)]

The line width in each L/S pattern formed by using the above Eop was measured at 5 locations along the line direction using a measuring SEM (product name: S-9220, manufactured by Hitachi, Ltd.), and the results of these measurements were used to calculate a value (namely, 3 s) of 3 times the standard deviation (s), which was used as an indicator of the LWR. The results are shown in Table 3. The smaller this 3 s value becomes, the lower the level of roughness in the line width, indicating a US pattern with a more uniform width.

TABLE 3

|  | Example 4 | Example 5 | Example 6 | Comparative Example 3 |
|---|---|---|---|---|
| Eop (mJ/cm²) | 22.0 | 35.7 | 102.3 | 25.3 |
| LWR (nm) | 11.4 | 11.1 | 11.2 | 12.7 |

As shown in Table. 3, the resist compositions in examples 4 to 6 have excellent line width roughness (LWR). On the other hand, the resist composition in comparative example 3 has poor LWR.

The invention claimed is:

1. A resist composition, which comprises a base component (A) which exhibits changed solubility in an alkali developing solution under action of acid, and an acid generator component (B) which generates an acid upon exposure, wherein the acid generator component (B) comprises an acid generator (B1) represented by a general formula (b1-1) shown below:

[Chemical Formula 5]

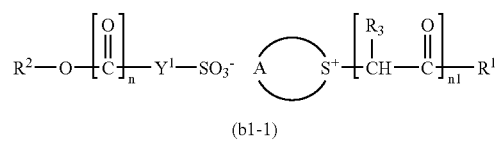

(b1-1)

(wherein, $R^1$ represents an aryl group or alkyl group which may contain a substituent group; $R^3$ represents a hydrogen atom or an alkyl group; n1 represents an integer of 0 or 1, and in the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded; A represents a bivalent group which forms a ring with 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0; and $Y^1$ represents an alkylene group of 1 to 4 carbon atoms in which hydrogen atoms may be substituted with fluorine atoms).

2. The resist composition according to claim 1, wherein the base component (A) is a base component which exhibits increased solubility in an alkali developing solution under action of acid.

3. The resist composition according to claim 2, wherein the base component (A) comprises a resin component (A1) which exhibits increased solubility in an alkali developing solution under action of acid, and the resin component (A1) comprises a structural unit (a1) derived from an acrylate ester containing an acid dissociable, dissolution inhibiting group.

4. The resist composition according to claim 3, wherein the resin component (A1) further comprises a structural unit (a2) derived from an acrylate ester which has a lactone-containing cyclic group.

5. The resist composition according to claim 3, wherein the resin component (A1) further comprises a structural unit (a3) derived from an acrylate ester which has a polar group-containing aliphatic hydrocarbon group.

6. The resist composition according to claim 4, wherein the resin component (A1) further comprises a structural unit (a3) derived from an acrylate ester which has a polar group-containing aliphatic hydrocarbon group.

7. The resist composition according to claim 1, which comprises a nitrogen-containing organic compound (D).

8. A method of forming a resist pattern, comprising:
forming a resist film on a substrate using the resist composition described in any one of claim 1 to 7;

exposing the resist film; and alkali-developing the resist film to form a resist pattern.

9. A compound represented by a general formula (b1-1) shown below:

[Chemical Formula 1]

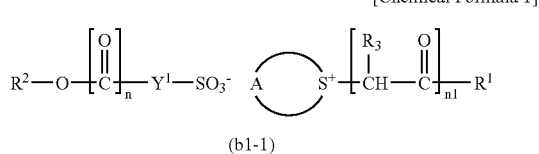

(b1-1)

(wherein, $R^1$ represents an aryl group or alkyl group which may contain a substituent group; $R^3$ represents a hydrogen atom or an alkyl group; n1 represents an integer of 0 or 1, and in the case that n1 is 1, $R^1$ and $R^3$ may mutually be bonded to form a ring with a 3- to 7-membered ring structure together with the carbon atom with which $R^1$ is bonded and the carbon atom with which $R^3$ is bonded; A represents a bivalent group which forms a ring with 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0; and $Y^1$ represents an alkylene group of 1 to 4 carbon atoms in which hydrogen atoms may be substituted with fluorine atoms).

10. A method of manufacturing a compound represented by a general formula (b1-1-1) shown below, which comprises reacting a compound represented by a general formula (I) shown below, a compound represented by a general formula (II) shown below, and a copper catalyst, thereby obtaining the compound represented by the general formula (b1-1-1):

[Chemical Formula 2]

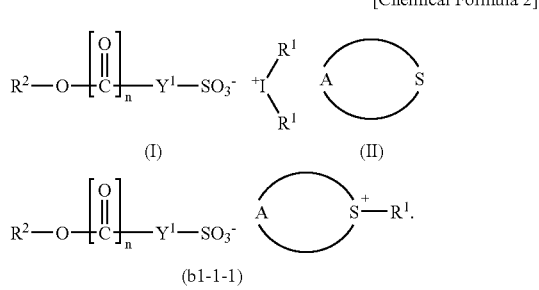

(wherein, A represents a bivalent group which forms a ring with a 3- to 7-membered ring structure together with the sulfur atom with which A is bonded, and the ring may contain a substituent group; $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0; $Y^1$ represents an alkylene group of 1 to 4 carbon atoms in which hydrogen atoms may be substituted with fluorine atoms; and $R^1$ each independently represents an aryl group or alkyl group which may contain a substituent group).

11. A compound represented by a general formula (I) shown below:

[Chemical Formula 3]

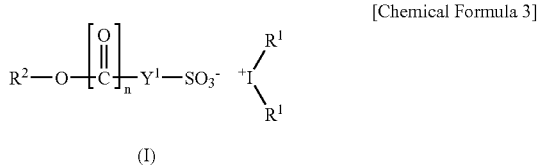

(I)

(wherein, $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0; $Y^1$ represents an alkylene group of 1 to 4 carbon atoms in which hydrogen atoms may be substituted with fluorine atoms; and $R^1$ each independently represents an aryl group or alkyl group which may contain a substituent group).

12. A method of manufacturing a compound represented by a general formula (I) shown below, which comprises reacting a compound represented by a general formula (I-1) shown below, a compound represented by a general formula (I-2) shown below, thereby obtaining the compound represented by the general formula (I):

[Chemical Formula 4]

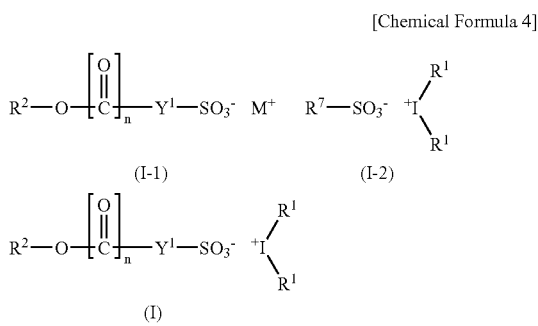

(wherein, $R^2$ represents an aromatic group which may contain a substituent group, a linear or branched alkyl group of 1 to 10 carbon atoms which may contain a substituent group, or a linear or branched alkenyl group of 2 to 10 carbon atoms which may contain a substituent group; n represents an integer of 0; $Y^1$ represents an alkylene group of 1 to 4 carbon atoms in which hydrogen atoms may be substituted with fluorine atoms; $M^+$ represents an alkali metal ion; $R^1$ each independently represents an aryl group or alkyl group which may contain a substituent group; and $R^7$ represents an alkyl group or a fluorinated alkyl group).

13. An acid generator composed of the compound described in claim 9.

14. The resist composition according to claim 1, wherein the anionic site of the acid generator (B1) is an anionic site represented by a general formula (b1"-1) shown below:

(b1"-1)

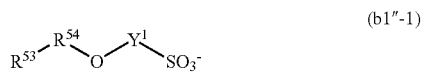

(wherein, $Y^1$ is as defined above; $R^{53}$ represents an alkenyl group or aryl group of 2 to 10 carbon atoms; and $R^{54}$ represents a linear or branched alkylene group of 1 to 5 carbon atoms).

15. The compound according to claim 9, wherein the anionic site of the compound represented by the general formula (b1-1) is an anionic site represented by a general formula (b1"-1) shown below:

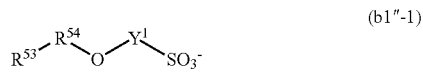
(b1"-1)

(wherein, $Y^1$ is as defined above; $R^{53}$ represents an alkenyl group or aryl group of 2 to 10 carbon atoms; and $R^{54}$ represents a linear or branched alkylene group of 1 to 5 carbon atoms).

16. The resist composition according to claim 1, wherein $Y^1$ is —$CF_2CF_2$—, —$CF_2CF_2CF_2$—, or —$CH_2CF_2CF_2$—.

17. The compound according to claim 9, wherein $Y^1$ is —$CF_2CF_2$—, —$CF_2CF_2CF_2$—, or —$CH_2CF_2CF_2$—.

18. The resist composition according to claim 1, wherein said aromatic group which may contain a substituent group is a phenyl group, a biphenyl group, or a naphthyl group; a heteroaryl group in which a part of the carbon atoms which constitutes the rings of a phenyl group, a biphenyl group or a naphthyl group are substituted with heteroatoms; or a benzyl group, a phenylhyl group, a 1-naphthylmethyl group, a 2-naphthylmethyl group, a 1-naphthylethyl group, or a 2-naphthylethyl group.

19. The compound according to claim 9, wherein said aromatic group which may contain a substituent group is a phenyl group, a biphenyl group, or a naphthyl group; a heteroaryl group in which a part of the carbon atoms which constitutes the rings of a phenyl group, a biphenyl group or a naphthyl group are substituted with heteroatoms; or a benzyl group, a phenylhyl group, a 1-naphthylmethyl group, a 2-naphthylmethyl group, a 1-naphthylethyl group, or a 2-naphthylethyl group.

* * * * *

UNITED STATES PATENT AND TRADEMARK OFFICE
CERTIFICATE OF CORRECTION

| | |
|---|---|
| PATENT NO. | : 7,745,097 B2 |
| APPLICATION NO. | : 12/174293 |
| DATED | : June 29, 2010 |
| INVENTOR(S) | : Hada et al. |

It is certified that error appears in the above-identified patent and that said Letters Patent is hereby corrected as shown below:

Column 6, Line 11, Change "1" to --1,--.

Column 6, Line 33-34, Change "naphtyl" to --naphthyl--.

Column 6, Line 43, Change "subustituent" to --substituent--.

Column 7, Line 12, Change "hagelon" to --halogen--.

Column 7, Line 17, Change "naphtyl" to --naphthyl--.

Column 7, Line 53, Change "naphtyl" to --naphthyl--.

Column 7, Line 65, Change "phenantryl" to --phenanthryl--.

Column 8, Line 8, Change "R2" to --$R^2$--.

Column 8, Line 12, Change "$R^1$" to --$R^2$--.

Column 8, Line 40, Change "atoms)" to --atoms).--.

Column 8-9, Line 67 (Col. 8), Line 1 (Col. 9), Change "flurorinated" to --fluorinated--.

Column 9, Line 6, Change "$CH_2CH_2CH_2CF_2$–," to -- –$CH_2CH_2CH_2CF_2$–,--.

Column 9, Line 7, Change "–$CH_2CF_2CF_2CF_2$–," to -- –$CH_2CF_2CF_2CF_2$–.--.

Column 10, Line 40, Change "methal" to --metal--.

Column 10, Line 42, Change "tetrahydrofran," to --tetrahydrofuran,--.

Column 12, Line 25, Change "R." to --$R^1$.--.

Column 13, Line 1, Change "(1)" to --(I)--.

Column 15, Line 24-25, Change "α-(hydroxyalkylacrylic" to --α-(hydroxyalkyl)acrylic--.

Column 15, Line 27, Change "ten" to --term--.

Column 18, Line 53, Change "a-position" to --α-position--.

Column 19, Line 13, Change "to3;" to --to 3;--.

Column 21, Line 47, Change "alkylen" to --alkylene--.

Column 59, Line 14, Change "strucutural" to --structural--.

Signed and Sealed this
Seventeenth Day of July, 2012

David J. Kappos
*Director of the United States Patent and Trademark Office*

CERTIFICATE OF CORRECTION (continued)

Column 60, Line 37, Change "tris(4-hydroxyphenylmethane," to --tris(4-hydroxyphenyl)methane,--.

Column 60, Line 63, Change "(B1-1)" to --(b1-1)--.

Column 63, Line 44, Change "methansulfonate," to --methanesulfonate,--.

Column 63, Line 56-60, Change " " to -- 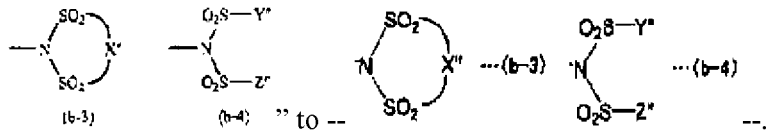 --.

Column 64, Line 59, Change "n6" to --$n_6$--.

Column 66, Line 4, Change "(Thereinafter," to --(hereinafter,--.

Column 67, Line 15, Change "phenantryl" to --phenanthryl--.

Column 67, Line 63, Change "α-(b enzenesulfonyloxyimino)" to --α-(benzenesulfonyloxyimino)--.

Column 68, Line 1, Change "α-benzenesulfonyloxyimino)" to --α-(benzenesulfonyloxyimino)--.

Column 68, Line 19, Change "cyclohexylacetonitile," to --cyclohexylacetonitrile,--.

Column 68, Line 24, Change "cyclopentenylacetonitile," to --cyclopentenylacetonitrile,--.

Column 69, Line 51, Change "alkyamines" to --alkylamines--.

Column 70, Line 45, Change "phenylphosphlinic" to --phenylphosphinic--.

Column 72, Line 36, Change "(VV)," to --(VUV),--.

Column 72, Line 41, Change "inacitive" to --inactive--.

Column 73, Line 56, Change "$Y^1$–$SO_3$–." to --$Y^1$–$SO_3^{\bullet}$.--.

Column 74, Line 61, Change "($H^c$)," to --($H^c$)),--.

Column 74, Line 62, Change "($H^c$)," to --($H^c$)),--.

Column 75, Line 18-19, Change "pentamethylenesulflde," to --pentamethylenesulfide,--.

Column 76, Line 36, Before "7.39" change "Naphtyl))," to --Naphthyl)),--.

Column 76, Line 36, Before "5.20" change "Naphtyl))," to --Naphthyl)),--.

Column 77, Line 6, Change "Naphtyl))," to --Naphthyl)),--.

Column 77, Line 62, Change "($H^b$))" to --($H^b$)),--.

Column 77, Line 63, Change "($H^c$)." to --($H^c$)).--.

Column 79, Line 39, Change "Prom" to --From--.

Column 79, Line 44, Change "(t" to --(t,--.

Column 79, Line 51, Change "(b0-11)," to --(b1-11),--.

Column 79, Line 51, Change "(b0-13)," to --(b1-13),--.

Column 81, Line 47, Change "posive" to --positive--.

Column 82, Line 14, Change "(b2-13)" to --(b2-13).--.

CERTIFICATE OF CORRECTION (continued)

Column 83, Line 57, Change "US" to --L/S--.

Column 85, Line 50, In Claim 10, after " 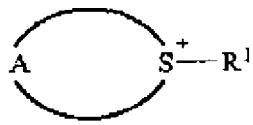 " delete ".".

Column 88, Line 9, In Claim 18, change "phenylhyl" to --phenethyl--.

Column 88, Line 18, In Claim 19, change "phenylhyl" to --phenethyl--.